US012790381B2

(12) United States Patent
Take et al.

(10) Patent No.: US 12,790,381 B2
(45) Date of Patent: Nov. 10, 2026

(54) CAR-EXPRESSING T CELLS AND CAR EXPRESSION VECTOR

(71) Applicants: NOILE-IMMUNE BIOTECH, INC., Tokyo (JP); Takeda Pharmaceutical Company Limited, Osaka (JP)

(72) Inventors: Chihiro Take, Kanagawa (JP); Takayuki Tatamiya, Kanagawa (JP); Akiko Yamaguchi, Kanagawa (JP)

(73) Assignees: NOILE-IMMUNE BIOTECH, INC., Tokyo (JP); Takeda Pharmaceutical Company Limited, Osaka (JP)

( * ) Notice: Subject to any disclaimer, the term of this patent is extended or adjusted under 35 U.S.C. 154(b) by 1103 days.

(21) Appl. No.: 17/271,451

(22) PCT Filed: Aug. 30, 2019

(86) PCT No.: PCT/JP2019/034055
§ 371 (c)(1),
(2) Date: Feb. 25, 2021

(87) PCT Pub. No.: WO2020/045610
PCT Pub. Date: Mar. 5, 2020

(65) Prior Publication Data

US 2021/0309712 A1 Oct. 7, 2021

(30) Foreign Application Priority Data

Aug. 31, 2018 (JP) ................................ 2018-163310

(51) Int. Cl.
*C12N 15/867* (2006.01)
*A61K 38/00* (2006.01)
(Continued)

(52) U.S. Cl.
CPC .......... *C07K 14/7051* (2013.01); *A61K 40/11* (2025.01); *A61K 40/31* (2025.01); *A61K 40/35* (2025.01); *A61K 40/4217* (2025.01); *A61K 40/4221* (2025.01); *A61K 40/4236* (2025.01); *A61K 48/00* (2013.01); *A61P 35/00* (2018.01); *A61P 35/02* (2018.01); *C07K 14/521* (2013.01); *C07K 14/523* (2013.01); *C07K 14/54* (2013.01); *C07K 14/5409* (2013.01); *C07K 14/5443* (2013.01); *C07K 14/7155* (2013.01); *C07K 16/2887* (2013.01); *C12N 5/0636* (2013.01); *C12N 5/10* (2013.01); *C12N 15/85* (2013.01); *C12N 15/86* (2013.01); *C12N 15/867* (2013.01); *A61K 38/00* (2013.01); *A61K 2039/82* (2018.08); *A61K 2039/876* (2018.08); *A61K 2121/00* (2013.01); *A61K 2239/38* (2023.05); *A61K 2239/50* (2023.05); *A61K 2239/57* (2023.05); *C07K 2319/00* (2013.01); *C07K 2319/02* (2013.01); *C07K 2319/03* (2013.01); *C12N 2501/2315* (2013.01); *C12N 2501/2318* (2013.01); *C12N 2501/2321* (2013.01); *C12N 2501/2327* (2013.01);
(Continued)

(58) Field of Classification Search
CPC ............ C07K 14/7051; C07K 14/5443; C07K 14/7155; C07K 14/523; C07K 14/54; C07K 2319/02; C07K 2319/03; C07K 14/521; C07K 14/5409; C07K 2319/00; A61K 35/17; A61K 38/00; A61K 39/4611; A61K 39/4631; A61K 39/464419; A61K 39/464424; A61K 39/464442; A61K 2039/82; A61K 2039/876; A61K 2239/38; A61K 2239/50; A61K 2239/57; A61K 48/00; A61P 35/00; A61P 35/02; C12N 2501/2315; C12N 2501/2318; C12N 2501/2321; C12N 2501/2327; C12N 2501/599; C12N 5/0636; C12N 2510/00; C12N 2740/13043; C12N 5/10; C12N 15/63; C12N 15/867; C12N 15/85
See application file for complete search history.

(56) References Cited

U.S. PATENT DOCUMENTS 10,525,082 B2 1/2020 Crane et al.
11,337,997 B2 5/2022 Tamada et al.
(Continued)

FOREIGN PATENT DOCUMENTS

CN 107109421 A 8/2017
CN 109055430 A 12/2018
(Continued)

OTHER PUBLICATIONS

Hurton et al. "Tethered IL-15 augments antitumor activity and promotes a stem-cell memory subset in tumor-specific T cells". PNAS, Nov. 14, 2016, 113(48):E7788-E7797 (Supporting Information Appendix) (Year: 2016).*
(Continued)

*Primary Examiner* — Mark Halvorson
*Assistant Examiner* — Lea S O'Brien
(74) *Attorney, Agent, or Firm* — Foley & Lardner LLP

(57) ABSTRACT

The present invention provides immune cells (such as CAR-T cells) having higher antitumor activity than immune cells (such as CAR-T cells) expressing a CAR alone (not expressing cytokines and/or chemokines). A T cell provided in one aspect of the present invention expresses (1) a chimeric antigen receptor (CAR), (2) at least one selected from the group consisting of interleukin-15 (IL-15), interleukin-18 (IL-18), interleukin-21 (IL-21), and interleukin-27 (IL-27), and (3) CC chemokine ligand 19 (CCL19).

18 Claims, 16 Drawing Sheets

Specification includes a Sequence Listing.

(51) Int. Cl.

| | |
|---|---|
| *A61K 39/00* | (2006.01) |
| *A61K 40/11* | (2025.01) |
| *A61K 40/31* | (2025.01) |
| *A61K 40/35* | (2025.01) |
| *A61K 40/42* | (2025.01) |
| *A61K 48/00* | (2006.01) |
| *A61P 35/00* | (2006.01) |
| *A61P 35/02* | (2006.01) |
| *C07K 14/52* | (2006.01) |
| *C07K 14/54* | (2006.01) |
| *C07K 14/705* | (2006.01) |
| *C07K 14/715* | (2006.01) |
| *C07K 16/28* | (2006.01) |
| *C12N 5/0783* | (2010.01) |
| *C12N 5/10* | (2006.01) |
| *C12N 15/63* | (2006.01) |
| *C12N 15/85* | (2006.01) |
| *C12N 15/86* | (2006.01) |

(52) U.S. Cl.

CPC .... *C12N 2501/599* (2013.01); *C12N 2510/00* (2013.01); *C12N 2740/10043* (2013.01); *C12N 2740/13043* (2013.01)

(56) References Cited

U.S. PATENT DOCUMENTS

| | | | | |
|---|---|---|---|---|
| 2013/0071414 | A1 | 3/2013 | Dotti et al. | |
| 2014/0255363 | A1 | 9/2014 | Metelitsa et al. | |
| 2016/0096892 | A1 | 4/2016 | Brogdon et al. | |
| 2016/0361360 | A1 | 12/2016 | Chang et al. | |
| 2017/0291953 | A1 | 10/2017 | Tamada et al. | |
| 2018/0291089 | A1 | 10/2018 | Epstein et al. | |
| 2019/0099446 | A1 | 4/2019 | Tamada et al. | |
| 2020/0323920 | A1 | 10/2020 | Tamada et al. | |
| 2024/0139248 | A1* | 5/2024 | Tamada | C07K 14/7051 |
| 2024/0350627 | A1* | 10/2024 | Take | C07K 14/70517 |
| 2024/0374721 | A1* | 11/2024 | Take | C07K 14/523 |

FOREIGN PATENT DOCUMENTS

| | | | | |
|---|---|---|---|---|
| CO | 2020007832 | | 10/2020 | |
| EP | 3205720 | A1 * | 8/2017 | A61K 35/17 |
| JP | 2017-536099 | A | 12/2017 | |
| TW | 201619377 | A | 6/2016 | |
| WO | WO-2007/037780 | A2 | 4/2007 | |
| WO | WO-2013/040371 | A2 | 3/2013 | |
| WO | WO-2014/186469 | A2 | 11/2014 | |
| WO | WO-2016/056228 | A1 | 4/2016 | |
| WO | WO-2016/061142 | A1 | 4/2016 | |
| WO | WO-2017/019848 | A1 | 2/2017 | |
| WO | WO-2017/159736 | A1 | 9/2017 | |
| WO | WO-2017/222593 | A1 | 12/2017 | |
| WO | WO-2018/014038 | A1 | 1/2018 | |
| WO | WO-2018/027155 | A1 | 2/2018 | |
| WO | WO-2018/073393 | A2 | 4/2018 | |
| WO | WO-2019/124468 | A1 | 6/2019 | |
| WO | WO-2020/010284 | A1 | 1/2020 | |

OTHER PUBLICATIONS

Olsen et al. "Crystal Structure of the Interleukin-15a Interleukin-15 Receptor a Complex". Journal of Biological Chemistry Oct. 2007 282(51):37191-204). (Year: 2007).*

Wu et al. "The IL-15 receptor {alpha} chain cytoplasmic domain is critical for normal IL-15Ralpha function but is not required for trans-presentation". Blood. Dec. 1, 2008;112(12):4411-9. doi: 10.1182/blood-2007-03-080697. Epub Sep. 16, 2008. PMID: 18796634; PMCID: PMC2597117. (Year: 2008).*

Kurys et al. "The Long Signal Peptide Isoform and Its Alternative Processing Direct the Intracellular Trafficking of Interleukin-15" vol. 275, Issue 39, Sep. 29, 2000, pp. 30653-30659 (Year: 2000).*

Xu et al. "Closely related T-memory stem cells correlate with in vivo expansion of CAR.CD19-T cells and are preserved by IL-7 and IL-15". Blood (2014) 123 (24): 3750-3759. https://doi.org/10.1182/blood-2014-01-552174 (Year: 2014).*

Jung et al, "CCR7 expression alters memory CD8 T-cell homeostasis by regulating occupancy in IL-7- and IL-15-dependent niches", (2016). Proc. Natl. Acad. Sci. U.S.A.113 (29) 8278-8283, https://doi.org/10.1073/pnas. 1602899113 (Year: 2016).*

Zhao et al. "Enhanced antitumor immunity is elicited by adenovirus-mediated gene transfer of CCL21 and IL-15 in murine colon carcinomas". Cellular Immunology vol. 289, Issues 1-2, May-Jun. 2014, pp. 155-161. https://doi.org/10.1016/j.cellimm.2014.03.020 (Year: 2014).*

Chmielewski et al., "Trucks: the fourth generation of CARs," Expert Opinion on Biological Therapy, May 18, 2015, 15(8):1145-1154.

Hu et al., "Augmentation of Antitumor Immunity by Human and Mouse CAR T Cells Secreting IL-18," Cell Reports, Sep. 26, 2017, 20(13):3025-3033.

Markley et al., "IL-7 and IL-21 are superior to IL-2 and IL-15 in promoting human T cell-mediated rejection of systemic lymphoma in immunodeficient mice," Blood, Feb. 26, 2010, 115(17):3508-3519.

Supplementary European Search Report dated Apr. 13, 2022 in EP 19853937.1.

Office Action and Search Report dated Oct. 28, 2023 in CN 201980056592.X, with English translation.

Office Action dated Dec. 20, 2022 in EA 202190624, with English translation.

Office Action dated Oct. 31, 2023 in JP 2020-539612, with English translation.

Office Action and Search Report dated Aug. 2, 2023 in TW 108131332, with English translation.

Adachi et al., "IL-7 and CCL19 expression in CAR-T cells improves immune cell infiltration and CAR-T cell survival in the tumor," Nature Biotechnology, Apr. 2018 (online Mar. 5, 2018), 36(4):346-351.

Batra et al., "Armored Glypican-3-Specific CAR T Cells for the Immunotherapy of Hepatocellular Carcinoma," ASGCT 2018, May 2018, Abstract 969.

Hurton et al., "Tethered IL-15 augments antitumor activity and promotes a stem-cell memory subset in tumor-specific T cells," PNAS, Nov. 14, 2016, 113(48):E7788-E7797.

International Search Report dated Nov. 19, 2019 in PCT/JP2019/034055.

Mortier et al., "Soluble Interleukin-15 Receptor a(IL-15Ra)-sushi as a Selective and Potent Agonist of IL-15 Action through IL-15RB/y," J. Biol. Chem., Jan. 20, 2006, 281(3):1612-1619.

Rowley et al., "Expression of IL-15RA or an IL-15/IL-15RA fusion on CD8 T cells modifies adoptively transferred T-cell function in cis," European Journal of Immunology, Feb. 2009, 39(2):491-506.

Sasaoka et al., "Treatment with IL-27 attenuates experimental colitis through the suppression of the development of IL-17-producing T helper cells," Am. J. Physiol. Gastrointest. Liver Physiol., 2011 (online Dec. 30, 2010), 300(4):G568-G576.

Hurton et al., "Tethered IL-15 augments antitumor activity and promotes a stem-cell memory subset in tumor-specific T cells," Proceedings of the National Academy of Sciences, Nov. 14, 2016, 113(48):E7788-E7797.

Office Action dated Sep. 30, 2024 in EP 19853937.1.

Office Action dated Sep. 12, 2024 in CO NC2021/0003508, with English translation.

Office Action dated Mar. 10, 2025 in MX/a/2021/002373, with English translation.

Read et al., "IL-2, IL-7, and IL-15: Multistage regulators of CD4 T helper cell differentiation," Experimental Hematology, 2016, 44(9):799-808.

Office Action dated Oct. 12, 2023 in NC2021/0003508, with English translation.

* cited by examiner

[Figure 1]
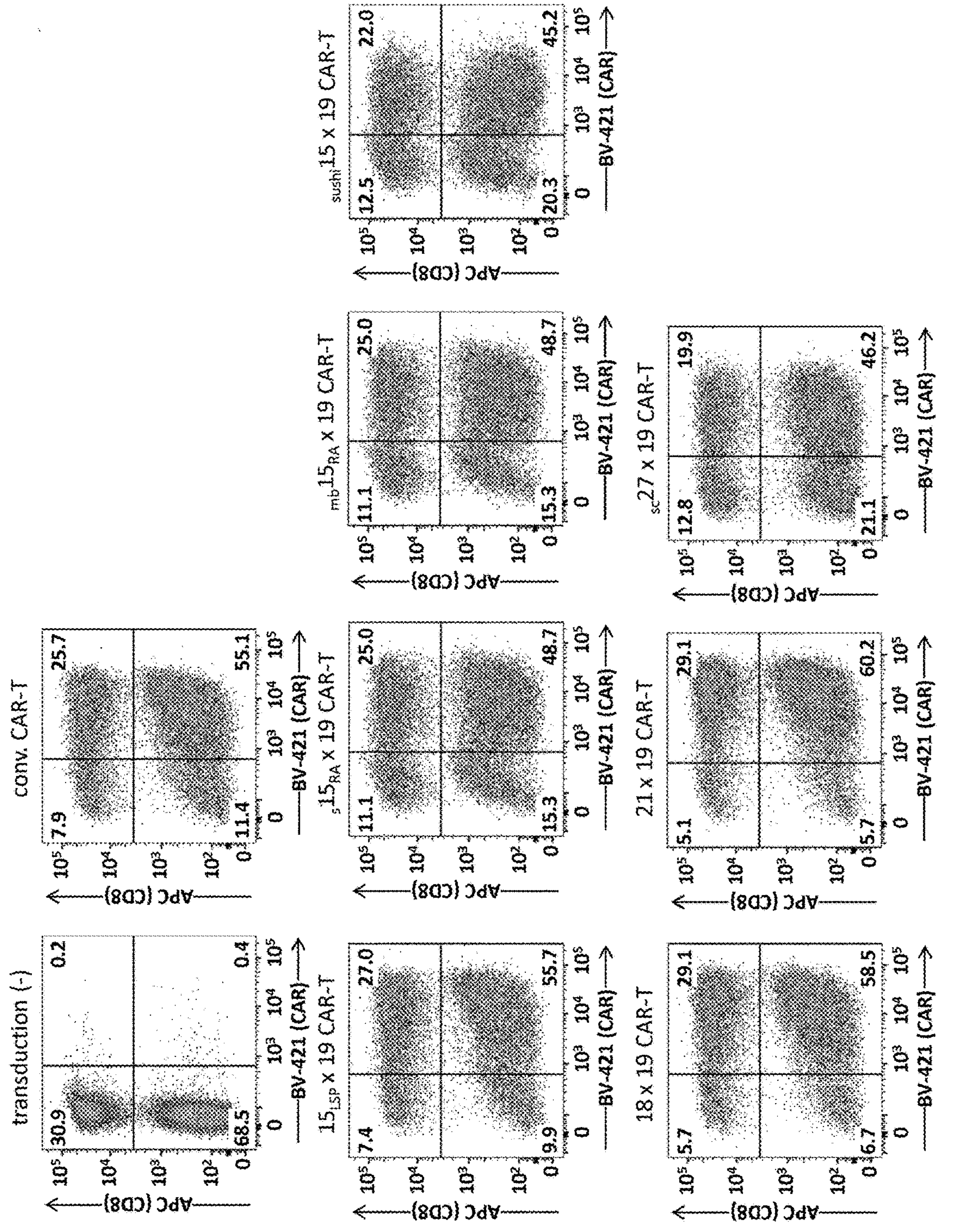

[Figure 2]
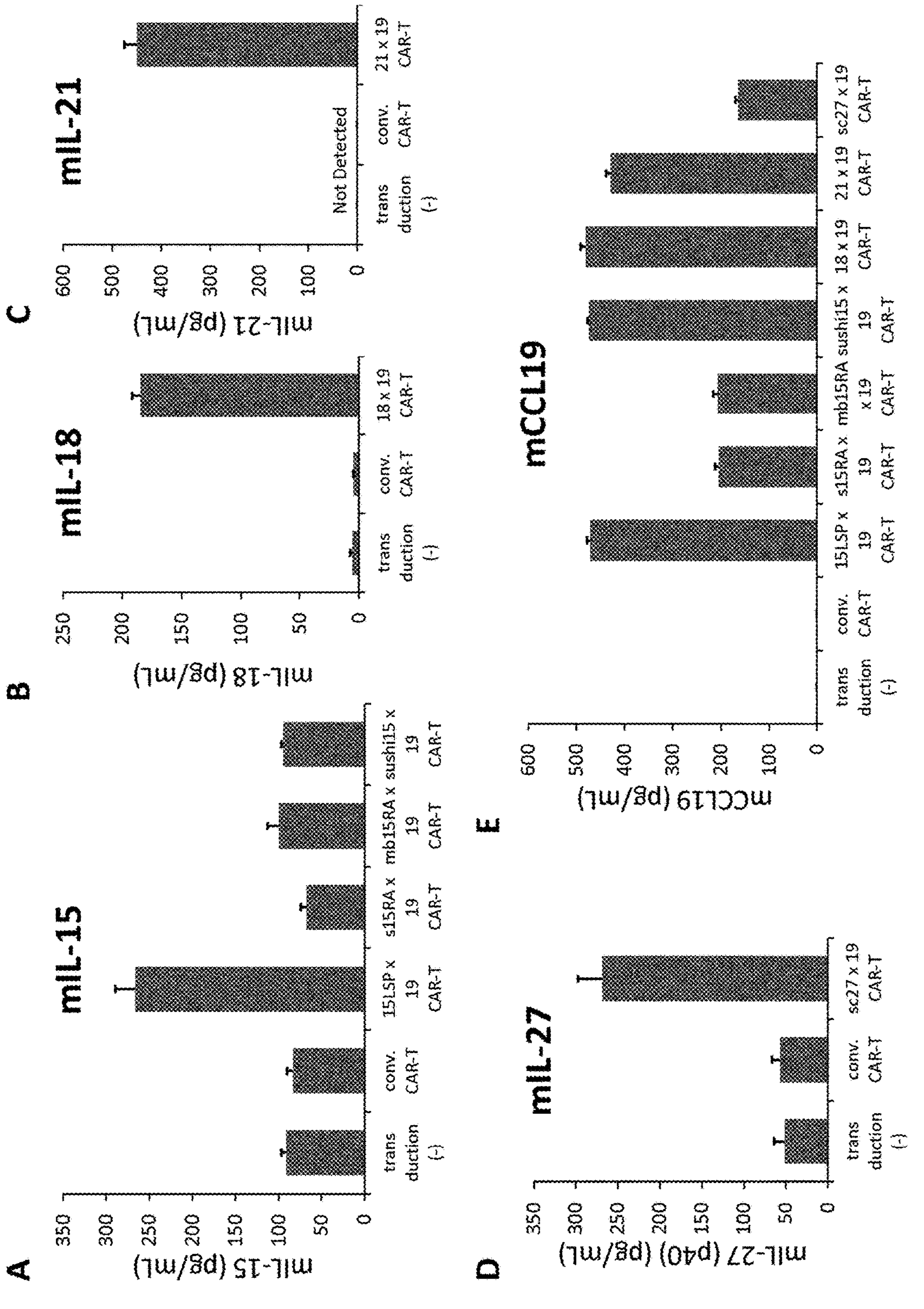

[Figure 3]
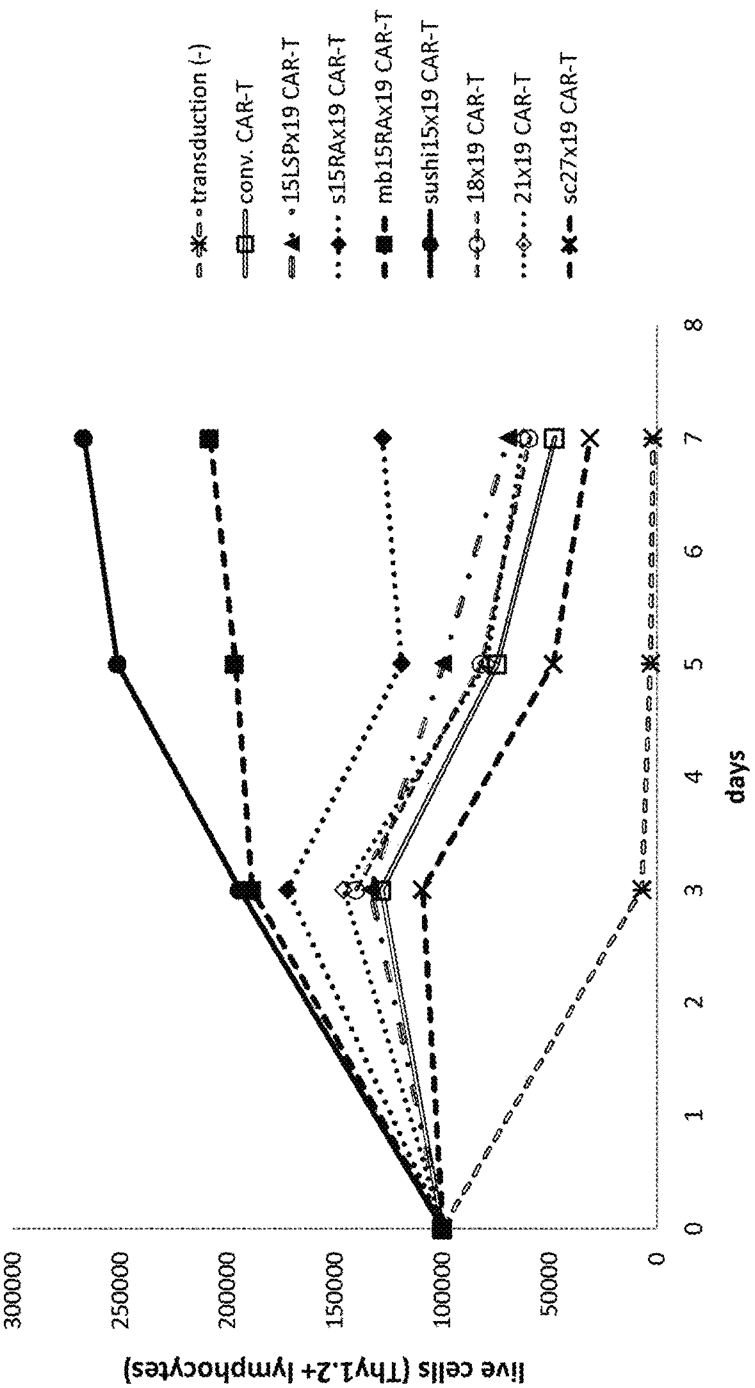

[Figure 4]
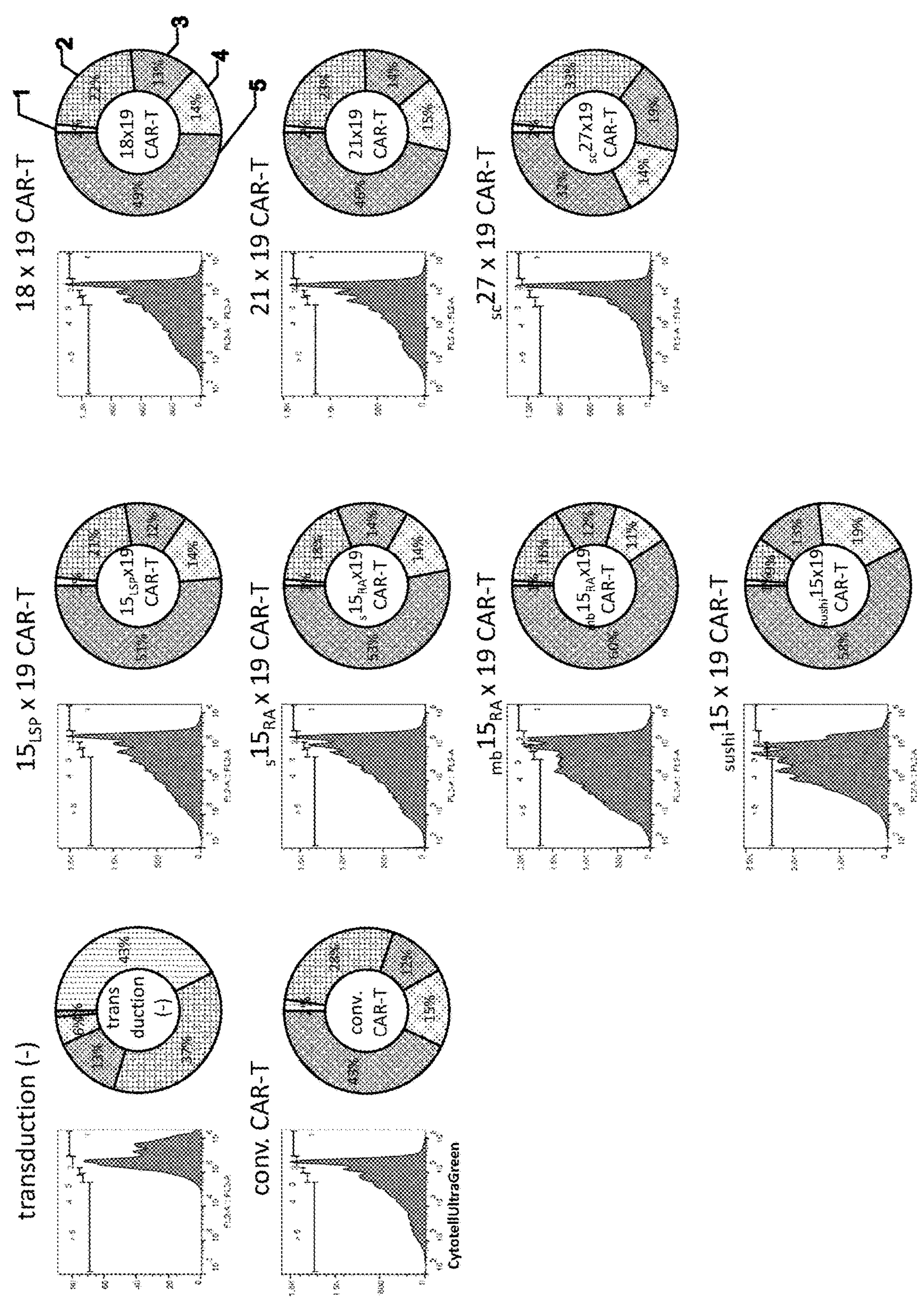

[Figure 5]
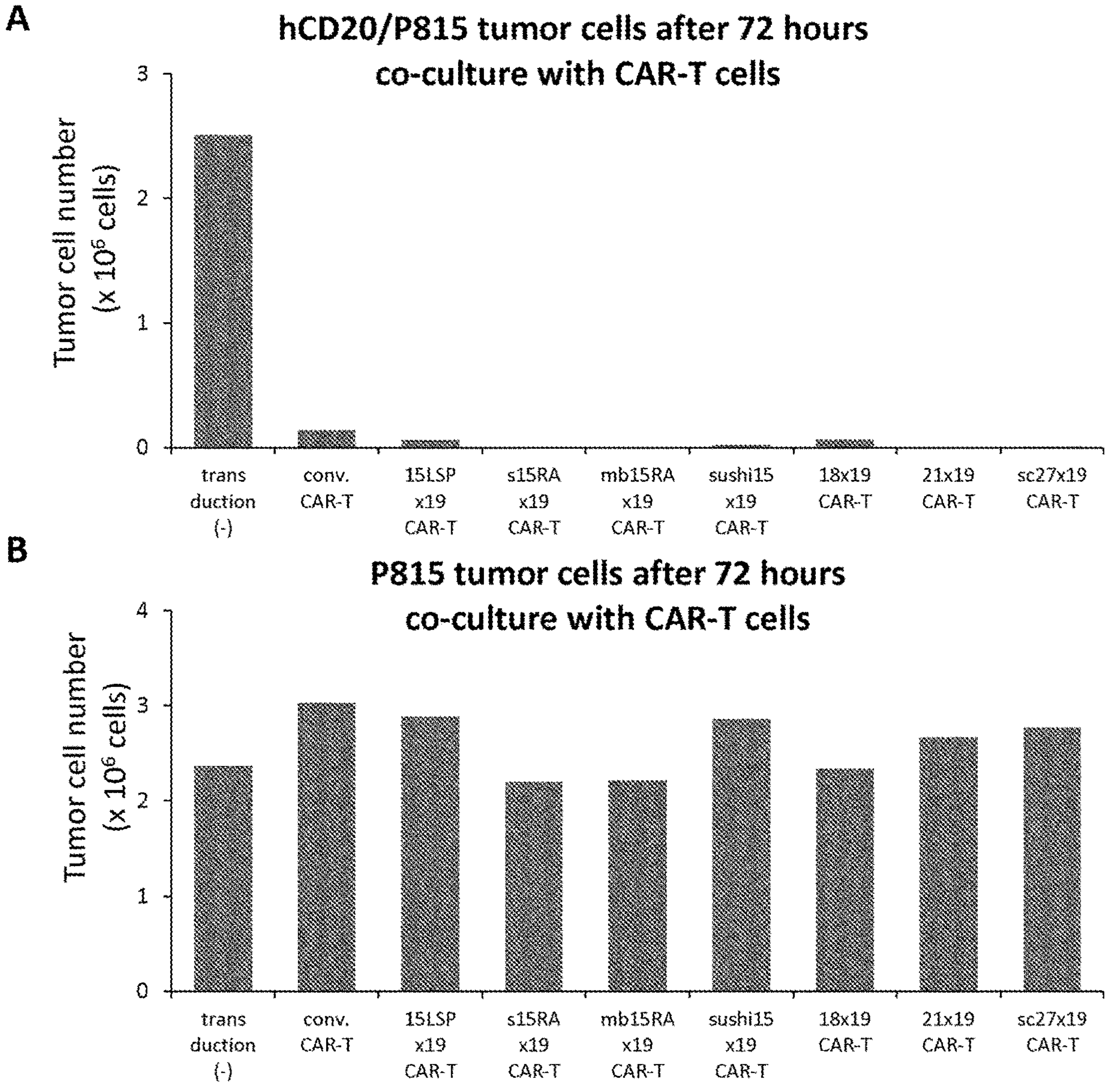

[Figure 6]
A
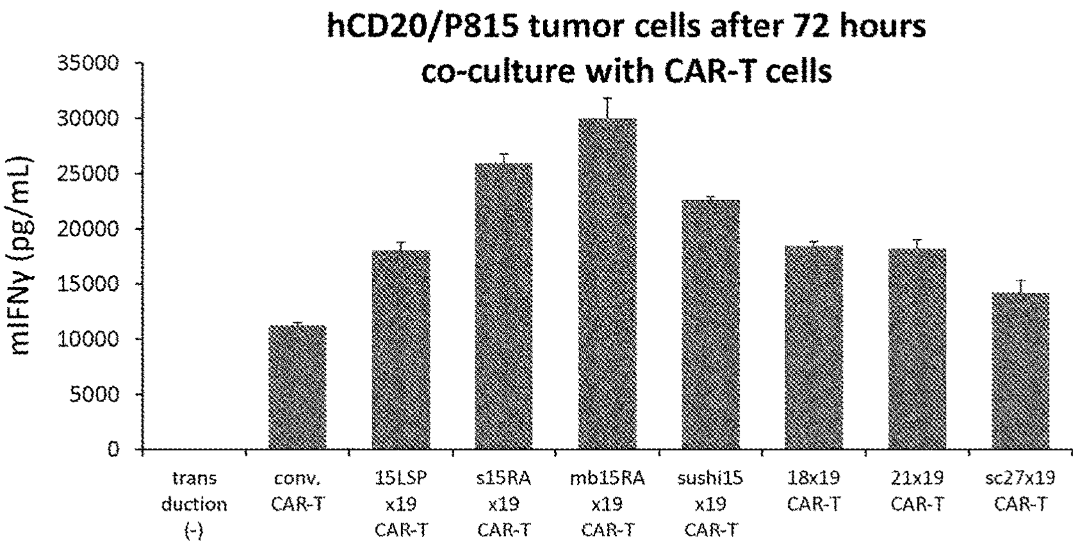
B
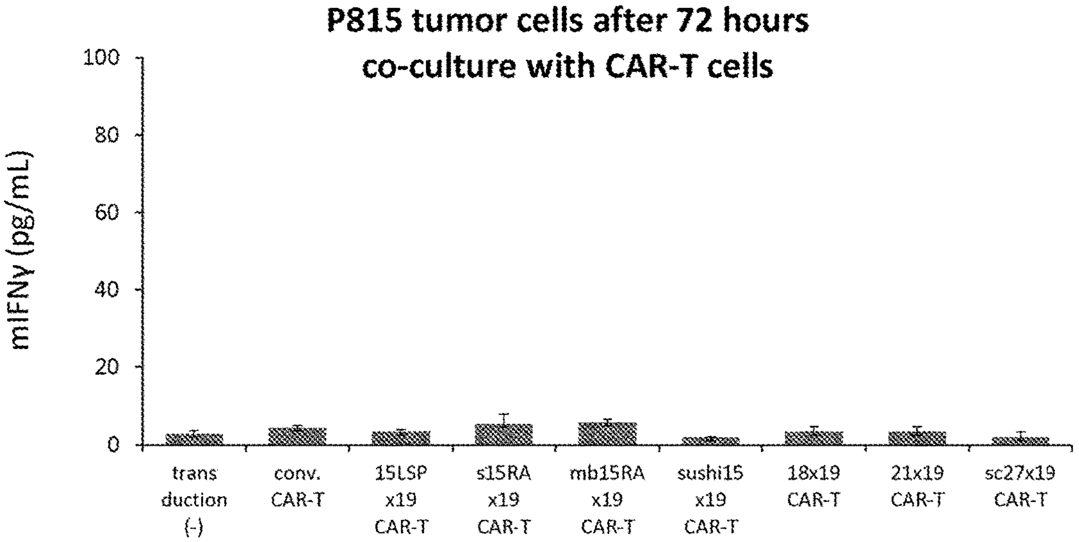

[Figure 7]

SEQ ID NO: 1: Anti-human CD20 CAR DNA fragment (DNA fragment #1)

anti-human CD20 scFv

CCATGGACTGGACCTGGCGGATCCTGTTCCTGGTGGCTGCTGCTACAGGCGCCCACAGCC

Nco I

AGATCGTGCTGTCTCAGTCTCCCGCCATCCTGTCTGCTAGCCCTGGCGAGAAAGTGACCA

TGACCTGCAGAGCCAGCAGCAGCGTGTCCTACATCCACTGGTTCCAGCAGAAGCCCGGCA

GCAGCCCCAAGCCTTGGATCTACGCCACAAGCAACCTGGCCTCTGGCGTGCCAGTGCGGT

TTAGCGGCTCTGGCTCTGGCACCAGCTACAGCCTGACCATCAGCAGAGTGGAAGCCGAGG

ACGCCGCCACCTACTACTGTCAGCAGTGGACCAGCAACCCCCCCACATTCGGCGGAGGCA

CCAAGCTGGAAATCAAGGGCGGAGGCGGATCTGGCGGCGGAGGATCTGGGGGAGGCGGCT

CTCAGGTGCAGCTGCAGCAGCCTGGCGCTGAGCTCGTGAAACCTGGCGCCTCCGTGAAGA

TGAGCTGCAAGGCCAGCGGCTACACCTTCACAAGCTACAACATGCACTGGGTCAAGCAGA

CCCCTGGCAGAGGCCTGGAATGGATCGGCGCTATCTACCCCGGCAACGGCGACACCTCCT

ACAACCAGAAGTTCAAGGGCAAGGCCACCCTGACCGCCGACAAGAGCAGCAGCACAGCCT

ACATGCAGCTGTCGTCCCTGACCAGCGAGGACAGCGCCGTGTACTACTGCGCCAGATCTA

CCTACTACGGCGGCGACTGGTACTTCAACGTCTGGGGCGCTGGCACCACCGTGACCGTGT

3rd TM domain (CD8)

CTGCTGCGGCCGCAGTCGTGCCAGTCCTTCAGAAAGTGAACTCTACTACTACCAAGCCAG

TGCTGCGAACTCCCTCACCTGTGCACCCTACCGGGACATCTCAGCCCCAGAGACCAGAAG

ATTGTCGGCCCCGTGGCTCAGTGAAGGGGACCGGATTGGACTTCGCCTGTGATATTTACA

TCTGGGCACCCTTGGCCGGAATCTGCGTGGCCCCTCTGCTGTCCTTGATCATCACTCTCA

CP domain (CD28_4-1BB_CD3z)

TCTGCTACCACAGGAGCCGAAATAGTAGAAGGAACAGACTCCTTCAAAGTGACTACATGA

ACATGACTCCCCGGAGGCCTGGGCTCACTCGAAAGCCTTACCAGCCCTACGCCCCTGCCA

GAGACTTTGCAGCGTACCGCCCCAAATGGATCAGGAAAAAATTCCCCCACATATTCAAGC

AACCATTTAAGAAGACCACTGGAGCAGCTCAAGAGGAAGATGCTTGTAGCTGCCGATGTC

CACAGGAAGAAGAAGGAGGAGGAGCAGGCTATGAGCTGAGAGCAAAATTCAGCAGGAGTG

CAGAGACTGCTGCCAACCTGCAGGACCCCAACCAGCTCTACAATGAGCTCAATCTAGGGC

Sbf I

GAAGAGAGGAATATGACGTCTTGGAGAAGAAGCGGGCTCGGGATCCAGAGATGGGAGGCA

AACAGCAGAGGAGGAGGAACCCCCAGGAAGGCGTATACAATGCACTGCAGAAAGACAAGA

TGGCAGAAGCCTACAGTGAGATCGGCACAAAAGGCGAGAGGCGGAGAGGCAAGGGGCACG

ATGGCCTTTACCAGGGTCTCAGCACTGCCACCAAGGACACCTATGATGCCCTGCATATGC

AGACCCTGGCCCCTCGC

[Figure 8]

SEQ ID NO: 3: MCS DNA fragment encoding stop codons and restriction enzyme sites (DNA fragment #2)

TGAAAGCTTAAACCAGTTAACTGGAAAACGCGTAAAGTCGAC
Stop codon Sal I

[Figure 9]

SEQ ID NO: 4: IL15LSP_F2A_CCL19 DNA fragment (DNA fragment #3)

F2A
GAATTCGGCAGCGGCGTGAAGCAGACCCTGAACTTCGACCTGCTGAAGCTGGCCGGAGAC
Mouse IL-15 long signal peptide
GTGGAGAGCAACCCTGGCCCTATGAAGATCCTGAAGCCCTACATGAGGAACACCAGCATC
Mouse IL-15
TCCTGTTACCTCTGTTTCCTGCTGAACAGCCACTTCCTGACCGAGGCCGGCATCCACGTG
TTCATCCTGGGCTGCGTGTCCGTGGGCCTGCCTAAGACCGAGGCCAACTGGATCGACGTG
AGATACGACCTGGAGAAGATCGAGAGCCTGATCCAGAGCATCCACATCGACACCACACTG
TACACCGACAGCGACTTCCACCCCAGCTGCAAGGTGACCGCCATGAACTGCTTTCTGCTG
GAGCTGCAGGTGATCCTGCACGAGTACAGCAACATGACCCTGAACGAGACCGTGAGAAAC
GTGCTGTACCTGGCCAACTCCACCCTGAGCAGCAACAAGAACGTGGCCGAGAGCGGCTGC
AAGGAGTGCGAGGAGCTCGAGGAGAAAACCTTCACCGAGTTCCTGCAGAGCTTCATCAGG
F2A
ATCGTCCAGATGTTCATCAACACCAGCGGCAGCGGCGTGAAGCAGACCCTGAACTTCGAC
Mouse CCL19
CTGCTGAAGCTGGCCGGAGACGTGGAGAGCAACCCTGGCCCATGCATGGCCCCCAGGGTG
ACCCCTCTGCTGGCCTTCAGCCTGCTGGTGCTGTGGACCTTCCCTGCCCCTACCCTGGGA
GGAGCCAATGACGCCGAGGACTGCTGCCTGAGCGTGACCCAGAGACCCATCCCCGGCAAC
ATCGTGAAGGCCTTCAGGTACCTGCTGAACGAGGACGGCTGCAGAGTGCCTGCCGTGGTG
TTCACCACCCTGAGGGGCTACCAGCTGTGTGCTCCCCCTGACCAGCCTTGGGTGGACAGG
ATCATCAGGAGGCTGAAGAAGAGCAGCGCCAAGAACAAGGGCAACAGCACCAGGAGGAGC
CCCGTGAGCTGAAAGCTTAAACCAGTTAACTGGAAAACGCGTAAAGTCGAC
Stop codon Sal I

[Figure 10]

SEQ ID NO: 6: sIL15RA_F2A_CCL19 DNA fragment (DNA fragment #4)

F2A
GAATTCGGCAGCGGCGTGAAGCAGACCCTGAACTTCGACCTGCTGAAGCTGGCCGGAGAC
Mouse IL-2 signal peptide
GTGGAGAGCAACCCTGGCCCTATGTATTCCATGCAGCTGGCCAGCTGTGTGACCCTGACA
Mouse IL-15
CTGGTGCTGCTGGTGAACAGCGGCATCCACGTGTTCATTCTGGGATGCGTCTCCGTGGGC
CTCCCCAAGACCGAGGCTAACTGGATCGACGTCAGGTACGACCTGGAGAAGATCGAAAGC
CTGATCCAGTCCATCCACATCGATACAACCCTGTACACAGATTCCGACTTCCACCCCTCC
TGTAAGGTCACCGCCATGAACTGCTTCCTCCTGGAACTCCAGGTCATCCTGCACGAGTAC
TCCAACATGACCCTGAACGAAACCGTGAGGAATGTGCTCTACCTCGCCAACTCCACACTG
AGCTCCAATAAGAACGTGGCTGAGAGCGGCTGCAAGGAGTGTGAGGAGCTGGAAGAGAAG
ACCTTCACCGAGTTCCTGCAGAGCTTCATCAGGATCGTGCAGATGTTCATCAACACAAGC
26aa linker
TCCGGCGGAGGATCCGGAGGAGGAGGAAGCGGAGGCGGCGGCTCCGGAGGCGGAGGAAGC
Mouse IL-15RA Extracellular domain
GGAGGAGGAAGCCTGCAAGGAACCACCTGTCCCCCTCCCGTGTCCATCGAGCACGCCGAC
ATCAGGGTGAAGAACTACTCCGTCAACAGCAGGGAAAGGTACGTGTGCAACTCCGGCTTT
AAGAGGAAGGCCGGCACCAGCACCCTCATCGAGTGCGTGATCAACAAGAACACAAACGTG
GCCCACTGGACCACCCCCAGCCTGAAGTGTATTAGAGACCCCAGCCTGGCTCATTACAGC
CCCGTGCCCACAGTGGTGACACCCAAGGTGACAAGCCAGCCTGAGAGCCCTAGCCCTAGC
GCCAAAGAGCCCGAGGCCTTTTCCCCCAAGTCCGACACCGCCATGACCACCGAGACAGCC
ATCATGCCTGGCAGCAGACTGACCCCTAGCCAGACCACATCCGCTGGCACCACAGGCACC
GGCTCCCACAAGAGCTCCAGAGCCCCTAGCCTGGCTGCCACAATGACACTGGAACCTACC
F2A
GCCTCCACCAGCCTCAGAATCACAGAGATCTCCCCCCACAGCAGCAAGATGACCAAGGGC
AGCGGCGTGAAGCAGACCCTGAACTTCGACCTGCTGAAGCTGGCCGGAGACGTGGAGAGC
Mouse CCL19
AACCCTGGCCCATGCATGGCCCCCAGGGTGACCCCTCTGCTGGCCTTCAGCCTGCTGGTG
CTGTGGACCTTCCCTGCCCCTACCCTGGGAGGAGCCAATGACGCCGAGGACTGCTGCCTG
AGCGTGACCCAGAGACCCATCCCCGGCAACATCGTGAAGGCCTTCAGGTACCTGCTGAAC
GAGGACGGCTGCAGAGTGCCTGCCGTGGTGTTCACCACCCTGAGGGGCTACCAGCTGTGT
GCTCCCCCTGACCAGCCTTGGGTGGACAGGATCATCAGGAGGCTGAAGAAGAGCAGCGCC
AAGAACAAGGGCAACAGCACCAGGAGGAGCCCCGTGAGCTGAAAGCTTAAACCAGTTAAC
Stop codon
TGGAAAACGCGTAAAGTCGAC
Sal I

[Figure 11]

SEQ ID NO: 8: $_{mb}$IL15$_{RA}$_F2A_CCL19 DNA fragment (DNA fragment #5)

F2A
GAATTCGGCAGCGGCGTGAAGCAGACCCTGAACTTCGACCTGCTGAAGCTGGCCGGAGAC
Mouse IL-2 signal peptide
GTGGAGAGCAACCCTGGCCCTATGTATTCCATGCAGCTGGCCAGCTGTGTGACCCTGACA
Mouse IL-15
CTGGTGCTGCTGGTGAACAGCGGCATCCACGTGTTCATTCTGGGATGCGTCTCCGTGGGC
CTCCCAAGACCGAGGCTAACTGGATCGACGTCAGGTACGACCTGGAGAAGATCGAAAGC
CTGATCCAGTCCATCCACATCGATACAACCCTGTACACAGATTCCGACTTCCACCCCTCC
TGTAAGGTCACCGCCATGAACTGCTTCCTCCTGGAACTCCAGGTCATCCTGCACGAGTAC
TCCAACATGACCCTGAACGAAACCGTGAGGAATGTGCTGTACCTCGCCAACTCCACACTG
AGCTCCAATAAGAACGTGGCTGAGAGCGGCTGCAAGGAGTGTGAGGAGCTGGAAGAGAAG
ACCTTCACCGAGTTCCTGCAGAGCTTCATCAGGATCGTGCAGATGTTCATCAACACAAGC
26aa linker
TCCGGCGGAGGATCCGGAGGAGGAGGAAGCGGAGGCGGCGGCTCCGGAGGCGGAGGAAGC
Mouse IL-15RA
GGAGGAGGAAGCCTGCAAGGAACCACCTGTCCCCCTCCCGTGTCCATCGAGCACGCCGAC
ATCAGGGTGAAGAACTACTCCGTCAACAGCAGGGAAAGGTACGTGTGCAACTCCGGCTTT
AAGAGGAAGGCCGGCACCAGCACCCTCATCGAGTGCGTGATCAACAAGAACACAAACGTG
GCCCACTGGACCACCCCCAGCCTGAAGTGTATTAGAGACCCCAGCCTGGCTCATTACAGC
CCCGTGCCCACAGTGGTGACACCCAAGGTGACAAGCCAGCCTGAGAGCCCTAGCCCTAGC
GCCAAAGAGCCCGAGGCCTTTTCCCCCAAGTCCGACACCGCCATGACCACCGAGACAGCC
ATCATGCCTGGCAGCAGACTGACCCCTAGCCAGACCACATCCGCTGGCACCACAGGCACC
GGCTCCCACAAGAGCTCCAGAGCCCCTAGCCTGGCTGCCACAATGACACTGGAACCTACC
GCCTCCACCAGCCTCAGAATCACAGAGATCTCCCCCCACAGCAGCAAGATGACCAAGGTG
GCCATCTCCACCTCCGTGCTGCTGGTGGGAGCCGGCGTGGTCATGGCCTTTCTGGCCTGG
TACATCAAGTCCAGGCAGCCTAGCCAACCTTGCAGGGTCGAGGTGGAAACTATGGAAACC
F2A
GTGCCGATGACCGTGAGGGCCAGCTCCAAGGAGGATGAAGACACCGGCGCCGGCAGCGGC
GTGAAGCAGACCCTGAACTTCGACCTGCTGAAGCTGGCCGGAGACGTGGAGAGCAACCCT
Mouse CCL19
GGCCCATGCATGGCCCCCAGGGTGACCCCTCTGCTGGCCTTCAGCCTGCTGGTGCTGTGG
ACCTTCCCTGCCCCTACCCTGGGAGGAGCCAATGACGCCGAGGACTGCTGCCTGAGCGTG
ACCCAGAGACCCATCCCCGGCAACATCGTGAAGGCCTTCAGGTACCTGCTGAACGAGGAC
GGCTGCAGAGTGCCTGCCGTGGTGTTCACCACCCTGAGGGGCTACCAGCTGTGTGCTCCC
CCTGACCAGCCTTGGGTGGACAGGATCATCAGGAGGCTGAAGAAGAGCAGCGCCAAGAAC
AAGGGCAACAGCACCAGGAGGAGCCCCGTGAGCTGAAAGCTTAAACCAGTTAACTGGAAA
Stop codon
ACGCGTAAAGTCGAC
Sal I

[Figure 12]

SEQ ID NO: 10: sushiIL15_F2A_CCL19 DNA fragment (DNA fragment #6)

F2A
GAATTCGGCAGCGGCGTGAAGCAGACCCTGAACTTCGACCTGCTGAAGCTGGCCGGAGAC
Mouse IL-15RAsushi
GTGGAGAGCAACCCTGGCCCTATGGCCTCCCCTCAGCTGAGAGGCTACGGCGTGCAGCT
ATCCCCGTGCTGCTGCTGCTGCTGCTGCTGCTGCTGCCTCTGAGAGTGACCCCTGGC
ACAACCTGCCCTCCTCCCGTGAGCATCGAGCACGCCGACATCAGGGTGAAGAACTACTCC
GTGAACAGCAGGGAGAGGTACGTGTGCAACAGCGGCTTCAAGAGGAAGGCCGGCACCAGC
ACCCTGATCGAGTGCGTGATCAACAAGAACACCAACGTGGCCCACTGGACCACCCCCAGC
26aa linker
CTGAAGTGCATCAGGAGCGGCGGCAGCGGCGGCGGCGGCAGCGGCGGCGGCAGCGGCGGC
Mouse IL-15
GGCGGCAGCCTGCAGAACTGGATCGACGTCAGGTACGACCTGGAGAAGATCGAAAGCCTG
ATCCAGTCCATCCAGATCGATACAACCCTGTACACAGATTCCGACTTCCACCCCTCCTGT
AAGGTCACCGCCATGAACTGCTTCCTCCTGGAACTCCAGGTCATCCTGCACGAGTACTCC
AACATGACCCTGAACGAAACCGTGAGGAATGTGCTGTACCTCGCCAACTCCACACTGAGC
TCCAATAAGAACGTGGCTGAGAGCGGCTGCAAGGAGTGTGAGGAGCTGGAAGAGAAGACC
F2A
TTCACCGAGTTCCTGCAGAGCTTCATCAGGATCGTGCAGATGTTCATCAACACAAGCGGC
AGCGGCGTGAAGCAGACCCTGAACTTCGACCTGCTGAAGCTGGCCGGAGACGTGGAGAGC
Mouse CCL19
AACCCTGGCCCATGCATGGCCCCCAGGGTGACCCCTCTGCTGGCCTTCAGCCTGCTGGTG
CTGTGGACCTTCCCTGCCCCTACCCTGGGAGGAGCCAATGACGCCGAGGACTGCTGCCTG
AGCGTGACCCAGAGACCCATCCCCGGCAACATCGTGAAGGCCTTCAGGTACCTGCTGAAC
GAGGACGGCTGCAGAGTGCCTGCCGTGGTGTTCACCACCCTGAGGGGCTACCAGCTGTGT
GCTCCCCCTGACCAGCCTTGGGTGGACAGGATCATCAGGAGGCTGAAGAAGAGCAGCGCC
AAGAACAAGGGCAACAGCACCAGGAGGAGCCCCGTGAGCTGAAAGCTTAAACCAGTTAAC
Stop codon
TGGAAAACGCGTAAAGTCGAC
Sal I

[Figure 13]

SEQ ID NO: 12: IL-18_F2A_CCL19 DNA fragment (DNA fragment #7)

```
      F2A
GAATTCGGCAGCGGCGTGAAGCAGACCCTGAACTTCGACCTGCTGAAGCTGGCCGGAGAC
                         Mouse IL-21
GTGGAGAGCAACCCTGGCCCTATGGAGAGGACCCTGGTGTGCCTGGTGGTGATTTTCCTG
GGCACCGTCGCCCATAAGAGCAGCCCCCAGGGACCGGACAGACTGCTGATCAGGCTGAGG
CACCTGATCGACATCGTGGAGCAGCTGAAGATCTACGAGAACGACCTGGACCCCGAGCTG
CTGAGCGCTCCTCAGGACGTGAAGGGACACTGCGAGCACGCCGCCTTCGCCTGTTTCCAG
AAGGCCAAGCTGAAGCCTTCCAACCCCGGCAACAACAAGACCTTCATCATCGACCTGGTG
GCCCAGCTGAGGAGAAGGCTGCCTGCCAGGAGGGGCGGAAAGAAGCAGAAGCACATCGCC
AAGTGCCCCAGCTGCGACTCCTACGAGAAGAGGACCCCCAAGGAGTTCCTGGAGAGGCTG
AAGTGGCTGCTGCAGAAGGTGTGCACACTGAACGCCTTCCTGAGCCTGCCTTGTTGCGTG
                           F2A
ACGGTGCCTCCCGTGCCTTCCGACAGCGGCAGCGGCGTGAAGCAGACCCTGAACTTCGAC
                                             Mouse CCL19
CTGCTGAAGCTGGCCGGAGACGTGGAGAGCAACCCTGGCCCATGCATGGCCCCCAGGGTG
ACCCCTCTGCTGGCCTTCAGCCTGCTGGTGCTGTGGACCTTCCCTGCCCCTACCCTGGGA
GGAGCCAATGACGCCGAGGACTGCTGCCTGAGCGTGACCCAGAGACCCATCCCCGGCAAC
ATCGTGAAGGCCTTCAGGTACCTGCTGAACGAGGACGGCTGCAGAGTGCCTGCCGTGGTG
TTCACCACCCTGAGGGGCTACCAGCTGTGTGCTCCCCCTGACCAGCCTTGGGTGGACAGG
ATCATCAGGAGGCTGAAGAAGAGCAGCGCCAAGAACAAGGGCAACAGCACCAGGAGGAGC
CCCGTGAGCTGAAAGCTTAAACCAGTTAACTGGAAAACGCGTAAAGTCGAC
         Stop codon                                 Sal I
```

[Figure 14]

SEQ ID NO: 14: IL-21_F2A_CCL19 DNA fragment (DNA fragment #8)

```
      F2A
GAATTCGGCAGCGGCGTGAAGCAGACCCTGAACTTCGACCTGCTGAAGCTGGCCGGAGAC
                     Mouse IL-21
GTGGAGAGCAACCCTGGCCCTATGGAGAGGACCCTGGTGTGCCTGGTGGTGATTTTCCTG
GGCACCGTCGCCCATAAGAGCAGCCCCCAGGGACCCGACAGACTGCTGATCAGGCTGAGG
CACCTGATCGACATCGTGGAGCAGCTGAAGATCTACGAGAACGACCTGGACCCCGAGCTG
CTGAGCGCTCCTCAGGACGTGAAGGGACACTGCGAGCACGCCGCCTTCGCCTGTTTCCAG
AAGGCCAAGCTGAAGCCTTCCAACCCCGGCAACAACAAGACCTTCATCATCGACCTGGTG
GCCCAGCTGAGGAGAAGGCTGCCTGCCAGGAGGGGCGGAAAGAAGCAGAAGCACATCGCC
AAGTGCCCCAGCTGCGACTCCTACGAGAAGAGGACCCCCAAGGAGTTCCTGGAGAGGCTG
AAGTGGCTGCTGCAGAAGGTGTGCACACTGAACGCCTTCCTGAGCCTGCCTTGTTGCGTG
                           F2A
ACGGTGCCTCCCGTGCCTTCCGACAGCGGCAGCGGCGTGAAGCAGACCCTGAACTTCGAC
                                               Mouse CCL19
CTGCTGAAGCTGGCCGGAGACGTGGAGAGCAACCCTGGCCCATGCATGGCCCCCAGGGTG
ACCCCTCTGCTGGCCTTCAGCCTGCTGGTGCTGTGGACCTTCCCTGCCCCTACCCTGGGA
GGAGCCAATGACGCCGAGGACTGCTGCCTGAGCGTGACCCAGAGACCCATCCCCGGCAAC
ATCGTGAAGGCCTTCAGGTACCTGCTGAACGAGGACGGCTGCAGAGTGCCTGCCGTGGTG
TTCACCACCCTGAGGGGCTACCAGCTGTGTGCTCCCCCTGACCAGCCTTGGGTGGACAGG
ATCATCAGGAGGCTGAAGAAGAGCAGCGCCAAGAACAAGGGCAACAGCACCAGGAGGAGC
CCCGTGAGCTGAAAGCTTAAACCAGTTAACTGGAAAACGCGTAAAGTCGAC
         Stop codon                          Sal I
```

[Figure 15]

SEQ ID NO: 16: scIL27_F2A_CCL19 DNA fragment (DNA fragment #9)

F2A
GAATTCGGCAGCGGCGTGAAGCAGACCCTGAACTTCGACCTGCTGAAGCTGGCCGGAGAC
Mouse EBI3
GTGGAGAGCAACCCTGGCCCTATGAGCAAGCTCCTCTTTCTGTCCCTCGCCCTCTGGGCC
AGCAGATCCCCTGGCTACACAGAAACAGCCCTGGTGGCCCTGTCCCAACCCAGAGTGCAG
TGTCACGCTTCCAGGTACCCCGTGGCTGTGGACTGCAGCTGGACCCCTCTGCAAGCCCCT
AATAGCACCAGGAGCACCTCCTTCATCGCCACCTACAGACTGGGAGTGGCCACCCAGCAG
CAGAGCCAGCCTTGCCTGCAGAGGTCCCCTCAGGCCTCCAGATGCACAATCCCTGATGTG
CACCTGTTTAGCACCGTGCCCTACATGCTGAACGTGACAGCCGTGCACCCTGGAGGAGCC
AGCAGCTCCCTCCTGGCCTTCGTCGCCGAGAGAATCATCAAGCCTGACCCCCCTGAGGGC
GTCAGACTGAGAACAGCTGGCCAGAGACTGCAGGTGCTGTGGCACCCTCCCGCCTCCTGG
CCTTTCCCCGATATCTTCTCCCTGAAGTACAGACTGAGGTACAGGCACAGAGGCGCTAGC
CACTTCAGACAGGTGGGCCCCATTGAGGCTACCACCTTTACCCTCAGGAATAGCAAGCCC
CATGCTAAGTACTGTATCCAGGTGTCCGCCCAGGATCTGACAGACTACGGCAAGCCCTCC
18aa linker
GACTGGAGCCTGCCTGGACAAGTGGAAAGCGCTCCCCACAAGCCTGGAAGCACATCCGGA
p28
AGCGGCAAACCCGGCAGCGGAGAGGGATCCACCAAAGGCTTCCCTACCGACCCCCTGTCT
TTACAAGAACTGAGAAGGGAGTTCACCGTGAGCCTGTATCTGGCCAGCAAGCTCCTCAGC
GAGGTGCAGGGCTATGTGCACAGCTTCGCCGAAAGCAGGCTGCCCGGCGTGAACCTGGAT
CTGCTGCCCCTGGGCTACCACCTGCCTAACGTGTCCCTGACCTTCCAGGCTTGGCATCAG
CTGTCCGACTCCGAGAGGCTCTGCTTTCTGGCCACCACCCTGAGGCCCTTCCCTGCCATG
CTGGGAGGACTGGGCACCCAGGGAACCTGGACCAGCAGCGAGAGGGAACAGCTGTGGGCC
ATGAGACTGGACCTGAGGGATCTGCACAGACACCTGAGGTTCCAGGTGCTGGCCGCCGGC
TTCAAGTGTAGCAAAGAGGAGGAGGACAAAGAAGAAGAACAAGAGGAAGAAGAGCAAGAG
AAGAAACTCCCCCTGGGAGCCCTGGGAGGCCCTAATCAGGTGTCCTCCCAGGTGTCCTGG
CCTCAGCTGCTGTATACCTACCAGCTGCTGCACAGCCTGGAGCTGGTGCTGTCCAGGGCT
F2A
GTCAGGGACCTGCTCCTGCTGAGCCTGCCTAGAAGGCCTGGCAGCGCTTGGGACTCCGGC
AGCGGCGTGAAGCAGACCCTGAACTTCGACCTGCTGAAGCTGGCCGGAGACGTGGAGAGC
Mouse CCL19
AACCCTGGCCCATGCATGGCCCCCAGGGTGACCCCTCTGCTGGCCTTCAGCCTGCTGGTG
CTGTGGACCTTCCCTGCCCCTACCCTGGGAGGAGCCAATGACGCCGAGGACTGCTGCCTG
AGCGTGACCCAGAGACCCATCCCCGGCAACATCGTGAAGGCCTTCAGGTACCTGCTGAAC
GAGGACGGCTGCAGAGTGCCTGCCGTGGTGTTCACCACCCTGAGGGGCTACCAGCTGTGT
GCTCCCCCTGACCAGCCTTGGGTGGACAGGATCATCAGGAGGCTGAAGAAGAGCAGCGCC
AAGAACAAGGGCAACAGCACCAGGAGGAGCCCCGTGAGCTGAAAGCTTAAACCAGTTAAC
Stop codon
TGGAAAACGCGTAAAGTCGAC
Sal I

[Figure 16]
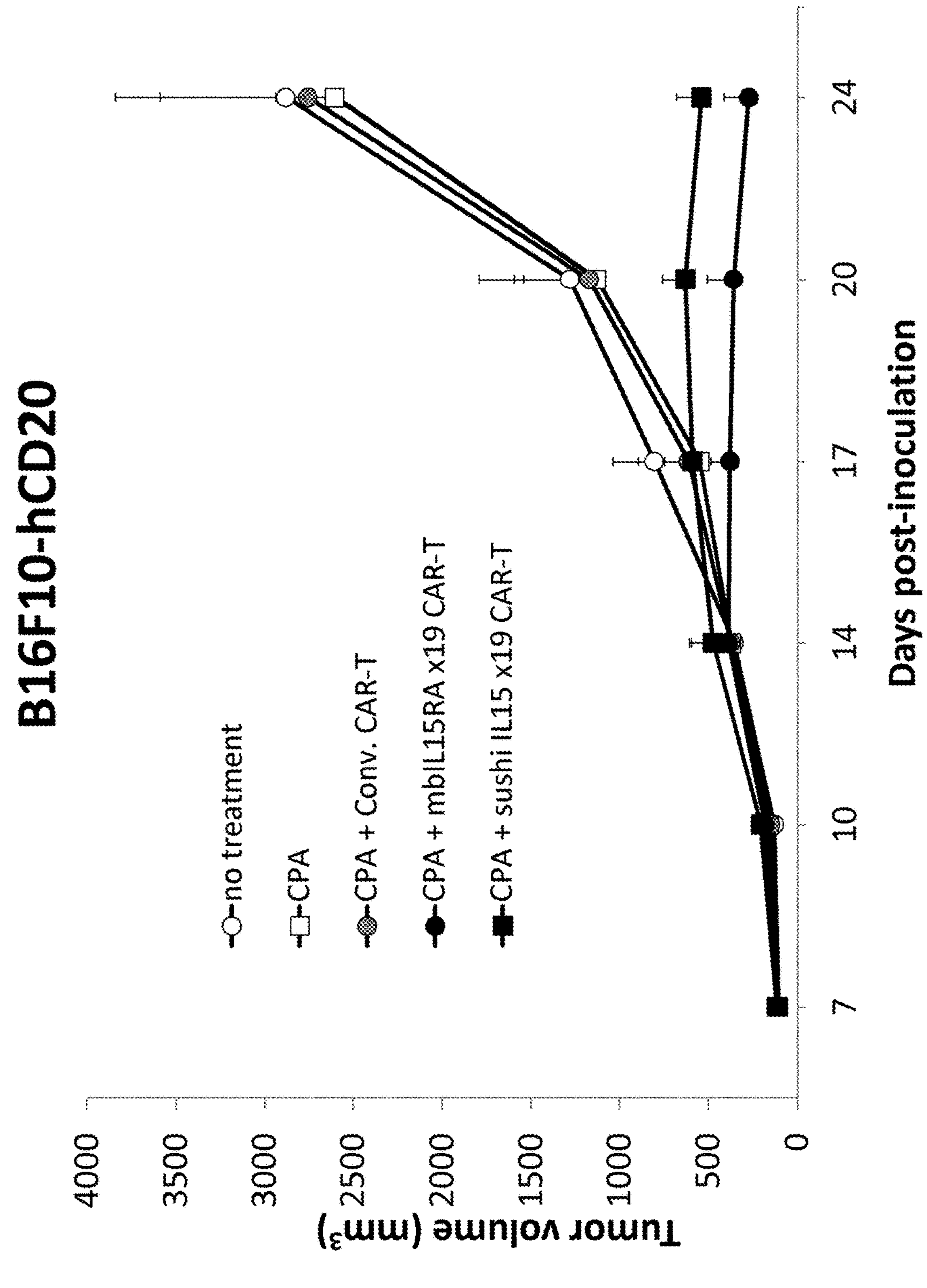

[Figure 17]
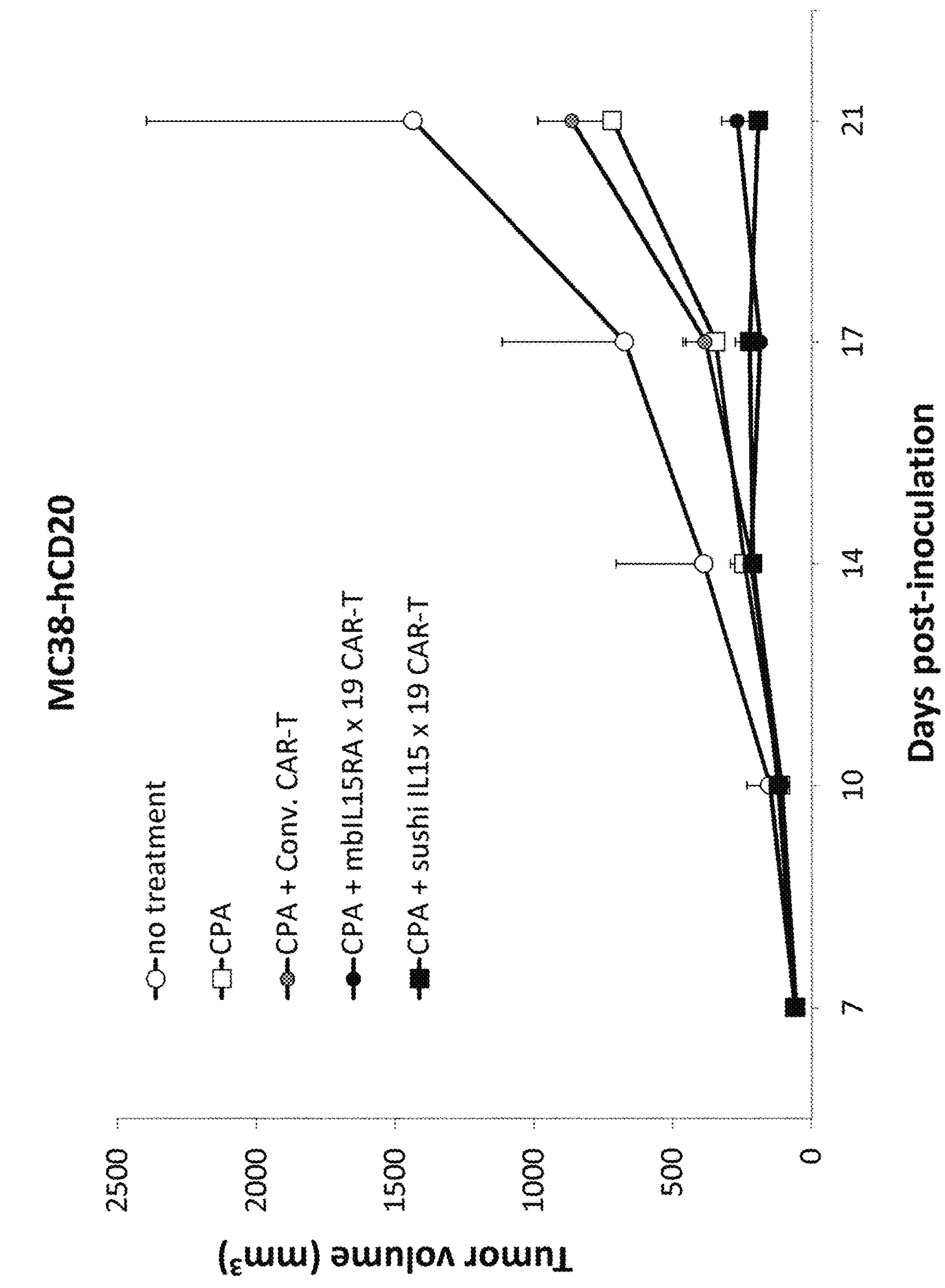

SEQUENCE LISTING

<160> NUMBER OF SEQ ID NOS: 19

<210> SEQ ID NO 1
<211> LENGTH: 1637
<212> TYPE: DNA
<213> ORGANISM: Artificial Sequence

```
<220> FEATURE:
<223> OTHER INFORMATION: DNA segment comprising anti-human CD20 CAR (DNA
      segment #1)
<220> FEATURE:
<221> NAME/KEY: misc_feature
<222> LOCATION: (1)..(6)
<223> OTHER INFORMATION: restriction site (Nco I)
<220> FEATURE:
<221> NAME/KEY: CDS
<222> LOCATION: (3)..(1637)
<223> OTHER INFORMATION: nucleic acid sequence encoding an anti-human
      CD20 scFv, a 3rd TM domain (mouse CD8) and a CP domain (mouse
      CD28_4-1BB_CD3zeta)
<220> FEATURE:
<221> NAME/KEY: misc_feature
<222> LOCATION: (3)..(785)
<223> OTHER INFORMATION: anti-human CD20 scFv
<220> FEATURE:
<221> NAME/KEY: misc_feature
<222> LOCATION: (795)..(1040)
<223> OTHER INFORMATION: transmembrane domain of mouse CD8
<220> FEATURE:
<221> NAME/KEY: misc_feature
<222> LOCATION: (1041)..(1163)
<223> OTHER INFORMATION: cytoplasmic domain of mouse CD28
<220> FEATURE:
<221> NAME/KEY: misc_feature
<222> LOCATION: (1164)..(1298)
<223> OTHER INFORMATION: cytoplasmic domain of mouse 4-1BB
<220> FEATURE:
<221> NAME/KEY: misc_feature
<222> LOCATION: (1299)..(1637)
<223> OTHER INFORMATION: cytoplasmic domain of mouse CD3 zeta
<220> FEATURE:
<221> NAME/KEY: misc_feature
<222> LOCATION: (1337)..(1344)
<223> OTHER INFORMATION: restriction site (Sbf I)

<400> SEQUENCE: 1

cc atg gac tgg acc tgg cgg atc ctg ttc ctg gtg gct gct gct aca        47
   Met Asp Trp Thr Trp Arg Ile Leu Phe Leu Val Ala Ala Ala Thr
   1               5                   10                  15

ggc gcc cac agc cag atc gtg ctg tct cag tct ccc gcc atc ctg tct       95
Gly Ala His Ser Gln Ile Val Leu Ser Gln Ser Pro Ala Ile Leu Ser
                20                  25                  30

gct agc cct ggc gag aaa gtg acc atg acc tgc aga gcc agc agc agc      143
Ala Ser Pro Gly Glu Lys Val Thr Met Thr Cys Arg Ala Ser Ser Ser
            35                  40                  45

gtg tcc tac atc cac tgg ttc cag cag aag ccc ggc agc agc ccc aag      191
Val Ser Tyr Ile His Trp Phe Gln Gln Lys Pro Gly Ser Ser Pro Lys
        50                  55                  60

cct tgg atc tac gcc aca agc aac ctg gcc tct ggc gtg cca gtg cgg      239
Pro Trp Ile Tyr Ala Thr Ser Asn Leu Ala Ser Gly Val Pro Val Arg
    65                  70                  75

ttt agc ggc tct ggc tct ggc acc agc tac agc ctg acc atc agc aga      287
Phe Ser Gly Ser Gly Ser Gly Thr Ser Tyr Ser Leu Thr Ile Ser Arg
80                  85                  90                  95

gtg gaa gcc gag gac gcc gcc acc tac tac tgt cag cag tgg acc agc      335
Val Glu Ala Glu Asp Ala Ala Thr Tyr Tyr Cys Gln Gln Trp Thr Ser
                100                 105                 110

aac ccc ccc aca ttc ggc gga ggc acc aag ctg gaa atc aag ggc gga      383
Asn Pro Pro Thr Phe Gly Gly Gly Thr Lys Leu Glu Ile Lys Gly Gly
            115                 120                 125

ggc gga tct ggc ggc gga gga tct ggg gga ggc ggc tct cag gtg cag      431
Gly Gly Ser Gly Gly Gly Gly Ser Gly Gly Gly Gly Ser Gln Val Gln
        130                 135                 140

ctg cag cag cct ggc gct gag ctc gtg aaa cct ggc gcc tcc gtg aag      479
Leu Gln Gln Pro Gly Ala Glu Leu Val Lys Pro Gly Ala Ser Val Lys
    145                 150                 155
```

-continued

```
atg agc tgc aag gcc agc ggc tac acc ttc aca agc tac aac atg cac      527
Met Ser Cys Lys Ala Ser Gly Tyr Thr Phe Thr Ser Tyr Asn Met His
160                 165                 170                 175

tgg gtc aag cag acc cct ggc aga ggc ctg gaa tgg atc ggc gct atc      575
Trp Val Lys Gln Thr Pro Gly Arg Gly Leu Glu Trp Ile Gly Ala Ile
                180                 185                 190

tac ccc ggc aac ggc gac acc tcc tac aac cag aag ttc aag ggc aag      623
Tyr Pro Gly Asn Gly Asp Thr Ser Tyr Asn Gln Lys Phe Lys Gly Lys
            195                 200                 205

gcc acc ctg acc gcc gac aag agc agc agc aca gcc tac atg cag ctg      671
Ala Thr Leu Thr Ala Asp Lys Ser Ser Ser Thr Ala Tyr Met Gln Leu
        210                 215                 220

tcc tcc ctg acc agc gag gac agc gcc gtg tac tac tgc gcc aga tct      719
Ser Ser Leu Thr Ser Glu Asp Ser Ala Val Tyr Tyr Cys Ala Arg Ser
    225                 230                 235

acc tac tac ggc ggc gac tgg tac ttc aac gtg tgg ggc gct ggc acc      767
Thr Tyr Tyr Gly Gly Asp Trp Tyr Phe Asn Val Trp Gly Ala Gly Thr
240                 245                 250                 255

acc gtg acc gtg tct gct gcg gcc gca gtc gtg cca gtc ctt cag aaa      815
Thr Val Thr Val Ser Ala Ala Ala Ala Val Val Pro Val Leu Gln Lys
                260                 265                 270

gtg aac tct act act acc aag cca gtg ctg cga act ccc tca cct gtg      863
Val Asn Ser Thr Thr Thr Lys Pro Val Leu Arg Thr Pro Ser Pro Val
            275                 280                 285

cac cct acc ggg aca tct cag ccc cag aga cca gaa gat tgt cgg ccc      911
His Pro Thr Gly Thr Ser Gln Pro Gln Arg Pro Glu Asp Cys Arg Pro
        290                 295                 300

cgt ggc tca gtg aag ggg acc gga ttg gac ttc gcc tgt gat att tac      959
Arg Gly Ser Val Lys Gly Thr Gly Leu Asp Phe Ala Cys Asp Ile Tyr
    305                 310                 315

atc tgg gca ccc ttg gcc gga atc tgc gtg gcc cct ctg ctg tcc ttg     1007
Ile Trp Ala Pro Leu Ala Gly Ile Cys Val Ala Pro Leu Leu Ser Leu
320                 325                 330                 335

atc atc act ctc atc tgc tac cac agg agc cga aat agt aga agg aac     1055
Ile Ile Thr Leu Ile Cys Tyr His Arg Ser Arg Asn Ser Arg Arg Asn
                340                 345                 350

aga ctc ctt caa agt gac tac atg aac atg act ccc cgg agg cct ggg     1103
Arg Leu Leu Gln Ser Asp Tyr Met Asn Met Thr Pro Arg Arg Pro Gly
            355                 360                 365

ctc act cga aag cct tac cag ccc tac gcc cct gcc aga gac ttt gca     1151
Leu Thr Arg Lys Pro Tyr Gln Pro Tyr Ala Pro Ala Arg Asp Phe Ala
        370                 375                 380

gcg tac cgc ccc aaa tgg atc agg aaa aaa ttc ccc cac ata ttc aag     1199
Ala Tyr Arg Pro Lys Trp Ile Arg Lys Lys Phe Pro His Ile Phe Lys
    385                 390                 395

caa cca ttt aag aag acc act gga gca gct caa gag gaa gat gct tgt     1247
Gln Pro Phe Lys Lys Thr Thr Gly Ala Ala Gln Glu Glu Asp Ala Cys
400                 405                 410                 415

agc tgc cga tgt cca cag gaa gaa gaa gga gga gga gga ggc tat gag     1295
Ser Cys Arg Cys Pro Gln Glu Glu Glu Gly Gly Gly Gly Gly Tyr Glu
                420                 425                 430

ctg aga gca aaa ttc agc agg agt gca gag act gct gcc aac ctg cag     1343
Leu Arg Ala Lys Phe Ser Arg Ser Ala Glu Thr Ala Ala Asn Leu Gln
            435                 440                 445

gac ccc aac cag ctc tac aat gag ctc aat cta ggg cga aga gag gaa     1391
Asp Pro Asn Gln Leu Tyr Asn Glu Leu Asn Leu Gly Arg Arg Glu Glu
        450                 455                 460

tat gac gtc ttg gag aag aag cgg gct cgg gat cca gag atg gga ggc     1439
Tyr Asp Val Leu Glu Lys Lys Arg Ala Arg Asp Pro Glu Met Gly Gly
```

```
    465                 470                 475

aaa cag cag agg agg agg aac ccc cag gaa ggc gta tac aat gca ctg      1487
Lys Gln Gln Arg Arg Arg Asn Pro Gln Glu Gly Val Tyr Asn Ala Leu
480                 485                 490                 495

cag aaa gac aag atg gca gaa gcc tac agt gag atc ggc aca aaa ggc      1535
Gln Lys Asp Lys Met Ala Glu Ala Tyr Ser Glu Ile Gly Thr Lys Gly
                500                 505                 510

gag agg cgg aga ggc aag ggg cac gat ggc ctt tac cag ggt ctc agc      1583
Glu Arg Arg Arg Gly Lys Gly His Asp Gly Leu Tyr Gln Gly Leu Ser
            515                 520                 525

act gcc acc aag gac acc tat gat gcc ctg cat atg cag acc ctg gcc      1631
Thr Ala Thr Lys Asp Thr Tyr Asp Ala Leu His Met Gln Thr Leu Ala
        530                 535                 540

cct cgc                                                              1637
Pro Arg
    545


<210> SEQ ID NO 2
<211> LENGTH: 545
<212> TYPE: PRT
<213> ORGANISM: Artificial Sequence
<220> FEATURE:
<223> OTHER INFORMATION: Synthetic Construct

<400> SEQUENCE: 2

Met Asp Trp Thr Trp Arg Ile Leu Phe Leu Val Ala Ala Ala Thr Gly
1               5                   10                  15

Ala His Ser Gln Ile Val Leu Ser Gln Ser Pro Ala Ile Leu Ser Ala
            20                  25                  30

Ser Pro Gly Glu Lys Val Thr Met Thr Cys Arg Ala Ser Ser Ser Val
        35                  40                  45

Ser Tyr Ile His Trp Phe Gln Gln Lys Pro Gly Ser Ser Pro Lys Pro
    50                  55                  60

Trp Ile Tyr Ala Thr Ser Asn Leu Ala Ser Gly Val Pro Val Arg Phe
65                  70                  75                  80

Ser Gly Ser Gly Ser Gly Thr Ser Tyr Ser Leu Thr Ile Ser Arg Val
                85                  90                  95

Glu Ala Glu Asp Ala Ala Thr Tyr Tyr Cys Gln Gln Trp Thr Ser Asn
            100                 105                 110

Pro Pro Thr Phe Gly Gly Gly Thr Lys Leu Glu Ile Lys Gly Gly Gly
        115                 120                 125

Gly Ser Gly Gly Gly Gly Ser Gly Gly Gly Gly Ser Gln Val Gln Leu
    130                 135                 140

Gln Gln Pro Gly Ala Glu Leu Val Lys Pro Gly Ala Ser Val Lys Met
145                 150                 155                 160

Ser Cys Lys Ala Ser Gly Tyr Thr Phe Thr Ser Tyr Asn Met His Trp
                165                 170                 175

Val Lys Gln Thr Pro Gly Arg Gly Leu Glu Trp Ile Gly Ala Ile Tyr
            180                 185                 190

Pro Gly Asn Gly Asp Thr Ser Tyr Asn Gln Lys Phe Lys Gly Lys Ala
        195                 200                 205

Thr Leu Thr Ala Asp Lys Ser Ser Ser Thr Ala Tyr Met Gln Leu Ser
    210                 215                 220

Ser Leu Thr Ser Glu Asp Ser Ala Val Tyr Tyr Cys Ala Arg Ser Thr
225                 230                 235                 240

Tyr Tyr Gly Gly Asp Trp Tyr Phe Asn Val Trp Gly Ala Gly Thr Thr
                245                 250                 255
```

```
Val Thr Val Ser Ala Ala Ala Ala Val Val Pro Val Leu Gln Lys Val
            260                 265                 270

Asn Ser Thr Thr Thr Lys Pro Val Leu Arg Thr Pro Ser Pro Val His
        275                 280                 285

Pro Thr Gly Thr Ser Gln Pro Gln Arg Pro Glu Asp Cys Arg Pro Arg
    290                 295                 300

Gly Ser Val Lys Gly Thr Gly Leu Asp Phe Ala Cys Asp Ile Tyr Ile
305                 310                 315                 320

Trp Ala Pro Leu Ala Gly Ile Cys Val Ala Pro Leu Leu Ser Leu Ile
                325                 330                 335

Ile Thr Leu Ile Cys Tyr His Arg Ser Arg Asn Ser Arg Arg Asn Arg
            340                 345                 350

Leu Leu Gln Ser Asp Tyr Met Asn Met Thr Pro Arg Arg Pro Gly Leu
        355                 360                 365

Thr Arg Lys Pro Tyr Gln Pro Tyr Ala Pro Ala Arg Asp Phe Ala Ala
    370                 375                 380

Tyr Arg Pro Lys Trp Ile Arg Lys Lys Phe Pro His Ile Phe Lys Gln
385                 390                 395                 400

Pro Phe Lys Lys Thr Thr Gly Ala Ala Gln Glu Glu Asp Ala Cys Ser
                405                 410                 415

Cys Arg Cys Pro Gln Glu Glu Glu Gly Gly Gly Gly Gly Tyr Glu Leu
            420                 425                 430

Arg Ala Lys Phe Ser Arg Ser Ala Glu Thr Ala Ala Asn Leu Gln Asp
        435                 440                 445

Pro Asn Gln Leu Tyr Asn Glu Leu Asn Leu Gly Arg Arg Glu Glu Tyr
    450                 455                 460

Asp Val Leu Glu Lys Lys Arg Ala Arg Asp Pro Glu Met Gly Gly Lys
465                 470                 475                 480

Gln Gln Arg Arg Arg Asn Pro Gln Glu Gly Val Tyr Asn Ala Leu Gln
                485                 490                 495

Lys Asp Lys Met Ala Glu Ala Tyr Ser Glu Ile Gly Thr Lys Gly Glu
            500                 505                 510

Arg Arg Arg Gly Lys Gly His Asp Gly Leu Tyr Gln Gly Leu Ser Thr
        515                 520                 525

Ala Thr Lys Asp Thr Tyr Asp Ala Leu His Met Gln Thr Leu Ala Pro
    530                 535                 540

Arg
545
```

<210> SEQ ID NO 3
<211> LENGTH: 42
<212> TYPE: DNA
<213> ORGANISM: Artificial Sequence
<220> FEATURE:
<223> OTHER INFORMATION: MCS DNA segment encoding a stop codon and a restriction enzyme site (DNA segment #2)
<220> FEATURE:
<221> NAME/KEY: misc_feature
<222> LOCATION: (1)..(3)
<223> OTHER INFORMATION: stop codon
<220> FEATURE:
<221> NAME/KEY: misc_feature
<222> LOCATION: (38)..(43)
<223> OTHER INFORMATION: restriction site (Sal I)

<400> SEQUENCE: 3

```
tgaaagctta aaccagttaa ctggaaaacg cgtaaagtcg ac                          42
```

<210> SEQ ID NO 4
<211> LENGTH: 1011
<212> TYPE: DNA
<213> ORGANISM: Artificial Sequence
<220> FEATURE:
<223> OTHER INFORMATION: DNA segment of IL15LSP_F2A_CCL19 (DNA segment #3)
<220> FEATURE:
<221> NAME/KEY: CDS
<222> LOCATION: (7)..(969)
<223> OTHER INFORMATION: nucleic acid sequence encoding 1st F2A; a fusion protein "IL15LSP" comprising mouse IL-15 LSP and mouse IL-15; 2nd F2A; and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(168)
<223> OTHER INFORMATION: mouse IL-15 LSP
<220> FEATURE:
<221> NAME/KEY: misc_feature
<222> LOCATION: (169)..(567)
<223> OTHER INFORMATION: mouse IL-15
<220> FEATURE:
<221> NAME/KEY: misc_feature
<222> LOCATION: (568)..(642)
<223> OTHER INFORMATION: mouse F2A
<220> FEATURE:
<221> NAME/KEY: misc_feature
<222> LOCATION: (646)..(969)
<223> OTHER INFORMATION: mouse CCL19
<220> FEATURE:
<221> NAME/KEY: misc_feature
<222> LOCATION: (970)..(972)
<223> OTHER INFORMATION: stop codon
<220> FEATURE:
<221> NAME/KEY: misc_feature
<222> LOCATION: (1006)..(1011)
<223> OTHER INFORMATION: restriction site (Sal I)

<400> SEQUENCE: 4

```
gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg aag atc ctg aag       96
Leu Ala Gly Asp Val Glu Ser Asn Pro Gly Pro Met Lys Ile Leu Lys
15                  20                  25                  30

ccc tac atg agg aac acc agc atc tcc tgt tac ctc tgt ttc ctg ctg      144
Pro Tyr Met Arg Asn Thr Ser Ile Ser Cys Tyr Leu Cys Phe Leu Leu
                35                  40                  45

aac agc cac ttc ctg acc gag gcc ggc atc cac gtg ttc atc ctg ggc      192
Asn Ser His Phe Leu Thr Glu Ala Gly Ile His Val Phe Ile Leu Gly
            50                  55                  60

tgc gtg tcc gtg ggc ctg cct aag acc gag gcc aac tgg atc gac gtg      240
Cys Val Ser Val Gly Leu Pro Lys Thr Glu Ala Asn Trp Ile Asp Val
        65                  70                  75

aga tac gac ctg gag aag atc gag agc ctg atc cag agc atc cac atc      288
Arg Tyr Asp Leu Glu Lys Ile Glu Ser Leu Ile Gln Ser Ile His Ile
    80                  85                  90

gac acc aca ctg tac acc gac agc gac ttc cac ccc agc tgc aag gtg      336
Asp Thr Thr Leu Tyr Thr Asp Ser Asp Phe His Pro Ser Cys Lys Val
95                  100                 105                 110

acc gcc atg aac tgc ttt ctg ctg gag ctg cag gtg atc ctg cac gag      384
Thr Ala Met Asn Cys Phe Leu Leu Glu Leu Gln Val Ile Leu His Glu
                115                 120                 125

tac agc aac atg acc ctg aac gag acc gtg aga aac gtg ctg tac ctg      432
Tyr Ser Asn Met Thr Leu Asn Glu Thr Val Arg Asn Val Leu Tyr Leu
```

-continued

```
            130                 135                 140

gcc aac tcc acc ctg agc agc aac aag aac gtg gcc gag agc ggc tgc      480
Ala Asn Ser Thr Leu Ser Ser Asn Lys Asn Val Ala Glu Ser Gly Cys
        145                 150                 155

aag gag tgc gag gag ctc gag gag aaa acc ttc acc gag ttc ctg cag      528
Lys Glu Cys Glu Glu Leu Glu Glu Lys Thr Phe Thr Glu Phe Leu Gln
    160                 165                 170

agc ttc atc agg atc gtc cag atg ttc atc aac acc agc ggc agc ggc      576
Ser Phe Ile Arg Ile Val Gln Met Phe Ile Asn Thr Ser Gly Ser Gly
175                 180                 185                 190

gtg aag cag acc ctg aac ttc gac ctg ctg aag ctg gcc gga gac gtg      624
Val Lys Gln Thr Leu Asn Phe Asp Leu Leu Lys Leu Ala Gly Asp Val
                195                 200                 205

gag agc aac cct ggc cca tgc atg gcc ccc agg gtg acc cct ctg ctg      672
Glu Ser Asn Pro Gly Pro Cys Met Ala Pro Arg Val Thr Pro Leu Leu
            210                 215                 220

gcc ttc agc ctg ctg gtg ctg tgg acc ttc cct gcc cct acc ctg gga      720
Ala Phe Ser Leu Leu Val Leu Trp Thr Phe Pro Ala Pro Thr Leu Gly
        225                 230                 235

gga gcc aat gac gcc gag gac tgc tgc ctg agc gtg acc cag aga ccc      768
Gly Ala Asn Asp Ala Glu Asp Cys Cys Leu Ser Val Thr Gln Arg Pro
    240                 245                 250

atc ccc ggc aac atc gtg aag gcc ttc agg tac ctg ctg aac gag gac      816
Ile Pro Gly Asn Ile Val Lys Ala Phe Arg Tyr Leu Leu Asn Glu Asp
255                 260                 265                 270

ggc tgc aga gtg cct gcc gtg gtg ttc acc acc ctg agg ggc tac cag      864
Gly Cys Arg Val Pro Ala Val Val Phe Thr Thr Leu Arg Gly Tyr Gln
                275                 280                 285

ctg tgt gct ccc cct gac cag cct tgg gtg gac agg atc atc agg agg      912
Leu Cys Ala Pro Pro Asp Gln Pro Trp Val Asp Arg Ile Ile Arg Arg
            290                 295                 300

ctg aag aag agc agc gcc aag aac aag ggc aac agc acc agg agg agc      960
Leu Lys Lys Ser Ser Ala Lys Asn Lys Gly Asn Ser Thr Arg Arg Ser
        305                 310                 315

ccc gtg agc tgaaagctta aaccagttaa ctggaaaacg cgtaaagtcg ac          1011
Pro Val Ser
    320


<210> SEQ ID NO 5
<211> LENGTH: 321
<212> TYPE: PRT
<213> ORGANISM: Artificial Sequence
<220> FEATURE:
<223> OTHER INFORMATION: Synthetic Construct

<400> SEQUENCE: 5

Gly Ser Gly Val Lys Gln Thr Leu Asn Phe Asp Leu Leu Lys Leu Ala
1               5                   10                  15

Gly Asp Val Glu Ser Asn Pro Gly Pro Met Lys Ile Leu Lys Pro Tyr
            20                  25                  30

Met Arg Asn Thr Ser Ile Ser Cys Tyr Leu Cys Phe Leu Leu Asn Ser
        35                  40                  45

His Phe Leu Thr Glu Ala Gly Ile His Val Phe Ile Leu Gly Cys Val
    50                  55                  60

Ser Val Gly Leu Pro Lys Thr Glu Ala Asn Trp Ile Asp Val Arg Tyr
65                  70                  75                  80

Asp Leu Glu Lys Ile Glu Ser Leu Ile Gln Ser Ile His Ile Asp Thr
                85                  90                  95

Thr Leu Tyr Thr Asp Ser Asp Phe His Pro Ser Cys Lys Val Thr Ala
```

```
            100                 105                 110

Met Asn Cys Phe Leu Leu Glu Leu Gln Val Ile Leu His Glu Tyr Ser
        115                 120                 125

Asn Met Thr Leu Asn Glu Thr Val Arg Asn Val Leu Tyr Leu Ala Asn
    130                 135                 140

Ser Thr Leu Ser Ser Asn Lys Asn Val Ala Glu Ser Gly Cys Lys Glu
145                 150                 155                 160

Cys Glu Glu Leu Glu Glu Lys Thr Phe Thr Glu Phe Leu Gln Ser Phe
                165                 170                 175

Ile Arg Ile Val Gln Met Phe Ile Asn Thr Ser Gly Ser Gly Val Lys
            180                 185                 190

Gln Thr Leu Asn Phe Asp Leu Leu Lys Leu Ala Gly Asp Val Glu Ser
        195                 200                 205

Asn Pro Gly Pro Cys Met Ala Pro Arg Val Thr Pro Leu Leu Ala Phe
    210                 215                 220

Ser Leu Leu Val Leu Trp Thr Phe Pro Ala Pro Thr Leu Gly Gly Ala
225                 230                 235                 240

Asn Asp Ala Glu Asp Cys Cys Leu Ser Val Thr Gln Arg Pro Ile Pro
                245                 250                 255

Gly Asn Ile Val Lys Ala Phe Arg Tyr Leu Leu Asn Glu Asp Gly Cys
            260                 265                 270

Arg Val Pro Ala Val Val Phe Thr Thr Leu Arg Gly Tyr Gln Leu Cys
        275                 280                 285

Ala Pro Pro Asp Gln Pro Trp Val Asp Arg Ile Ile Arg Arg Leu Lys
    290                 295                 300

Lys Ser Ser Ala Lys Asn Lys Gly Asn Ser Thr Arg Arg Ser Pro Val
305                 310                 315                 320

Ser


<210> SEQ ID NO 6
<211> LENGTH: 1581
<212> TYPE: DNA
<213> ORGANISM: Artificial Sequence
<220> FEATURE:
<223> OTHER INFORMATION: DNA segment of sIL15RA_F2A_CCL19 (DNA segment
      #4)
<220> FEATURE:
<221> NAME/KEY: CDS
<222> LOCATION: (7)..(1539)
<223> OTHER INFORMATION: nucleic acid sequence encoding 1st F2A; a
      fusion protein "sIL15RA" comprising IL-2SP, IL-15, a linker and
      IL-15Ra extracellular domain; 2nd F2A; and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(141)
<223> OTHER INFORMATION: mouse IL-2 SP
<220> FEATURE:
<221> NAME/KEY: misc_feature
<222> LOCATION: (142)..(540)
<223> OTHER INFORMATION: mouse IL-15
<220> FEATURE:
<221> NAME/KEY: misc_feature
<222> LOCATION: (541)..(618)
<223> OTHER INFORMATION: linker
<220> FEATURE:
<221> NAME/KEY: misc_feature
<222> LOCATION: (619)..(1137)
<223> OTHER INFORMATION: mouse IL-15Ra extracellular domain
<220> FEATURE:
<221> NAME/KEY: misc_feature
```

```
<222> LOCATION: (1138)..(1212)
<223> OTHER INFORMATION: F2A
<220> FEATURE:
<221> NAME/KEY: misc_feature
<222> LOCATION: (1216)..(1539)
<223> OTHER INFORMATION: mouse CCL19
<220> FEATURE:
<221> NAME/KEY: misc_feature
<222> LOCATION: (1540)..(1542)
<223> OTHER INFORMATION: stop codon
<220> FEATURE:
<221> NAME/KEY: misc_feature
<222> LOCATION: (1576)..(1581)
<223> OTHER INFORMATION: restriction site (Sal I)

<400> SEQUENCE: 6

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg tat tcc atg cag       96
Leu Ala Gly Asp Val Glu Ser Asn Pro Gly Pro Met Tyr Ser Met Gln
15                  20                  25                  30

ctg gcc agc tgt gtg acc ctg aca ctg gtg ctg ctg gtg aac agc ggc      144
Leu Ala Ser Cys Val Thr Leu Thr Leu Val Leu Leu Val Asn Ser Gly
                35                  40                  45

atc cac gtg ttc att ctg gga tgc gtc tcc gtg ggc ctc ccc aag acc      192
Ile His Val Phe Ile Leu Gly Cys Val Ser Val Gly Leu Pro Lys Thr
            50                  55                  60

gag gct aac tgg atc gac gtc agg tac gac ctg gag aag atc gaa agc      240
Glu Ala Asn Trp Ile Asp Val Arg Tyr Asp Leu Glu Lys Ile Glu Ser
        65                  70                  75

ctg atc cag tcc atc cac atc gat aca acc ctg tac aca gat tcc gac      288
Leu Ile Gln Ser Ile His Ile Asp Thr Thr Leu Tyr Thr Asp Ser Asp
    80                  85                  90

ttc cac ccc tcc tgt aag gtc acc gcc atg aac tgc ttc ctc ctg gaa      336
Phe His Pro Ser Cys Lys Val Thr Ala Met Asn Cys Phe Leu Leu Glu
95                  100                 105                 110

ctc cag gtc atc ctg cac gag tac tcc aac atg acc ctg aac gaa acc      384
Leu Gln Val Ile Leu His Glu Tyr Ser Asn Met Thr Leu Asn Glu Thr
                115                 120                 125

gtg agg aat gtg ctg tac ctc gcc aac tcc aca ctg agc tcc aat aag      432
Val Arg Asn Val Leu Tyr Leu Ala Asn Ser Thr Leu Ser Ser Asn Lys
            130                 135                 140

aac gtg gct gag agc ggc tgc aag gag tgt gag gag ctg gaa gag aag      480
Asn Val Ala Glu Ser Gly Cys Lys Glu Cys Glu Glu Leu Glu Glu Lys
        145                 150                 155

acc ttc acc gag ttc ctg cag agc ttc atc agg atc gtg cag atg ttc      528
Thr Phe Thr Glu Phe Leu Gln Ser Phe Ile Arg Ile Val Gln Met Phe
    160                 165                 170

atc aac aca agc tcc ggc gga gga tcc gga gga gga gga agc gga ggc      576
Ile Asn Thr Ser Ser Gly Gly Gly Ser Gly Gly Gly Gly Ser Gly Gly
175                 180                 185                 190

ggc ggc tcc gga ggc gga gga agc gga gga gga agc ctg caa gga acc      624
Gly Gly Ser Gly Gly Gly Gly Ser Gly Gly Gly Ser Leu Gln Gly Thr
                195                 200                 205

acc tgt ccc cct ccc gtg tcc atc gag cac gcc gac atc agg gtg aag      672
Thr Cys Pro Pro Pro Val Ser Ile Glu His Ala Asp Ile Arg Val Lys
            210                 215                 220

aac tac tcc gtc aac agc agg gaa agg tac gtg tgc aac tcc ggc ttt      720
Asn Tyr Ser Val Asn Ser Arg Glu Arg Tyr Val Cys Asn Ser Gly Phe
        225                 230                 235

aag agg aag gcc ggc acc agc acc ctc atc gag tgc gtg atc aac aag      768
Lys Arg Lys Ala Gly Thr Ser Thr Leu Ile Glu Cys Val Ile Asn Lys
```

```
    240                 245                 250

aac aca aac gtg gcc cac tgg acc acc ccc agc ctg aag tgt att aga      816
Asn Thr Asn Val Ala His Trp Thr Thr Pro Ser Leu Lys Cys Ile Arg
255                 260                 265                 270

gac ccc agc ctg gct cat tac agc ccc gtg ccc aca gtg gtg aca ccc      864
Asp Pro Ser Leu Ala His Tyr Ser Pro Val Pro Thr Val Val Thr Pro
                275                 280                 285

aag gtg aca agc cag cct gag agc cct agc cct agc gcc aaa gag ccc      912
Lys Val Thr Ser Gln Pro Glu Ser Pro Ser Pro Ser Ala Lys Glu Pro
            290                 295                 300

gag gcc ttt tcc ccc aag tcc gac acc gcc atg acc acc gag aca gcc      960
Glu Ala Phe Ser Pro Lys Ser Asp Thr Ala Met Thr Thr Glu Thr Ala
        305                 310                 315

atc atg cct ggc agc aga ctg acc cct agc cag acc aca tcc gct ggc     1008
Ile Met Pro Gly Ser Arg Leu Thr Pro Ser Gln Thr Thr Ser Ala Gly
    320                 325                 330

acc aca ggc acc ggc tcc cac aag agc tcc aga gcc cct agc ctg gct     1056
Thr Thr Gly Thr Gly Ser His Lys Ser Ser Arg Ala Pro Ser Leu Ala
335                 340                 345                 350

gcc aca atg aca ctg gaa cct acc gcc tcc acc agc ctc aga atc aca     1104
Ala Thr Met Thr Leu Glu Pro Thr Ala Ser Thr Ser Leu Arg Ile Thr
                355                 360                 365

gag atc tcc ccc cac agc agc aag atg acc aag ggc agc ggc gtg aag     1152
Glu Ile Ser Pro His Ser Ser Lys Met Thr Lys Gly Ser Gly Val Lys
            370                 375                 380

cag acc ctg aac ttc gac ctg ctg aag ctg gcc gga gac gtg gag agc     1200
Gln Thr Leu Asn Phe Asp Leu Leu Lys Leu Ala Gly Asp Val Glu Ser
        385                 390                 395

aac cct ggc cca tgc atg gcc ccc agg gtg acc cct ctg ctg gcc ttc     1248
Asn Pro Gly Pro Cys Met Ala Pro Arg Val Thr Pro Leu Leu Ala Phe
    400                 405                 410

agc ctg ctg gtg ctg tgg acc ttc cct gcc cct acc ctg gga gga gcc     1296
Ser Leu Leu Val Leu Trp Thr Phe Pro Ala Pro Thr Leu Gly Gly Ala
415                 420                 425                 430

aat gac gcc gag gac tgc tgc ctg agc gtg acc cag aga ccc atc ccc     1344
Asn Asp Ala Glu Asp Cys Cys Leu Ser Val Thr Gln Arg Pro Ile Pro
                435                 440                 445

ggc aac atc gtg aag gcc ttc agg tac ctg ctg aac gag gac ggc tgc     1392
Gly Asn Ile Val Lys Ala Phe Arg Tyr Leu Leu Asn Glu Asp Gly Cys
            450                 455                 460

aga gtg cct gcc gtg gtg ttc acc acc ctg agg ggc tac cag ctg tgt     1440
Arg Val Pro Ala Val Val Phe Thr Thr Leu Arg Gly Tyr Gln Leu Cys
        465                 470                 475

gct ccc cct gac cag cct tgg gtg gac agg atc atc agg agg ctg aag     1488
Ala Pro Pro Asp Gln Pro Trp Val Asp Arg Ile Ile Arg Arg Leu Lys
    480                 485                 490

aag agc agc gcc aag aac aag ggc aac agc acc agg agg agc ccc gtg     1536
Lys Ser Ser Ala Lys Asn Lys Gly Asn Ser Thr Arg Arg Ser Pro Val
495                 500                 505                 510

agc tgaaagctta aaccagttaa ctggaaaacg cgtaaagtcg ac                  1581
Ser
```

<210> SEQ ID NO 7
<211> LENGTH: 511
<212> TYPE: PRT
<213> ORGANISM: Artificial Sequence
<220> FEATURE:
<223> OTHER INFORMATION: Synthetic Construct

<400> SEQUENCE: 7

-continued

```
Gly Ser Gly Val Lys Gln Thr Leu Asn Phe Asp Leu Leu Lys Leu Ala
1               5                   10                  15

Gly Asp Val Glu Ser Asn Pro Gly Pro Met Tyr Ser Met Gln Leu Ala
            20                  25                  30

Ser Cys Val Thr Leu Thr Leu Val Leu Leu Val Asn Ser Gly Ile His
        35                  40                  45

Val Phe Ile Leu Gly Cys Val Ser Val Gly Leu Pro Lys Thr Glu Ala
    50                  55                  60

Asn Trp Ile Asp Val Arg Tyr Asp Leu Glu Lys Ile Glu Ser Leu Ile
65                  70                  75                  80

Gln Ser Ile His Ile Asp Thr Thr Leu Tyr Thr Asp Ser Asp Phe His
                85                  90                  95

Pro Ser Cys Lys Val Thr Ala Met Asn Cys Phe Leu Leu Glu Leu Gln
            100                 105                 110

Val Ile Leu His Glu Tyr Ser Asn Met Thr Leu Asn Glu Thr Val Arg
        115                 120                 125

Asn Val Leu Tyr Leu Ala Asn Ser Thr Leu Ser Ser Asn Lys Asn Val
    130                 135                 140

Ala Glu Ser Gly Cys Lys Glu Cys Glu Glu Leu Glu Glu Lys Thr Phe
145                 150                 155                 160

Thr Glu Phe Leu Gln Ser Phe Ile Arg Ile Val Gln Met Phe Ile Asn
                165                 170                 175

Thr Ser Ser Gly Gly Gly Ser Gly Gly Gly Gly Ser Gly Gly Gly Gly
            180                 185                 190

Ser Gly Gly Gly Gly Ser Gly Gly Gly Ser Leu Gln Gly Thr Thr Cys
        195                 200                 205

Pro Pro Pro Val Ser Ile Glu His Ala Asp Ile Arg Val Lys Asn Tyr
    210                 215                 220

Ser Val Asn Ser Arg Glu Arg Tyr Val Cys Asn Ser Gly Phe Lys Arg
225                 230                 235                 240

Lys Ala Gly Thr Ser Thr Leu Ile Glu Cys Val Ile Asn Lys Asn Thr
                245                 250                 255

Asn Val Ala His Trp Thr Thr Pro Ser Leu Lys Cys Ile Arg Asp Pro
            260                 265                 270

Ser Leu Ala His Tyr Ser Pro Val Pro Thr Val Val Thr Pro Lys Val
        275                 280                 285

Thr Ser Gln Pro Glu Ser Pro Ser Pro Ser Ala Lys Glu Pro Glu Ala
    290                 295                 300

Phe Ser Pro Lys Ser Asp Thr Ala Met Thr Thr Glu Thr Ala Ile Met
305                 310                 315                 320

Pro Gly Ser Arg Leu Thr Pro Ser Gln Thr Thr Ser Ala Gly Thr Thr
                325                 330                 335

Gly Thr Gly Ser His Lys Ser Ser Arg Ala Pro Ser Leu Ala Ala Thr
            340                 345                 350

Met Thr Leu Glu Pro Thr Ala Ser Thr Ser Leu Arg Ile Thr Glu Ile
        355                 360                 365

Ser Pro His Ser Ser Lys Met Thr Lys Gly Ser Gly Val Lys Gln Thr
    370                 375                 380

Leu Asn Phe Asp Leu Leu Lys Leu Ala Gly Asp Val Glu Ser Asn Pro
385                 390                 395                 400

Gly Pro Cys Met Ala Pro Arg Val Thr Pro Leu Leu Ala Phe Ser Leu
                405                 410                 415

Leu Val Leu Trp Thr Phe Pro Ala Pro Thr Leu Gly Gly Ala Asn Asp
```

```
           420                 425                 430

Ala Glu Asp Cys Cys Leu Ser Val Thr Gln Arg Pro Ile Pro Gly Asn
        435                 440                 445

Ile Val Lys Ala Phe Arg Tyr Leu Leu Asn Glu Asp Gly Cys Arg Val
    450                 455                 460

Pro Ala Val Val Phe Thr Thr Leu Arg Gly Tyr Gln Leu Cys Ala Pro
465                 470                 475                 480

Pro Asp Gln Pro Trp Val Asp Arg Ile Ile Arg Arg Leu Lys Lys Ser
                485                 490                 495

Ser Ala Lys Asn Lys Gly Asn Ser Thr Arg Arg Ser Pro Val Ser
            500                 505                 510


<210> SEQ ID NO 8
<211> LENGTH: 1755
<212> TYPE: DNA
<213> ORGANISM: Artificial Sequence
<220> FEATURE:
<223> OTHER INFORMATION: DNA segment of mbIL15RA_F2A_CCL19 (DNA segment
      #5)
<220> FEATURE:
<221> NAME/KEY: CDS
<222> LOCATION: (7)..(1713)
<223> OTHER INFORMATION: nucleic acid sequence encoding 1st F2A; a
      fusion protein "mbIL15RA" comprising IL-2 SP, IL-15, a linker and
      IL-15Ra; 2nd F2A; and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(141)
<223> OTHER INFORMATION: mouse IL-2 SP
<220> FEATURE:
<221> NAME/KEY: misc_feature
<222> LOCATION: (142)..(540)
<223> OTHER INFORMATION: mouse IL-15
<220> FEATURE:
<221> NAME/KEY: misc_feature
<222> LOCATION: (541)..(618)
<223> OTHER INFORMATION: linker
<220> FEATURE:
<221> NAME/KEY: misc_feature
<222> LOCATION: (619)..(1311)
<223> OTHER INFORMATION: mouse IL-15Ra (full length)
<220> FEATURE:
<221> NAME/KEY: misc_feature
<222> LOCATION: (1312)..(1386)
<223> OTHER INFORMATION: F2A peptide
<220> FEATURE:
<221> NAME/KEY: misc_feature
<222> LOCATION: (1390)..(1713)
<223> OTHER INFORMATION: mouse CCL19
<220> FEATURE:
<221> NAME/KEY: misc_feature
<222> LOCATION: (1714)..(1716)
<223> OTHER INFORMATION: stop codon
<220> FEATURE:
<221> NAME/KEY: misc_feature
<222> LOCATION: (1750)..(1755)
<223> OTHER INFORMATION: restriction site (Sal I)

<400> SEQUENCE: 8

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg tat tcc atg cag       96
Leu Ala Gly Asp Val Glu Ser Asn Pro Gly Pro Met Tyr Ser Met Gln
15                  20                  25                  30

ctg gcc agc tgt gtg acc ctg aca ctg gtg ctg ctg gtg aac agc ggc      144
```

-continued

```
Leu Ala Ser Cys Val Thr Leu Thr Leu Val Leu Leu Val Asn Ser Gly
            35                  40                  45

atc cac gtg ttc att ctg gga tgc gtc tcc gtg ggc ctc ccc aag acc      192
Ile His Val Phe Ile Leu Gly Cys Val Ser Val Gly Leu Pro Lys Thr
            50                  55                  60

gag gct aac tgg atc gac gtc agg tac gac ctg gag aag atc gaa agc      240
Glu Ala Asn Trp Ile Asp Val Arg Tyr Asp Leu Glu Lys Ile Glu Ser
        65                  70                  75

ctg atc cag tcc atc cac atc gat aca acc ctg tac aca gat tcc gac      288
Leu Ile Gln Ser Ile His Ile Asp Thr Thr Leu Tyr Thr Asp Ser Asp
    80                  85                  90

ttc cac ccc tcc tgt aag gtc acc gcc atg aac tgc ttc ctc ctg gaa      336
Phe His Pro Ser Cys Lys Val Thr Ala Met Asn Cys Phe Leu Leu Glu
95                  100                 105                 110

ctc cag gtc atc ctg cac gag tac tcc aac atg acc ctg aac gaa acc      384
Leu Gln Val Ile Leu His Glu Tyr Ser Asn Met Thr Leu Asn Glu Thr
            115                 120                 125

gtg agg aat gtg ctg tac ctc gcc aac tcc aca ctg agc tcc aat aag      432
Val Arg Asn Val Leu Tyr Leu Ala Asn Ser Thr Leu Ser Ser Asn Lys
            130                 135                 140

aac gtg gct gag agc ggc tgc aag gag tgt gag gag ctg gaa gag aag      480
Asn Val Ala Glu Ser Gly Cys Lys Glu Cys Glu Glu Leu Glu Glu Lys
        145                 150                 155

acc ttc acc gag ttc ctg cag agc ttc atc agg atc gtg cag atg ttc      528
Thr Phe Thr Glu Phe Leu Gln Ser Phe Ile Arg Ile Val Gln Met Phe
    160                 165                 170

atc aac aca agc tcc ggc gga gga tcc gga gga gga gga agc gga ggc      576
Ile Asn Thr Ser Ser Gly Gly Gly Ser Gly Gly Gly Gly Ser Gly Gly
175                 180                 185                 190

ggc ggc tcc gga ggc gga gga agc gga gga gga agc ctg caa gga acc      624
Gly Gly Ser Gly Gly Gly Gly Ser Gly Gly Gly Ser Leu Gln Gly Thr
            195                 200                 205

acc tgt ccc cct ccc gtg tcc atc gag cac gcc gac atc agg gtg aag      672
Thr Cys Pro Pro Pro Val Ser Ile Glu His Ala Asp Ile Arg Val Lys
            210                 215                 220

aac tac tcc gtc aac agc agg gaa agg tac gtg tgc aac tcc ggc ttt      720
Asn Tyr Ser Val Asn Ser Arg Glu Arg Tyr Val Cys Asn Ser Gly Phe
        225                 230                 235

aag agg aag gcc ggc acc agc acc ctc atc gag tgc gtg atc aac aag      768
Lys Arg Lys Ala Gly Thr Ser Thr Leu Ile Glu Cys Val Ile Asn Lys
    240                 245                 250

aac aca aac gtg gcc cac tgg acc acc ccc agc ctg aag tgt att aga      816
Asn Thr Asn Val Ala His Trp Thr Thr Pro Ser Leu Lys Cys Ile Arg
255                 260                 265                 270

gac ccc agc ctg gct cat tac agc ccc gtg ccc aca gtg gtg aca ccc      864
Asp Pro Ser Leu Ala His Tyr Ser Pro Val Pro Thr Val Val Thr Pro
            275                 280                 285

aag gtg aca agc cag cct gag agc cct agc cct agc gcc aaa gag ccc      912
Lys Val Thr Ser Gln Pro Glu Ser Pro Ser Pro Ser Ala Lys Glu Pro
            290                 295                 300

gag gcc ttt tcc ccc aag tcc gac acc gcc atg acc acc gag aca gcc      960
Glu Ala Phe Ser Pro Lys Ser Asp Thr Ala Met Thr Thr Glu Thr Ala
        305                 310                 315

atc atg cct ggc agc aga ctg acc cct agc cag acc aca tcc gct ggc     1008
Ile Met Pro Gly Ser Arg Leu Thr Pro Ser Gln Thr Thr Ser Ala Gly
    320                 325                 330

acc aca ggc acc ggc tcc cac aag agc tcc aga gcc cct agc ctg gct     1056
Thr Thr Gly Thr Gly Ser His Lys Ser Ser Arg Ala Pro Ser Leu Ala
335                 340                 345                 350
```

```
gcc aca atg aca ctg gaa cct acc gcc tcc acc agc ctc aga atc aca     1104
Ala Thr Met Thr Leu Glu Pro Thr Ala Ser Thr Ser Leu Arg Ile Thr
                355                 360                 365

gag atc tcc ccc cac agc agc aag atg acc aag gtg gcc atc tcc acc     1152
Glu Ile Ser Pro His Ser Ser Lys Met Thr Lys Val Ala Ile Ser Thr
            370                 375                 380

tcc gtg ctg ctg gtg gga gcc ggc gtg gtc atg gcc ttt ctg gcc tgg     1200
Ser Val Leu Leu Val Gly Ala Gly Val Val Met Ala Phe Leu Ala Trp
        385                 390                 395

tac atc aag tcc agg cag cct agc caa cct tgc agg gtg gag gtg gaa     1248
Tyr Ile Lys Ser Arg Gln Pro Ser Gln Pro Cys Arg Val Glu Val Glu
    400                 405                 410

act atg gaa acc gtg ccc atg acc gtg agg gcc agc tcc aag gag gat     1296
Thr Met Glu Thr Val Pro Met Thr Val Arg Ala Ser Ser Lys Glu Asp
415                 420                 425                 430

gaa gac acc ggc gcc ggc agc ggc gtg aag cag acc ctg aac ttc gac     1344
Glu Asp Thr Gly Ala Gly Ser Gly Val Lys Gln Thr Leu Asn Phe Asp
                435                 440                 445

ctg ctg aag ctg gcc gga gac gtg gag agc aac cct ggc cca tgc atg     1392
Leu Leu Lys Leu Ala Gly Asp Val Glu Ser Asn Pro Gly Pro Cys Met
            450                 455                 460

gcc ccc agg gtg acc cct ctg ctg gcc ttc agc ctg ctg gtg ctg tgg     1440
Ala Pro Arg Val Thr Pro Leu Leu Ala Phe Ser Leu Leu Val Leu Trp
        465                 470                 475

acc ttc cct gcc cct acc ctg gga gga gcc aat gac gcc gag gac tgc     1488
Thr Phe Pro Ala Pro Thr Leu Gly Gly Ala Asn Asp Ala Glu Asp Cys
    480                 485                 490

tgc ctg agc gtg acc cag aga ccc atc ccc ggc aac atc gtg aag gcc     1536
Cys Leu Ser Val Thr Gln Arg Pro Ile Pro Gly Asn Ile Val Lys Ala
495                 500                 505                 510

ttc agg tac ctg ctg aac gag gac ggc tgc aga gtg cct gcc gtg gtg     1584
Phe Arg Tyr Leu Leu Asn Glu Asp Gly Cys Arg Val Pro Ala Val Val
                515                 520                 525

ttc acc acc ctg agg ggc tac cag ctg tgt gct ccc cct gac cag cct     1632
Phe Thr Thr Leu Arg Gly Tyr Gln Leu Cys Ala Pro Pro Asp Gln Pro
            530                 535                 540

tgg gtg gac agg atc atc agg agg ctg aag aag agc agc gcc aag aac     1680
Trp Val Asp Arg Ile Ile Arg Arg Leu Lys Lys Ser Ser Ala Lys Asn
        545                 550                 555

aag ggc aac agc acc agg agg agc ccc gtg agc tgaaagctta aaccagttaa   1733
Lys Gly Asn Ser Thr Arg Arg Ser Pro Val Ser
    560                 565

ctggaaaacg cgtaaagtcg ac                                            1755


<210> SEQ ID NO 9
<211> LENGTH: 569
<212> TYPE: PRT
<213> ORGANISM: Artificial Sequence
<220> FEATURE:
<223> OTHER INFORMATION: Synthetic Construct

<400> SEQUENCE: 9

Gly Ser Gly Val Lys Gln Thr Leu Asn Phe Asp Leu Leu Lys Leu Ala
1               5                   10                  15

Gly Asp Val Glu Ser Asn Pro Gly Pro Met Tyr Ser Met Gln Leu Ala
            20                  25                  30

Ser Cys Val Thr Leu Thr Leu Val Leu Leu Val Asn Ser Gly Ile His
        35                  40                  45

Val Phe Ile Leu Gly Cys Val Ser Val Gly Leu Pro Lys Thr Glu Ala
    50                  55                  60
```

```
Asn Trp Ile Asp Val Arg Tyr Asp Leu Glu Lys Ile Glu Ser Leu Ile
65                  70                  75                  80

Gln Ser Ile His Ile Asp Thr Thr Leu Tyr Thr Asp Ser Asp Phe His
                85                  90                  95

Pro Ser Cys Lys Val Thr Ala Met Asn Cys Phe Leu Leu Glu Leu Gln
            100                 105                 110

Val Ile Leu His Glu Tyr Ser Asn Met Thr Leu Asn Glu Thr Val Arg
        115                 120                 125

Asn Val Leu Tyr Leu Ala Asn Ser Thr Leu Ser Ser Asn Lys Asn Val
    130                 135                 140

Ala Glu Ser Gly Cys Lys Glu Cys Glu Glu Leu Glu Glu Lys Thr Phe
145                 150                 155                 160

Thr Glu Phe Leu Gln Ser Phe Ile Arg Ile Val Gln Met Phe Ile Asn
                165                 170                 175

Thr Ser Ser Gly Gly Gly Ser Gly Gly Gly Gly Ser Gly Gly Gly Gly
            180                 185                 190

Ser Gly Gly Gly Gly Ser Gly Gly Gly Ser Leu Gln Gly Thr Thr Cys
        195                 200                 205

Pro Pro Pro Val Ser Ile Glu His Ala Asp Ile Arg Val Lys Asn Tyr
    210                 215                 220

Ser Val Asn Ser Arg Glu Arg Tyr Val Cys Asn Ser Gly Phe Lys Arg
225                 230                 235                 240

Lys Ala Gly Thr Ser Thr Leu Ile Glu Cys Val Ile Asn Lys Asn Thr
                245                 250                 255

Asn Val Ala His Trp Thr Thr Pro Ser Leu Lys Cys Ile Arg Asp Pro
            260                 265                 270

Ser Leu Ala His Tyr Ser Pro Val Pro Thr Val Val Thr Pro Lys Val
        275                 280                 285

Thr Ser Gln Pro Glu Ser Pro Ser Pro Ser Ala Lys Glu Pro Glu Ala
    290                 295                 300

Phe Ser Pro Lys Ser Asp Thr Ala Met Thr Thr Glu Thr Ala Ile Met
305                 310                 315                 320

Pro Gly Ser Arg Leu Thr Pro Ser Gln Thr Thr Ser Ala Gly Thr Thr
                325                 330                 335

Gly Thr Gly Ser His Lys Ser Ser Arg Ala Pro Ser Leu Ala Ala Thr
            340                 345                 350

Met Thr Leu Glu Pro Thr Ala Ser Thr Ser Leu Arg Ile Thr Glu Ile
        355                 360                 365

Ser Pro His Ser Ser Lys Met Thr Lys Val Ala Ile Ser Thr Ser Val
    370                 375                 380

Leu Leu Val Gly Ala Gly Val Val Met Ala Phe Leu Ala Trp Tyr Ile
385                 390                 395                 400

Lys Ser Arg Gln Pro Ser Gln Pro Cys Arg Val Glu Val Glu Thr Met
                405                 410                 415

Glu Thr Val Pro Met Thr Val Arg Ala Ser Ser Lys Glu Asp Glu Asp
            420                 425                 430

Thr Gly Ala Gly Ser Gly Val Lys Gln Thr Leu Asn Phe Asp Leu Leu
        435                 440                 445

Lys Leu Ala Gly Asp Val Glu Ser Asn Pro Gly Pro Cys Met Ala Pro
    450                 455                 460

Arg Val Thr Pro Leu Leu Ala Phe Ser Leu Leu Val Leu Trp Thr Phe
465                 470                 475                 480
```

```
Pro Ala Pro Thr Leu Gly Gly Ala Asn Asp Ala Glu Asp Cys Cys Leu
                485                 490                 495

Ser Val Thr Gln Arg Pro Ile Pro Gly Asn Ile Val Lys Ala Phe Arg
            500                 505                 510

Tyr Leu Leu Asn Glu Asp Gly Cys Arg Val Pro Ala Val Val Phe Thr
        515                 520                 525

Thr Leu Arg Gly Tyr Gln Leu Cys Ala Pro Pro Asp Gln Pro Trp Val
    530                 535                 540

Asp Arg Ile Ile Arg Arg Leu Lys Lys Ser Ser Ala Lys Asn Lys Gly
545                 550                 555                 560

Asn Ser Thr Arg Arg Ser Pro Val Ser
                565


<210> SEQ ID NO 10
<211> LENGTH: 1221
<212> TYPE: DNA
<213> ORGANISM: Artificial Sequence
<220> FEATURE:
<223> OTHER INFORMATION: DNA segment of sushiIL15_F2A_CCL19 (DNA segment
      #6)
<220> FEATURE:
<221> NAME/KEY: CDS
<222> LOCATION: (7)..(1179)
<223> OTHER INFORMATION: nucleic acid sequence encoding 1st F2A; a
      fusion protein "sushiIL15" comprising IL-15Ra SP, a linker and
      IL-15; 2nd F2A; and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(375)
<223> OTHER INFORMATION: mouse IL-15Ra SP and sushi domain
<220> FEATURE:
<221> NAME/KEY: misc_feature
<222> LOCATION: (376)..(435)
<223> OTHER INFORMATION: linker
<220> FEATURE:
<221> NAME/KEY: misc_feature
<222> LOCATION: (436)..(777)
<223> OTHER INFORMATION: mouse IL-15
<220> FEATURE:
<221> NAME/KEY: misc_feature
<222> LOCATION: (778)..(852)
<223> OTHER INFORMATION: F2A
<220> FEATURE:
<221> NAME/KEY: misc_feature
<222> LOCATION: (856)..(1179)
<223> OTHER INFORMATION: mouse CCL19
<220> FEATURE:
<221> NAME/KEY: misc_feature
<222> LOCATION: (1180)..(1182)
<223> OTHER INFORMATION: stop codon
<220> FEATURE:
<221> NAME/KEY: misc_feature
<222> LOCATION: (1216)..(1221)
<223> OTHER INFORMATION: restriction site (Sal I)

<400> SEQUENCE: 10

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg gcc tcc cct cag       96
Leu Ala Gly Asp Val Glu Ser Asn Pro Gly Pro Met Ala Ser Pro Gln
15                  20                  25                  30

ctg aga ggc tac ggc gtg cag gct atc ccc gtg ctg ctg ctg ctg ctg      144
Leu Arg Gly Tyr Gly Val Gln Ala Ile Pro Val Leu Leu Leu Leu Leu
                35                  40                  45
```

-continued

```
ctg ctg ctg ctg ctg cct ctg aga gtg acc cct ggc aca acc tgc cct      192
Leu Leu Leu Leu Leu Pro Leu Arg Val Thr Pro Gly Thr Thr Cys Pro
            50                  55                  60

cct ccc gtg agc atc gag cac gcc gac atc agg gtg aag aac tac tcc      240
Pro Pro Val Ser Ile Glu His Ala Asp Ile Arg Val Lys Asn Tyr Ser
        65                  70                  75

gtg aac agc agg gag agg tac gtg tgc aac agc ggc ttc aag agg aag      288
Val Asn Ser Arg Glu Arg Tyr Val Cys Asn Ser Gly Phe Lys Arg Lys
    80                  85                  90

gcc ggc acc agc acc ctg atc gag tgc gtg atc aac aag aac acc aac      336
Ala Gly Thr Ser Thr Leu Ile Glu Cys Val Ile Asn Lys Asn Thr Asn
95                  100                 105                 110

gtg gcc cac tgg acc acc ccc agc ctg aag tgc atc agg agc ggc ggc      384
Val Ala His Trp Thr Thr Pro Ser Leu Lys Cys Ile Arg Ser Gly Gly
                115                 120                 125

agc ggc ggc ggc ggc agc ggc ggc ggc agc ggc ggc ggc ggc agc ctg      432
Ser Gly Gly Gly Gly Ser Gly Gly Gly Ser Gly Gly Gly Gly Ser Leu
            130                 135                 140

cag aac tgg atc gac gtc agg tac gac ctg gag aag atc gaa agc ctg      480
Gln Asn Trp Ile Asp Val Arg Tyr Asp Leu Glu Lys Ile Glu Ser Leu
        145                 150                 155

atc cag tcc atc cac atc gat aca acc ctg tac aca gat tcc gac ttc      528
Ile Gln Ser Ile His Ile Asp Thr Thr Leu Tyr Thr Asp Ser Asp Phe
    160                 165                 170

cac ccc tcc tgt aag gtc acc gcc atg aac tgc ttc ctc ctg gaa ctc      576
His Pro Ser Cys Lys Val Thr Ala Met Asn Cys Phe Leu Leu Glu Leu
175                 180                 185                 190

cag gtc atc ctg cac gag tac tcc aac atg acc ctg aac gaa acc gtg      624
Gln Val Ile Leu His Glu Tyr Ser Asn Met Thr Leu Asn Glu Thr Val
                195                 200                 205

agg aat gtg ctg tac ctc gcc aac tcc aca ctg agc tcc aat aag aac      672
Arg Asn Val Leu Tyr Leu Ala Asn Ser Thr Leu Ser Ser Asn Lys Asn
            210                 215                 220

gtg gct gag agc ggc tgc aag gag tgt gag gag ctg gaa gag aag acc      720
Val Ala Glu Ser Gly Cys Lys Glu Cys Glu Glu Leu Glu Glu Lys Thr
        225                 230                 235

ttc acc gag ttc ctg cag agc ttc atc agg atc gtg cag atg ttc atc      768
Phe Thr Glu Phe Leu Gln Ser Phe Ile Arg Ile Val Gln Met Phe Ile
    240                 245                 250

aac aca agc ggc agc ggc gtg aag cag acc ctg aac ttc gac ctg ctg      816
Asn Thr Ser Gly Ser Gly Val Lys Gln Thr Leu Asn Phe Asp Leu Leu
255                 260                 265                 270

aag ctg gcc gga gac gtg gag agc aac cct ggc cca tgc atg gcc ccc      864
Lys Leu Ala Gly Asp Val Glu Ser Asn Pro Gly Pro Cys Met Ala Pro
                275                 280                 285

agg gtg acc cct ctg ctg gcc ttc agc ctg ctg gtg ctg tgg acc ttc      912
Arg Val Thr Pro Leu Leu Ala Phe Ser Leu Leu Val Leu Trp Thr Phe
            290                 295                 300

cct gcc cct acc ctg gga gga gcc aat gac gcc gag gac tgc tgc ctg      960
Pro Ala Pro Thr Leu Gly Gly Ala Asn Asp Ala Glu Asp Cys Cys Leu
        305                 310                 315

agc gtg acc cag aga ccc atc ccc ggc aac atc gtg aag gcc ttc agg     1008
Ser Val Thr Gln Arg Pro Ile Pro Gly Asn Ile Val Lys Ala Phe Arg
    320                 325                 330

tac ctg ctg aac gag gac ggc tgc aga gtg cct gcc gtg gtg ttc acc     1056
Tyr Leu Leu Asn Glu Asp Gly Cys Arg Val Pro Ala Val Val Phe Thr
335                 340                 345                 350

acc ctg agg ggc tac cag ctg tgt gct ccc cct gac cag cct tgg gtg     1104
Thr Leu Arg Gly Tyr Gln Leu Cys Ala Pro Pro Asp Gln Pro Trp Val
                355                 360                 365
```

```
gac agg atc atc agg agg ctg aag aag agc agc gcc aag aac aag ggc      1152
Asp Arg Ile Ile Arg Arg Leu Lys Lys Ser Ser Ala Lys Asn Lys Gly
            370                 375                 380

aac agc acc agg agg agc ccc gtg agc tgaaagctta aaccagttaa           1199
Asn Ser Thr Arg Arg Ser Pro Val Ser
        385                 390

ctggaaaacg cgtaaagtcg ac                                             1221


<210> SEQ ID NO 11
<211> LENGTH: 391
<212> TYPE: PRT
<213> ORGANISM: Artificial Sequence
<220> FEATURE:
<223> OTHER INFORMATION: Synthetic Construct

<400> SEQUENCE: 11

Gly Ser Gly Val Lys Gln Thr Leu Asn Phe Asp Leu Leu Lys Leu Ala
1               5                   10                  15

Gly Asp Val Glu Ser Asn Pro Gly Pro Met Ala Ser Pro Gln Leu Arg
            20                  25                  30

Gly Tyr Gly Val Gln Ala Ile Pro Val Leu Leu Leu Leu Leu Leu Leu
        35                  40                  45

Leu Leu Leu Pro Leu Arg Val Thr Pro Gly Thr Thr Cys Pro Pro Pro
    50                  55                  60

Val Ser Ile Glu His Ala Asp Ile Arg Val Lys Asn Tyr Ser Val Asn
65                  70                  75                  80

Ser Arg Glu Arg Tyr Val Cys Asn Ser Gly Phe Lys Arg Lys Ala Gly
                85                  90                  95

Thr Ser Thr Leu Ile Glu Cys Val Ile Asn Lys Asn Thr Asn Val Ala
            100                 105                 110

His Trp Thr Thr Pro Ser Leu Lys Cys Ile Arg Ser Gly Gly Ser Gly
        115                 120                 125

Gly Gly Gly Ser Gly Gly Gly Ser Gly Gly Gly Gly Ser Leu Gln Asn
    130                 135                 140

Trp Ile Asp Val Arg Tyr Asp Leu Glu Lys Ile Glu Ser Leu Ile Gln
145                 150                 155                 160

Ser Ile His Ile Asp Thr Thr Leu Tyr Thr Asp Ser Asp Phe His Pro
                165                 170                 175

Ser Cys Lys Val Thr Ala Met Asn Cys Phe Leu Leu Glu Leu Gln Val
            180                 185                 190

Ile Leu His Glu Tyr Ser Asn Met Thr Leu Asn Glu Thr Val Arg Asn
        195                 200                 205

Val Leu Tyr Leu Ala Asn Ser Thr Leu Ser Ser Asn Lys Asn Val Ala
    210                 215                 220

Glu Ser Gly Cys Lys Glu Cys Glu Glu Leu Glu Glu Lys Thr Phe Thr
225                 230                 235                 240

Glu Phe Leu Gln Ser Phe Ile Arg Ile Val Gln Met Phe Ile Asn Thr
                245                 250                 255

Ser Gly Ser Gly Val Lys Gln Thr Leu Asn Phe Asp Leu Leu Lys Leu
            260                 265                 270

Ala Gly Asp Val Glu Ser Asn Pro Gly Pro Cys Met Ala Pro Arg Val
        275                 280                 285

Thr Pro Leu Leu Ala Phe Ser Leu Leu Val Leu Trp Thr Phe Pro Ala
    290                 295                 300

Pro Thr Leu Gly Gly Ala Asn Asp Ala Glu Asp Cys Cys Leu Ser Val
```

```
305                 310                 315                 320

Thr Gln Arg Pro Ile Pro Gly Asn Ile Val Lys Ala Phe Arg Tyr Leu
                325                 330                 335

Leu Asn Glu Asp Gly Cys Arg Val Pro Ala Val Val Phe Thr Thr Leu
            340                 345                 350

Arg Gly Tyr Gln Leu Cys Ala Pro Pro Asp Gln Pro Trp Val Asp Arg
        355                 360                 365

Ile Ile Arg Arg Leu Lys Lys Ser Ser Ala Lys Asn Lys Gly Asn Ser
    370                 375                 380

Thr Arg Arg Ser Pro Val Ser
385                 390


<210> SEQ ID NO 12
<211> LENGTH: 1101
<212> TYPE: DNA
<213> ORGANISM: Artificial Sequence
<220> FEATURE:
<223> OTHER INFORMATION: DNA segment of IL-18_F2A_CCL19 (DNA segment #7)
<220> FEATURE:
<221> NAME/KEY: CDS
<222> LOCATION: (7)..(1059)
<223> OTHER INFORMATION: nucleic acid sequence encoding 1st F2A; IL-18;
      2nd F2A; and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(657)
<223> OTHER INFORMATION: mouse IL-18
<220> FEATURE:
<221> NAME/KEY: misc_feature
<222> LOCATION: (658)..(732)
<223> OTHER INFORMATION: F2A peptide
<220> FEATURE:
<221> NAME/KEY: misc_feature
<222> LOCATION: (736)..(1059)
<223> OTHER INFORMATION: mouse CCL19
<220> FEATURE:
<221> NAME/KEY: misc_feature
<222> LOCATION: (1060)..(1062)
<223> OTHER INFORMATION: stop codon
<220> FEATURE:
<221> NAME/KEY: misc_feature
<222> LOCATION: (1096)..(1101)
<223> OTHER INFORMATION: restriction site (Sal I)

<400> SEQUENCE: 12

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg gcc gcc atg agc       96
Leu Ala Gly Asp Val Glu Ser Asn Pro Gly Pro Met Ala Ala Met Ser
15                  20                  25                  30

gag gac tcc tgc gtg aac ttt aag gag atg atg ttc atc gac aac acc      144
Glu Asp Ser Cys Val Asn Phe Lys Glu Met Met Phe Ile Asp Asn Thr
                35                  40                  45

ctg tac ttc atc ccc gag gaa aac ggc gac ctg gag agc gac aac ttc      192
Leu Tyr Phe Ile Pro Glu Glu Asn Gly Asp Leu Glu Ser Asp Asn Phe
            50                  55                  60

ggc agg ctg cac tgc acc acc gcc gtg atc agg aac atc aac gac cag      240
Gly Arg Leu His Cys Thr Thr Ala Val Ile Arg Asn Ile Asn Asp Gln
        65                  70                  75

gtg ctg ttc gtg gac aag agg cag ccc gtg ttt gag gac atg acc gac      288
Val Leu Phe Val Asp Lys Arg Gln Pro Val Phe Glu Asp Met Thr Asp
    80                  85                  90
```

```
atc gac cag agc gcc agc gag ccc cag aca agg ctg atc atc tac atg      336
Ile Asp Gln Ser Ala Ser Glu Pro Gln Thr Arg Leu Ile Ile Tyr Met
95                  100                 105                 110

tac aag gac agc gag gtg agg ggc ctg gcc gtg aca ctg agc gtg aag      384
Tyr Lys Asp Ser Glu Val Arg Gly Leu Ala Val Thr Leu Ser Val Lys
                115                 120                 125

gac agc aag atg agc acc ctg agc tgc aaa aac aag atc atc agc ttc      432
Asp Ser Lys Met Ser Thr Leu Ser Cys Lys Asn Lys Ile Ile Ser Phe
            130                 135                 140

gag gag atg gac ccc ccc gag aac atc gac gac atc cag tcc gac ctg      480
Glu Glu Met Asp Pro Pro Glu Asn Ile Asp Asp Ile Gln Ser Asp Leu
        145                 150                 155

atc ttc ttc caa aag agg gtg ccc ggc cac aac aag atg gag ttc gag      528
Ile Phe Phe Gln Lys Arg Val Pro Gly His Asn Lys Met Glu Phe Glu
    160                 165                 170

agc agc ctg tat gag ggc cac ttc ctg gcc tgc cag aag gag gat gat      576
Ser Ser Leu Tyr Glu Gly His Phe Leu Ala Cys Gln Lys Glu Asp Asp
175                 180                 185                 190

gcc ttc aag ctg atc ctg aag aag aaa gat gag aac ggc gat aag agc      624
Ala Phe Lys Leu Ile Leu Lys Lys Lys Asp Glu Asn Gly Asp Lys Ser
                195                 200                 205

gtg atg ttc acc ctg acc aac ctg cac cag tcc ggc agc ggc gtg aag      672
Val Met Phe Thr Leu Thr Asn Leu His Gln Ser Gly Ser Gly Val Lys
            210                 215                 220

cag acc ctg aac ttc gac ctg ctg aag ctg gcc gga gac gtg gag agc      720
Gln Thr Leu Asn Phe Asp Leu Leu Lys Leu Ala Gly Asp Val Glu Ser
        225                 230                 235

aac cct ggc cca tgc atg gcc ccc agg gtg acc cct ctg ctg gcc ttc      768
Asn Pro Gly Pro Cys Met Ala Pro Arg Val Thr Pro Leu Leu Ala Phe
    240                 245                 250

agc ctg ctg gtg ctg tgg acc ttc cct gcc cct acc ctg gga gga gcc      816
Ser Leu Leu Val Leu Trp Thr Phe Pro Ala Pro Thr Leu Gly Gly Ala
255                 260                 265                 270

aat gac gcc gag gac tgc tgc ctg agc gtg acc cag aga ccc atc ccc      864
Asn Asp Ala Glu Asp Cys Cys Leu Ser Val Thr Gln Arg Pro Ile Pro
                275                 280                 285

ggc aac atc gtg aag gcc ttc agg tac ctg ctg aac gag gac ggc tgc      912
Gly Asn Ile Val Lys Ala Phe Arg Tyr Leu Leu Asn Glu Asp Gly Cys
            290                 295                 300

aga gtg cct gcc gtg gtg ttc acc acc ctg agg ggc tac cag ctg tgt      960
Arg Val Pro Ala Val Val Phe Thr Thr Leu Arg Gly Tyr Gln Leu Cys
        305                 310                 315

gct ccc cct gac cag cct tgg gtg gac agg atc atc agg agg ctg aag     1008
Ala Pro Pro Asp Gln Pro Trp Val Asp Arg Ile Ile Arg Arg Leu Lys
    320                 325                 330

aag agc agc gcc aag aac aag ggc aac agc acc agg agg agc ccc gtg     1056
Lys Ser Ser Ala Lys Asn Lys Gly Asn Ser Thr Arg Arg Ser Pro Val
335                 340                 345                 350

agc tgaaagctta aaccagttaa ctggaaaacg cgtaaagtcg ac                 1101
Ser


<210> SEQ ID NO 13
<211> LENGTH: 351
<212> TYPE: PRT
<213> ORGANISM: Artificial Sequence
<220> FEATURE:
<223> OTHER INFORMATION: Synthetic Construct

<400> SEQUENCE: 13

Gly Ser Gly Val Lys Gln Thr Leu Asn Phe Asp Leu Leu Lys Leu Ala
```

```
1               5                   10                  15

Gly Asp Val Glu Ser Asn Pro Gly Pro Met Ala Ala Met Ser Glu Asp
            20                  25                  30

Ser Cys Val Asn Phe Lys Glu Met Met Phe Ile Asp Asn Thr Leu Tyr
        35                  40                  45

Phe Ile Pro Glu Glu Asn Gly Asp Leu Glu Ser Asp Asn Phe Gly Arg
    50                  55                  60

Leu His Cys Thr Thr Ala Val Ile Arg Asn Ile Asn Asp Gln Val Leu
65                  70                  75                  80

Phe Val Asp Lys Arg Gln Pro Val Phe Glu Asp Met Thr Asp Ile Asp
                85                  90                  95

Gln Ser Ala Ser Glu Pro Gln Thr Arg Leu Ile Ile Tyr Met Tyr Lys
            100                 105                 110

Asp Ser Glu Val Arg Gly Leu Ala Val Thr Leu Ser Val Lys Asp Ser
        115                 120                 125

Lys Met Ser Thr Leu Ser Cys Lys Asn Lys Ile Ile Ser Phe Glu Glu
    130                 135                 140

Met Asp Pro Pro Glu Asn Ile Asp Asp Ile Gln Ser Asp Leu Ile Phe
145                 150                 155                 160

Phe Gln Lys Arg Val Pro Gly His Asn Lys Met Glu Phe Glu Ser Ser
                165                 170                 175

Leu Tyr Glu Gly His Phe Leu Ala Cys Gln Lys Glu Asp Asp Ala Phe
            180                 185                 190

Lys Leu Ile Leu Lys Lys Lys Asp Glu Asn Gly Asp Lys Ser Val Met
        195                 200                 205

Phe Thr Leu Thr Asn Leu His Gln Ser Gly Ser Gly Val Lys Gln Thr
    210                 215                 220

Leu Asn Phe Asp Leu Leu Lys Leu Ala Gly Asp Val Glu Ser Asn Pro
225                 230                 235                 240

Gly Pro Cys Met Ala Pro Arg Val Thr Pro Leu Leu Ala Phe Ser Leu
                245                 250                 255

Leu Val Leu Trp Thr Phe Pro Ala Pro Thr Leu Gly Gly Ala Asn Asp
            260                 265                 270

Ala Glu Asp Cys Cys Leu Ser Val Thr Gln Arg Pro Ile Pro Gly Asn
        275                 280                 285

Ile Val Lys Ala Phe Arg Tyr Leu Leu Asn Glu Asp Gly Cys Arg Val
    290                 295                 300

Pro Ala Val Val Phe Thr Thr Leu Arg Gly Tyr Gln Leu Cys Ala Pro
305                 310                 315                 320

Pro Asp Gln Pro Trp Val Asp Arg Ile Ile Arg Arg Leu Lys Lys Ser
                325                 330                 335

Ser Ala Lys Asn Lys Gly Asn Ser Thr Arg Arg Ser Pro Val Ser
            340                 345                 350
```

<210> SEQ ID NO 14
<211> LENGTH: 1011
<212> TYPE: DNA
<213> ORGANISM: Artificial Sequence
<220> FEATURE:
<223> OTHER INFORMATION: DNA segment of IL-21_F2A_CCL19 (DNA segment #8)
<220> FEATURE:
<221> NAME/KEY: CDS
<222> LOCATION: (7)..(969)
<223> OTHER INFORMATION: nucleic acid sequence encoding 1st F2A; IL-21; 2nd F2A; and CCL19
<220> FEATURE:
<221> NAME/KEY: misc_feature

```
<222> LOCATION: (7)..(81)
<223> OTHER INFORMATION: F2A peptide
<220> FEATURE:
<221> NAME/KEY: misc_feature
<222> LOCATION: (82)..(567)
<223> OTHER INFORMATION: mouse IL-21
<220> FEATURE:
<221> NAME/KEY: misc_feature
<222> LOCATION: (568)..(642)
<223> OTHER INFORMATION: F2A peptide
<220> FEATURE:
<221> NAME/KEY: misc_feature
<222> LOCATION: (646)..(969)
<223> OTHER INFORMATION: mouse CCL19
<220> FEATURE:
<221> NAME/KEY: misc_feature
<222> LOCATION: (970)..(972)
<223> OTHER INFORMATION: stop codon
<220> FEATURE:
<221> NAME/KEY: misc_feature
<222> LOCATION: (1006)..(1011)
<223> OTHER INFORMATION: restriction site (Sal I)

<400> SEQUENCE: 14

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg gag agg acc ctg       96
Leu Ala Gly Asp Val Glu Ser Asn Pro Gly Pro Met Glu Arg Thr Leu
15                  20                  25                  30

gtg tgc ctg gtg gtg att ttc ctg ggc acc gtc gcc cat aag agc agc      144
Val Cys Leu Val Val Ile Phe Leu Gly Thr Val Ala His Lys Ser Ser
                35                  40                  45

ccc cag gga ccc gac aga ctg ctg atc agg ctg agg cac ctg atc gac      192
Pro Gln Gly Pro Asp Arg Leu Leu Ile Arg Leu Arg His Leu Ile Asp
            50                  55                  60

atc gtg gag cag ctg aag atc tac gag aac gac ctg gac ccc gag ctg      240
Ile Val Glu Gln Leu Lys Ile Tyr Glu Asn Asp Leu Asp Pro Glu Leu
        65                  70                  75

ctg agc gct cct cag gac gtg aag gga cac tgc gag cac gcc gcc ttc      288
Leu Ser Ala Pro Gln Asp Val Lys Gly His Cys Glu His Ala Ala Phe
    80                  85                  90

gcc tgt ttc cag aag gcc aag ctg aag cct tcc aac ccc ggc aac aac      336
Ala Cys Phe Gln Lys Ala Lys Leu Lys Pro Ser Asn Pro Gly Asn Asn
95                  100                 105                 110

aag acc ttc atc atc gac ctg gtg gcc cag ctg agg aga agg ctg cct      384
Lys Thr Phe Ile Ile Asp Leu Val Ala Gln Leu Arg Arg Arg Leu Pro
                115                 120                 125

gcc agg agg ggc gga aag aag cag aag cac atc gcc aag tgc ccc agc      432
Ala Arg Arg Gly Gly Lys Lys Gln Lys His Ile Ala Lys Cys Pro Ser
            130                 135                 140

tgc gac tcc tac gag aag agg acc ccc aag gag ttc ctg gag agg ctg      480
Cys Asp Ser Tyr Glu Lys Arg Thr Pro Lys Glu Phe Leu Glu Arg Leu
        145                 150                 155

aag tgg ctg ctg cag aag gtg tgc aca ctg aac gcc ttc ctg agc ctg      528
Lys Trp Leu Leu Gln Lys Val Cys Thr Leu Asn Ala Phe Leu Ser Leu
    160                 165                 170

cct tgt tgc gtg agg gtg cct ccc gtg cct tcc gac agc ggc agc ggc      576
Pro Cys Cys Val Arg Val Pro Pro Val Pro Ser Asp Ser Gly Ser Gly
175                 180                 185                 190

gtg aag cag acc ctg aac ttc gac ctg ctg aag ctg gcc gga gac gtg      624
Val Lys Gln Thr Leu Asn Phe Asp Leu Leu Lys Leu Ala Gly Asp Val
                195                 200                 205

gag agc aac cct ggc cca tgc atg gcc ccc agg gtg acc cct ctg ctg      672
Glu Ser Asn Pro Gly Pro Cys Met Ala Pro Arg Val Thr Pro Leu Leu
```

```
            210                 215                 220

gcc ttc agc ctg ctg gtg ctg tgg acc ttc cct gcc cct acc ctg gga      720
Ala Phe Ser Leu Leu Val Leu Trp Thr Phe Pro Ala Pro Thr Leu Gly
        225                 230                 235

gga gcc aat gac gcc gag gac tgc tgc ctg agc gtg acc cag aga ccc      768
Gly Ala Asn Asp Ala Glu Asp Cys Cys Leu Ser Val Thr Gln Arg Pro
    240                 245                 250

atc ccc ggc aac atc gtg aag gcc ttc agg tac ctg ctg aac gag gac      816
Ile Pro Gly Asn Ile Val Lys Ala Phe Arg Tyr Leu Leu Asn Glu Asp
255                 260                 265                 270

ggc tgc aga gtg cct gcc gtg gtg ttc acc acc ctg agg ggc tac cag      864
Gly Cys Arg Val Pro Ala Val Val Phe Thr Thr Leu Arg Gly Tyr Gln
                275                 280                 285

ctg tgt gct ccc cct gac cag cct tgg gtg gac agg atc atc agg agg      912
Leu Cys Ala Pro Pro Asp Gln Pro Trp Val Asp Arg Ile Ile Arg Arg
            290                 295                 300

ctg aag aag agc agc gcc aag aac aag ggc aac agc acc agg agg agc      960
Leu Lys Lys Ser Ser Ala Lys Asn Lys Gly Asn Ser Thr Arg Arg Ser
        305                 310                 315

ccc gtg agc tgaaagctta aaccagttaa ctggaaaacg cgtaaagtcg ac          1011
Pro Val Ser
    320


<210> SEQ ID NO 15
<211> LENGTH: 321
<212> TYPE: PRT
<213> ORGANISM: Artificial Sequence
<220> FEATURE:
<223> OTHER INFORMATION: Synthetic Construct

<400> SEQUENCE: 15

Gly Ser Gly Val Lys Gln Thr Leu Asn Phe Asp Leu Leu Lys Leu Ala
1               5                   10                  15

Gly Asp Val Glu Ser Asn Pro Gly Pro Met Glu Arg Thr Leu Val Cys
            20                  25                  30

Leu Val Val Ile Phe Leu Gly Thr Val Ala His Lys Ser Ser Pro Gln
        35                  40                  45

Gly Pro Asp Arg Leu Leu Ile Arg Leu Arg His Leu Ile Asp Ile Val
    50                  55                  60

Glu Gln Leu Lys Ile Tyr Glu Asn Asp Leu Asp Pro Glu Leu Leu Ser
65                  70                  75                  80

Ala Pro Gln Asp Val Lys Gly His Cys Glu His Ala Ala Phe Ala Cys
                85                  90                  95

Phe Gln Lys Ala Lys Leu Lys Pro Ser Asn Pro Gly Asn Asn Lys Thr
            100                 105                 110

Phe Ile Ile Asp Leu Val Ala Gln Leu Arg Arg Arg Leu Pro Ala Arg
        115                 120                 125

Arg Gly Gly Lys Lys Gln Lys His Ile Ala Lys Cys Pro Ser Cys Asp
    130                 135                 140

Ser Tyr Glu Lys Arg Thr Pro Lys Glu Phe Leu Glu Arg Leu Lys Trp
145                 150                 155                 160

Leu Leu Gln Lys Val Cys Thr Leu Asn Ala Phe Leu Ser Leu Pro Cys
                165                 170                 175

Cys Val Arg Val Pro Pro Val Pro Ser Asp Ser Gly Ser Gly Val Lys
            180                 185                 190

Gln Thr Leu Asn Phe Asp Leu Leu Lys Leu Ala Gly Asp Val Glu Ser
        195                 200                 205
```

```
Asn Pro Gly Pro Cys Met Ala Pro Arg Val Thr Pro Leu Leu Ala Phe
    210                 215                 220

Ser Leu Leu Val Leu Trp Thr Phe Pro Ala Pro Thr Leu Gly Gly Ala
225                 230                 235                 240

Asn Asp Ala Glu Asp Cys Cys Leu Ser Val Thr Gln Arg Pro Ile Pro
                245                 250                 255

Gly Asn Ile Val Lys Ala Phe Arg Tyr Leu Leu Asn Glu Asp Gly Cys
            260                 265                 270

Arg Val Pro Ala Val Val Phe Thr Thr Leu Arg Gly Tyr Gln Leu Cys
        275                 280                 285

Ala Pro Pro Asp Gln Pro Trp Val Asp Arg Ile Ile Arg Arg Leu Lys
    290                 295                 300

Lys Ser Ser Ala Lys Asn Lys Gly Asn Ser Thr Arg Arg Ser Pro Val
305                 310                 315                 320

Ser


<210> SEQ ID NO 16
<211> LENGTH: 1881
<212> TYPE: DNA
<213> ORGANISM: Artificial Sequence
<220> FEATURE:
<223> OTHER INFORMATION: DNA segment of scIL27_F2A_CCL19 (DNA segment
      #9)
<220> FEATURE:
<221> NAME/KEY: CDS
<222> LOCATION: (7)..(1839)
<223> OTHER INFORMATION: nucleic acid sequence encoding 1st F2A; a
      fusion protein “scIL27” comprising EBI3, a linker and p28; 2nd F2A
      and CCL19
<220> FEATURE:
<221> NAME/KEY: misc_feature
<222> LOCATION: (7)..(81)
<223> OTHER INFORMATION: F2A peptide
<220> FEATURE:
<221> NAME/KEY: misc_feature
<222> LOCATION: (82)..(765)
<223> OTHER INFORMATION: mouse EBI3
<220> FEATURE:
<221> NAME/KEY: misc_feature
<222> LOCATION: (766)..(819)
<223> OTHER INFORMATION: linker
<220> FEATURE:
<221> NAME/KEY: misc_feature
<222> LOCATION: (820)..(1437)
<223> OTHER INFORMATION: mouse p28
<220> FEATURE:
<221> NAME/KEY: misc_feature
<222> LOCATION: (1438)..(1512)
<223> OTHER INFORMATION: F2A peptide
<220> FEATURE:
<221> NAME/KEY: misc_feature
<222> LOCATION: (1516)..(1839)
<223> OTHER INFORMATION: mouse CCL19
<220> FEATURE:
<221> NAME/KEY: misc_feature
<222> LOCATION: (1840)..(1842)
<223> OTHER INFORMATION: stop codon
<220> FEATURE:
<221> NAME/KEY: misc_feature
<222> LOCATION: (1879)..(1881)
<223> OTHER INFORMATION: restriction site (Sal I)

<400> SEQUENCE: 16

gaattc ggc agc ggc gtg aag cag acc ctg aac ttc gac ctg ctg aag        48
       Gly Ser Gly Val Lys Gln Thr Leu Asn Phe Asp Leu Leu Lys
       1               5                   10

ctg gcc gga gac gtg gag agc aac cct ggc cct atg agc aag ctc ctc        96
Leu Ala Gly Asp Val Glu Ser Asn Pro Gly Pro Met Ser Lys Leu Leu
15                  20                  25                  30
```

-continued

```
ttt ctg tcc ctg gcc ctg tgg gcc agc aga tcc cct ggc tac aca gaa      144
Phe Leu Ser Leu Ala Leu Trp Ala Ser Arg Ser Pro Gly Tyr Thr Glu
                35                  40                  45

aca gcc ctg gtg gcc ctg tcc caa ccc aga gtg cag tgt cac gct tcc      192
Thr Ala Leu Val Ala Leu Ser Gln Pro Arg Val Gln Cys His Ala Ser
            50                  55                  60

agg tac ccc gtg gct gtg gac tgc agc tgg acc cct ctg caa gcc cct      240
Arg Tyr Pro Val Ala Val Asp Cys Ser Trp Thr Pro Leu Gln Ala Pro
        65                  70                  75

aat agc acc agg agc acc tcc ttc atc gcc acc tac aga ctg gga gtg      288
Asn Ser Thr Arg Ser Thr Ser Phe Ile Ala Thr Tyr Arg Leu Gly Val
    80                  85                  90

gcc acc cag cag cag agc cag cct tgc ctg cag agg tcc cct cag gcc      336
Ala Thr Gln Gln Gln Ser Gln Pro Cys Leu Gln Arg Ser Pro Gln Ala
95                  100                 105                 110

tcc aga tgc aca atc cct gat gtg cac ctg ttt agc acc gtg ccc tac      384
Ser Arg Cys Thr Ile Pro Asp Val His Leu Phe Ser Thr Val Pro Tyr
                115                 120                 125

atg ctg aac gtg aca gcc gtg cac cct gga gga gcc agc agc tcc ctc      432
Met Leu Asn Val Thr Ala Val His Pro Gly Gly Ala Ser Ser Ser Leu
            130                 135                 140

ctg gcc ttc gtc gcc gag aga atc atc aag cct gac ccc cct gag ggc      480
Leu Ala Phe Val Ala Glu Arg Ile Ile Lys Pro Asp Pro Pro Glu Gly
        145                 150                 155

gtg aga ctg aga aca gct ggc cag aga ctg cag gtg ctg tgg cac cct      528
Val Arg Leu Arg Thr Ala Gly Gln Arg Leu Gln Val Leu Trp His Pro
    160                 165                 170

ccc gcc tcc tgg cct ttc ccc gat atc ttc tcc ctg aag tac aga ctg      576
Pro Ala Ser Trp Pro Phe Pro Asp Ile Phe Ser Leu Lys Tyr Arg Leu
175                 180                 185                 190

agg tac agg aga aga ggc gct agc cac ttc aga cag gtg ggc ccc att      624
Arg Tyr Arg Arg Arg Gly Ala Ser His Phe Arg Gln Val Gly Pro Ile
                195                 200                 205

gag gct acc acc ttt acc ctc agg aat agc aag ccc cat gct aag tac      672
Glu Ala Thr Thr Phe Thr Leu Arg Asn Ser Lys Pro His Ala Lys Tyr
            210                 215                 220

tgt atc cag gtg tcc gcc cag gat ctg aca gac tac ggc aag ccc tcc      720
Cys Ile Gln Val Ser Ala Gln Asp Leu Thr Asp Tyr Gly Lys Pro Ser
        225                 230                 235

gac tgg agc ctg cct gga caa gtg gaa agc gct ccc cac aag cct gga      768
Asp Trp Ser Leu Pro Gly Gln Val Glu Ser Ala Pro His Lys Pro Gly
    240                 245                 250

agc aca tcc gga agc ggc aaa ccc ggc agc gga gag gga tcc acc aaa      816
Ser Thr Ser Gly Ser Gly Lys Pro Gly Ser Gly Glu Gly Ser Thr Lys
255                 260                 265                 270

ggc ttc cct acc gac ccc ctg tct tta caa gaa ctg aga agg gag ttc      864
Gly Phe Pro Thr Asp Pro Leu Ser Leu Gln Glu Leu Arg Arg Glu Phe
                275                 280                 285

acc gtg agc ctg tat ctg gcc agg aag ctc ctc agc gag gtg cag ggc      912
Thr Val Ser Leu Tyr Leu Ala Arg Lys Leu Leu Ser Glu Val Gln Gly
            290                 295                 300

tat gtg cac agc ttc gcc gaa agc agg ctg ccc ggc gtg aac ctg gat      960
Tyr Val His Ser Phe Ala Glu Ser Arg Leu Pro Gly Val Asn Leu Asp
        305                 310                 315

ctg ctg ccc ctg ggc tac cac ctg cct aac gtg tcc ctg acc ttc cag     1008
Leu Leu Pro Leu Gly Tyr His Leu Pro Asn Val Ser Leu Thr Phe Gln
    320                 325                 330

gct tgg cat cac ctg tcc gac tcc gag agg ctc tgc ttt ctg gcc acc     1056
Ala Trp His His Leu Ser Asp Ser Glu Arg Leu Cys Phe Leu Ala Thr
```

```
335                 340                 345                 350

acc ctg agg ccc ttc cct gcc atg ctg gga gga ctg ggc acc cag gga     1104
Thr Leu Arg Pro Phe Pro Ala Met Leu Gly Gly Leu Gly Thr Gln Gly
                355                 360                 365

acc tgg acc agc agc gag agg gaa cag ctg tgg gcc atg aga ctg gac     1152
Thr Trp Thr Ser Ser Glu Arg Glu Gln Leu Trp Ala Met Arg Leu Asp
            370                 375                 380

ctg agg gat ctg cac aga cac ctg agg ttc cag gtg ctg gcc gcc ggc     1200
Leu Arg Asp Leu His Arg His Leu Arg Phe Gln Val Leu Ala Ala Gly
        385                 390                 395

ttc aag tgt agc aaa gag gag gag gac aaa gaa gaa gaa gaa gag gaa     1248
Phe Lys Cys Ser Lys Glu Glu Glu Asp Lys Glu Glu Glu Glu Glu Glu
    400                 405                 410

gaa gag gaa gag aag aaa ctc ccc ctg gga gcc ctg gga ggc cct aat     1296
Glu Glu Glu Glu Lys Lys Leu Pro Leu Gly Ala Leu Gly Gly Pro Asn
415                 420                 425                 430

cag gtg tcc tcc cag gtg tcc tgg cct cag ctg ctg tat acc tac cag     1344
Gln Val Ser Ser Gln Val Ser Trp Pro Gln Leu Leu Tyr Thr Tyr Gln
                435                 440                 445

ctg ctg cac agc ctg gag ctg gtg ctg tcc agg gct gtg agg gac ctg     1392
Leu Leu His Ser Leu Glu Leu Val Leu Ser Arg Ala Val Arg Asp Leu
            450                 455                 460

ctc ctg ctg agc ctg cct aga agg cct ggc agc gct tgg gac tcc ggc     1440
Leu Leu Leu Ser Leu Pro Arg Arg Pro Gly Ser Ala Trp Asp Ser Gly
        465                 470                 475

agc ggc gtg aag cag acc ctg aac ttc gac ctg ctg aag ctg gcc gga     1488
Ser Gly Val Lys Gln Thr Leu Asn Phe Asp Leu Leu Lys Leu Ala Gly
    480                 485                 490

gac gtg gag agc aac cct ggc cca tgc atg gcc ccc agg gtg acc cct     1536
Asp Val Glu Ser Asn Pro Gly Pro Cys Met Ala Pro Arg Val Thr Pro
495                 500                 505                 510

ctg ctg gcc ttc agc ctg ctg gtg ctg tgg acc ttc cct gcc cct acc     1584
Leu Leu Ala Phe Ser Leu Leu Val Leu Trp Thr Phe Pro Ala Pro Thr
                515                 520                 525

ctg gga gga gcc aat gac gcc gag gac tgc tgc ctg agc gtg acc cag     1632
Leu Gly Gly Ala Asn Asp Ala Glu Asp Cys Cys Leu Ser Val Thr Gln
            530                 535                 540

aga ccc atc ccc ggc aac atc gtg aag gcc ttc agg tac ctg ctg aac     1680
Arg Pro Ile Pro Gly Asn Ile Val Lys Ala Phe Arg Tyr Leu Leu Asn
        545                 550                 555

gag gac ggc tgc aga gtg cct gcc gtg gtg ttc acc acc ctg agg ggc     1728
Glu Asp Gly Cys Arg Val Pro Ala Val Val Phe Thr Thr Leu Arg Gly
    560                 565                 570

tac cag ctg tgt gct ccc cct gac cag cct tgg gtg gac agg atc atc     1776
Tyr Gln Leu Cys Ala Pro Pro Asp Gln Pro Trp Val Asp Arg Ile Ile
575                 580                 585                 590

agg agg ctg aag aag agc agc gcc aag aac aag ggc aac agc acc agg     1824
Arg Arg Leu Lys Lys Ser Ser Ala Lys Asn Lys Gly Asn Ser Thr Arg
                595                 600                 605

agg agc ccc gtg agc tgaaagctta aaccagttaa ctggaaaacg cgtaaagtcg     1879
Arg Ser Pro Val Ser
            610

ac                                                                  1881
```

<210> SEQ ID NO 17
<211> LENGTH: 611
<212> TYPE: PRT
<213> ORGANISM: Artificial Sequence
<220> FEATURE:
<223> OTHER INFORMATION: Synthetic Construct

<400> SEQUENCE: 17

Gly Ser Gly Val Lys Gln Thr Leu Asn Phe Asp Leu Leu Lys Leu Ala
1               5                   10                  15

Gly Asp Val Glu Ser Asn Pro Gly Pro Met Ser Lys Leu Leu Phe Leu
            20                  25                  30

Ser Leu Ala Leu Trp Ala Ser Arg Ser Pro Gly Tyr Thr Glu Thr Ala
        35                  40                  45

Leu Val Ala Leu Ser Gln Pro Arg Val Gln Cys His Ala Ser Arg Tyr
    50                  55                  60

Pro Val Ala Val Asp Cys Ser Trp Thr Pro Leu Gln Ala Pro Asn Ser
65                  70                  75                  80

Thr Arg Ser Thr Ser Phe Ile Ala Thr Tyr Arg Leu Gly Val Ala Thr
                85                  90                  95

Gln Gln Gln Ser Gln Pro Cys Leu Gln Arg Ser Pro Gln Ala Ser Arg
            100                 105                 110

Cys Thr Ile Pro Asp Val His Leu Phe Ser Thr Val Pro Tyr Met Leu
        115                 120                 125

Asn Val Thr Ala Val His Pro Gly Gly Ala Ser Ser Ser Leu Leu Ala
    130                 135                 140

Phe Val Ala Glu Arg Ile Ile Lys Pro Asp Pro Pro Glu Gly Val Arg
145                 150                 155                 160

Leu Arg Thr Ala Gly Gln Arg Leu Gln Val Leu Trp His Pro Pro Ala
                165                 170                 175

Ser Trp Pro Phe Pro Asp Ile Phe Ser Leu Lys Tyr Arg Leu Arg Tyr
            180                 185                 190

Arg Arg Arg Gly Ala Ser His Phe Arg Gln Val Gly Pro Ile Glu Ala
        195                 200                 205

Thr Thr Phe Thr Leu Arg Asn Ser Lys Pro His Ala Lys Tyr Cys Ile
    210                 215                 220

Gln Val Ser Ala Gln Asp Leu Thr Asp Tyr Gly Lys Pro Ser Asp Trp
225                 230                 235                 240

Ser Leu Pro Gly Gln Val Glu Ser Ala Pro His Lys Pro Gly Ser Thr
                245                 250                 255

Ser Gly Ser Gly Lys Pro Gly Ser Gly Glu Gly Ser Thr Lys Gly Phe
            260                 265                 270

Pro Thr Asp Pro Leu Ser Leu Gln Glu Leu Arg Arg Glu Phe Thr Val
        275                 280                 285

Ser Leu Tyr Leu Ala Arg Lys Leu Leu Ser Glu Val Gln Gly Tyr Val
    290                 295                 300

His Ser Phe Ala Glu Ser Arg Leu Pro Gly Val Asn Leu Asp Leu Leu
305                 310                 315                 320

Pro Leu Gly Tyr His Leu Pro Asn Val Ser Leu Thr Phe Gln Ala Trp
                325                 330                 335

His His Leu Ser Asp Ser Glu Arg Leu Cys Phe Leu Ala Thr Thr Leu
            340                 345                 350

Arg Pro Phe Pro Ala Met Leu Gly Gly Leu Gly Thr Gln Gly Thr Trp
        355                 360                 365

Thr Ser Ser Glu Arg Glu Gln Leu Trp Ala Met Arg Leu Asp Leu Arg
    370                 375                 380

Asp Leu His Arg His Leu Arg Phe Gln Val Leu Ala Ala Gly Phe Lys
385                 390                 395                 400

Cys Ser Lys Glu Glu Glu Asp Lys Glu Glu Glu Glu Glu Glu Glu Glu

```
                405                 410                 415

Glu Glu Lys Lys Leu Pro Leu Gly Ala Leu Gly Gly Pro Asn Gln Val
            420                 425                 430

Ser Ser Gln Val Ser Trp Pro Gln Leu Leu Tyr Thr Tyr Gln Leu Leu
        435                 440                 445

His Ser Leu Glu Leu Val Leu Ser Arg Ala Val Arg Asp Leu Leu Leu
    450                 455                 460

Leu Ser Leu Pro Arg Arg Pro Gly Ser Ala Trp Asp Ser Gly Ser Gly
465                 470                 475                 480

Val Lys Gln Thr Leu Asn Phe Asp Leu Leu Lys Leu Ala Gly Asp Val
                485                 490                 495

Glu Ser Asn Pro Gly Pro Cys Met Ala Pro Arg Val Thr Pro Leu Leu
            500                 505                 510

Ala Phe Ser Leu Leu Val Leu Trp Thr Phe Pro Ala Pro Thr Leu Gly
        515                 520                 525

Gly Ala Asn Asp Ala Glu Asp Cys Cys Leu Ser Val Thr Gln Arg Pro
    530                 535                 540

Ile Pro Gly Asn Ile Val Lys Ala Phe Arg Tyr Leu Leu Asn Glu Asp
545                 550                 555                 560

Gly Cys Arg Val Pro Ala Val Val Phe Thr Thr Leu Arg Gly Tyr Gln
                565                 570                 575

Leu Cys Ala Pro Pro Asp Gln Pro Trp Val Asp Arg Ile Ile Arg Arg
            580                 585                 590

Leu Lys Lys Ser Ser Ala Lys Asn Lys Gly Asn Ser Thr Arg Arg Ser
        595                 600                 605

Pro Val Ser
    610


<210> SEQ ID NO 18
<211> LENGTH: 162
<212> TYPE: PRT
<213> ORGANISM: Homo sapiens
<220> FEATURE:
<221> NAME/KEY: MISC_FEATURE
<222> LOCATION: (1)..(29)
<223> OTHER INFORMATION: Signal peptide
<220> FEATURE:
<221> NAME/KEY: MISC_FEATURE
<222> LOCATION: (30)..(48)
<223> OTHER INFORMATION: Propeptide
<220> FEATURE:
<221> NAME/KEY: MISC_FEATURE
<222> LOCATION: (49)..(162)
<223> OTHER INFORMATION: Interleukin-15

<400> SEQUENCE: 18

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95
```

```
Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser


<210> SEQ ID NO 19
<211> LENGTH: 267
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Signal Peptide
<220> FEATURE:
<221> NAME/KEY: MISC_FEATURE
<222> LOCATION: (31)..(267)
<223> OTHER INFORMATION: Interleukin-15 receptor subunit alpha
<220> FEATURE:
<221> NAME/KEY: MISC_FEATURE
<222> LOCATION: (31)..(95)
<223> OTHER INFORMATION: Sushi domain
<220> FEATURE:
<221> NAME/KEY: MISC_FEATURE
<222> LOCATION: (31)..(205)
<223> OTHER INFORMATION: Extracellular domain
<220> FEATURE:
<221> NAME/KEY: MISC_FEATURE
<222> LOCATION: (206)..(228)
<223> OTHER INFORMATION: Helical domain
<220> FEATURE:
<221> NAME/KEY: MISC_FEATURE
<222> LOCATION: (229)..(267)
<223> OTHER INFORMATION: Cytoplasmic domain

<400> SEQUENCE: 19

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
    130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175
```

-continued

```
Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265
```

CAR-EXPRESSING T CELLS AND CAR EXPRESSION VECTOR

TECHNICAL FIELD

The present invention relates to immune cells expressing a chimeric antigen receptor (hereinafter referred to as "CAR") (hereinafter referred to as "CAR-expressing immune cells") that can be used for cancer immunotherapy, typically, T cells expressing a CAR (hereinafter referred to as "CAR-T cells"), and an expression vector for producing the CAR-expressing immune cells (such as CAR-T cells). More specifically, the present invention relates to CAR-expressing immune cells (such as CAR-T cells) expressing predetermined cytokines and chemokines, and an expression vector for producing the cells.

BACKGROUND ART

Cancer immunotherapy by administration of CAR-T cells has been shown to be effective in hematopoietic malignancies such as leukemia and lymphoma, but there are cancer types and cases for which no therapeutic effect is observed due to problems such as low survival efficiency of CAR-T cells in vivo and inhibition of the activity of CAR-T cells in the microenvironment of cancers by the tumor immuno-avoidance mechanism of cancer cells, especially, in solid cancers. Therefore, CAR-T cells exhibiting a therapeutic effect and having higher antitumor activity are required, especially, in solid cancers.

Patent Literature 1 and Non Patent Literature 1 disclose CAR-T cells that express IL-7 and CCL19 and are more excellent in antitumor activity than conventional CAR-T cells. However, Patent Literature 1 and Non Patent Literature 1 do not include specific descriptions of other combinations of cytokines and chemokines.

Non Patent Literature 2 discloses CAR-T cells that have improved persistence independent of CAR signaling and express membrane-bound chimeric IL-15 (mbIL-15). However, Non Patent Literature 2 does not include specific descriptions of combinations of mbIL-15 with chemokines such as CCL19.

Non Patent Literature 3 discloses that use of a fusion protein comprising IL-15 linked to an IL-15Rαsushi domain via a flexible linker can provide more potent activity in proliferation of lymphocytes (such as NK cells, NK-T cells, and memory CD8-positive cells), activation of dendritic cells, and the like than that caused by conventional combined use of IL-15 and IL-15Rαsushi domain. However, Non Patent Literature 3 does not include specific descriptions of combinations of IL-15 and IL-15Rαsushi domain with chemokines such as CCL19.

Non Patent Literature 4 discloses that transfection of a secretory fusion protein of mouse IL-15 and IL-15Rα improves the viability and proliferative capacity of CD8-positive T cells. However, Non Patent Literature 4 does not include specific descriptions of combinations of IL-15 with chemokines such as CCL19.

Non Patent Literature 5 discloses single-chain IL-27 (p28 and EBI3 linked by a flexible linker) and an effect thereof on treatment of inflammatory bowel disease (IBD). However, Non Patent Literature 5 does not include specific descriptions of CAR-T cells and combinations of single-chain IL-27 with chemokines such as CCL19.

Patent Literature 2 discloses T cells expressing recombinant IL-7, recombinant IL-15, or combinations of these and discloses that expression of such cytokines improves T cell survival. However, Patent Literature 2 does not include specific descriptions of CAR-T cells and combinations of the specific cytokines with chemokines such as CCL19.

Patent Literature 3 discloses a modified natural killer T cell containing an expression construct encoding IL-2, IL-4, IL-7, IL-15 or combinations of these, and a CAR construct. However, Patent Literature 3 does not include specific descriptions of combinations of the specific cytokines with chemokines such as CCL19.

Patent Literature 4 discloses CAR-T cells expressing membrane-bound cytokines such as IL-7, IL-15 (IL-15/IL-15Rα fusion protein), and IL-21. However, Patent Literature 4 does not include specific descriptions of combinations of the specific cytokines with chemokines such as CCL19.

Patent Literature 5 discloses a CAR-T cell expressing IL-15 and targeting CD19. However, Patent Literature 5 does not include specific descriptions of combinations of IL-15 with chemokines such as CCL19.

Non Patent Literature 6 discloses a CAR-T cell expressing IL-15 and/or IL-21 and targeting GPC3. However, Non Patent Literature 6 does not include specific descriptions of combinations of the specific cytokines with chemokines such as CCL19.

CITATION LIST

Patent Literature

Patent Literature 1: WO 2016/056228
Patent Literature 2: WO 2007/037780
Patent Literature 3: WO 2013/040371
Patent Literature 4: WO 2014/186469
Patent Literature 5: US 2013/0071414

Non Patent Literature

Non Patent Literature 1: Adachi et al., Nature Biotechnology, VOL 36, No 4, 346-353
Non Patent Literature 2: Hurton et al., Proc Natl Acad Sci., 113 (48), E7788-97, 2016
Non Patent Literature 3: Mortier et al., J Biol Chem. 281 (3), 1612-9, 2006
Non Patent Literature 4: Rowley et al., Eur J Immunol. 39 (2), 491-506, 2009
Non Patent Literature 5: Sasaoka et al., Am J Physiol Gastrointest Liver Physiol 300: G568-576
Non Patent Literature 6: Barta et al., Armored Glypican-3-Specific CAR T cells for the Immunotherapy of Hepatocellular Carcinoma, ASGCT 2018 May 2018, abstract

SUMMARY OF INVENTION

Technical Problem

It is an object of the present invention to provide immune cells (such as CAR-T cells) having higher antitumor activity than immune cells (such as CAR-T cells) expressing CAR alone (not expressing cytokines and/or chemokines).

Solution to Problem

There are at least several hundreds of molecules in vivo that can control the functions of immune cells such as T cells. The inventors have found that the antitumor activity is enhanced by CAR-T cells expressing at least one selected from the group consisting of interleukin-15 (IL-15), interleukin-18 (IL-18), interleukin-21 (IL-21), and interleukin-27

(IL-27), which are cytokines, in combination with CC chemokine ligand 19 (CCL19), which is a chemokine, together with CAR, as compared with cells expressing CAR alone, and the persistence and proliferation of CAR-T cells are especially improved, thereby accomplishing the present invention.

IL-15, IL-18, IL-27, and CCL19 are cytokines and a chemokine that are not expressed by natural T cells (in which no exogenous genes are introduced) in vivo. IL-21 is a cytokine expressed by natural T cells in vivo (such as NK T cells and CD4-positive T cells). In the present invention, expression of the predetermined cytokine and chemokine means expression of the predetermined cytokine and chemokine at higher levels than in natural T cells in vivo by introducing genes for expressing the predetermined exogenous cytokine and chemokine into T cells.

Further, the embodiment of gene transfer and expression of the aforementioned predetermined interleukins and chemokine together with CAR in T cells can be extended to an embodiment of gene transfer and expression thereof in immune cells other than T cells, such as NK cells, monocytes, macrophages, and dendritic cells.

The present invention includes at least the following aspects.

[1] A T cell expressing:

(1) a chimeric antigen receptor (CAR);

(2) at least one selected from the group consisting of interleukin-15 (IL-15), interleukin-18 (IL-18), interleukin-21 (IL-21), and interleukin-27 (IL-27); and (3) CC chemokine ligand 19 (CCL19). [2] The T cell according to item 1, wherein the (2) is IL-15.

[3] The T cell according to item 2, wherein the IL-15 is linked to IL-15Rα to form a fusion protein.

[4] The T cell according to item 3, wherein the fusion protein is a fusion protein comprising IL-15LSP linked to IL-15 ($IL15_{LSP}$), a fusion protein comprising IL-15Rα extracellular domain linked to IL-15 ($_{s}IL15_{RA}$), a fusion protein comprising IL-15 linked to full-length IL-15Rα ($_{mb}IL15_{RA}$), or a fusion protein comprising IL-15Rα containing a signal peptide and a sushi domain linked to IL-15 ($_{sushi}IL15$).

[5] The T cell according to item 3, wherein the fusion protein is a fusion protein comprising IL-15 linked to full-length IL-15Rα ($_{mb}IL15_{RA}$), or a fusion protein comprising IL-15Rα containing a signal peptide and a sushi domain linked to IL-15 ($_{sushi}IL15$).

[6] A medicament comprising the T cell according to item 1.

[7] The medicament according to item 6, wherein the medicament is a therapeutic agent for cancer.

[8] The medicament according to item 7, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

[9] An expression vector comprising:

(1) a nucleic acid encoding a CAR;

(2) a nucleic acid encoding at least one selected from the group consisting of IL-15, IL-18, IL-21, and IL-27; and (3) a nucleic acid encoding CCL19.

[10] The expression vector according to item 9, wherein the (2) is IL-15.

[11] The expression vector according to item 10, wherein the IL-15 is linked to IL-15Rα to form a fusion protein.

[12] The expression vector according to item 11, wherein the fusion protein is a fusion protein comprising IL-15LSP linked to IL-15 ($IL15_{LSP}$), a fusion protein comprising IL-15Rα extracellular domain linked to IL-15 ($_{s}IL15_{RA}$), a fusion protein comprising IL-15 linked to full-length IL-15Rα ($_{mb}IL15_{RA}$), or a fusion protein comprising IL-15Rα containing a signal peptide and a sushi domain linked to IL-15 ($_{sushi}IL15$).

[13] The expression vector according to item 11, wherein the fusion protein is a fusion protein comprising IL-15 linked to full-length IL-15Rα ($_{mb}IL15_{RA}$), or a fusion protein comprising IL-15Rα containing a signal peptide and a sushi domain linked to IL-15 ($_{sushi}IL15$).

[14] A method for producing a CAR-T cell, comprising a step of introducing the expression vector according to item 9 into a T cell.

[15] A method for treating cancer, comprising a step of administering the T cell according to item 1 to a subject in need of cancer treatment.

[16] The treatment method according to item 15, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

[17] The T cell according to item 1, for use as an active component for cancer treatment.

[18] The T cell according to item 17, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

Hereinafter, the T cell of [1] above is also referred to as "T cell of the present invention", the medicament of [6] above is also referred to as "medicament of the present invention", the expression vector of [9] above is also referred to as "expression vector of the present invention", and the method for producing a CAR-T cell of above is also referred to as "the production method of the present invention".

Those skilled in the art would be able to appropriately convert the embodiments (categories) of the invention in consideration of the contents disclosed herein as a whole. For example, the medicament of the present invention according to [6] above can be converted into "a method for treating cancer, comprising a step of administering a T cell expressing: (1) a CAR; (2) at least one selected from the group consisting of IL-15, IL-18, IL-21, and IL-27; and (3) CCL19 to a subject in need of cancer treatment", "a T cell expressing: (1) a CAR; (2) at least one selected from the group consisting of IL-15, IL-18, IL-21, and IL-27; and (3) CCL19 for use as an active component for cancer treatment", and "use of a T cell expressing: (1) a CAR; (2) at least one selected from the group consisting of IL-15, IL-18, IL-21, and IL-27; and (3) CCL19 for the manufacture of a medicament for treating cancer.

Those skilled in the art would be able to appropriately convert the embodiment of the T cell of the present invention to be obtained by allowing the T cell to express the predetermined cytokine and chemokine together with a CAR, and relevant embodiments thereto such as the medicament of the present invention, the expression vector of the present invention, and the production method of the present invention into an embodiment of immune cells other than T cells (such as NK cells, monocytes, macrophages, and dendritic cells) expressing the predetermined cytokine and chemokine together with a CAR and relevant embodiments thereto such as a medicament, an expression vector, and a production method, in consideration of the contents disclosed herein as a whole.

Advantageous Effects of Invention

The persistence and proliferation of the T cell of the present invention are improved by the T cell expressing the predetermined cytokine (such as IL-15) and chemokine (CCL19). Therefore, the antitumor activity by the CAR can be enhanced (e.g., reduction in the number of residual tumor cells, improvement in amount of IFNγ to be produced, and improvement in migration and accumulation of host immune cells (such as T cells, dendritic cells, NK cells) in the tumor site). Further, the therapeutic effect on cancer can be improved by a medicament containing the T cell of the present invention. In particular, the T cell of the present invention may be involved in NK cell activation and therefore may be useful for the treatment of carcinomas sensitive to NK cells (such as melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, and leukemia). Further, since the enhancement of the antitumor activity reduces the number of cells to be administered, effects such as reduction in side effects such as CRS (Cytokine Release Syndrome) and reduction in production cost are expected.

The combination of the predetermined cytokine and chemokine of the present invention exerts action and effect that various CAR-expressing immune cells with high antitumor activity can be obtained even in the case where the genes are transferred and expressed together with a CAR gene in immune cells in general, that is, not only in T cells as mentioned above but also in NK cells, monocytes, macrophages, and dendritic cells.

BRIEF DESCRIPTION OF DRAWINGS

FIG. 1 shows the results of analysis of the expression level of the CAR (the horizontal axis) and CD8 (the vertical axis) in the following T cells of Example (Experimental Example 1) by flow cytometry. The numerical value (%) in the figure represents the percentage of the cell population in each compartment with respect to the total cells. "Transduction (−)" is a result for transduction (−) T cells of Comparative Example 1 (T cells without transduction), "conv. CAR-T" is a result for conv. CAR-T cells of Comparative Example 2 (anti-human CD20 CAR-T cells), "$15_{LSP}$×19 CAR-T" is a result for IL15LSP×CCL19 CAR-T cells of Example 1-1 ($IL15_{LSP}$_CCL19_anti-human CD20 CAR-T cells), "$_{s}15_{RA}$×19 CAR-T" is a result for $_{s}IL15_{RA}$×CCL19 CAR-T cells of Example 1-2 ($_{s}IL15_{RA}$_CCL19_anti-human CD20 CAR-T cells), "$_{mb}15_{RA}$×19 CAR-T" is a result for $_{mb}IL15_{RA}$×CCL19 CAR-T cells of Example 1-3 ($_{mb}IL15_{RA}$_CCL19_anti-human CD20 CAR-T cells), "$_{sushi}15$×19 CAR-T" is a result for $_{sushi}IL15$×CCL19 CAR-T cells of Example 1-4 ($_{sushi}IL15$_CCL19_anti-human CD20 CAR-T cells), "18×19 CAR-T" is a result for IL-18×CCL19 CAR-T cells of Example 2 (IL18_CCL19_anti-human CD20 CAR-T cells), "21×19 CAR-T" is a result for IL-21×CCL19 CAR-T cells of Example 3 (IL21_CCL19_anti-human CD20 CAR-T cells), and "$_{sc}27$×19 CAR-T" is a result for $_{sc}IL27$×CCL19 CAR-T cells of Example 4 ($_{sc}IL27$_CCL19_anti-human CD20 CAR-T cells). The same applies also to FIGS. 2 to 6 below.

FIG. 2 shows the results of measurement of amounts of (A) IL-15, (B) IL-18, (C) IL-21, (D) IL-27, and (E) CCL19 secreted into the culture supernatant in the T cells in Example (Experimental Example 1) by ELISA.

FIG. 3 shows the results of measurement of the number of living cells in the T cells 3 days, 5 days, and 7 days after stimulation of activation by co-culture with human CD20 expressing P815 mastocytoma (hCD20/P815) in Example (Experimental Example 2).

FIG. 4 shows the results of histogram analysis of the staining intensity with a CytoTell reagent in the T cells in Example (Experimental Example 2). The peak of the histogram shows the number of generations due to cell division, and the numerical value (%) in the donut graph shows the percentage of gated fractions in the Thy1.2-positive T cell population (1 represents the undivided first generation, 2 represents the second generation after one division, 3 represents the third generation after two divisions, 4 represents the fourth generation after three divisions, >5 represents the fifth and subsequent generations after four or more divisions).

FIG. 5 shows the results of measurement of the tumor cytotoxic activity of the T cells in (A) target tumor cells (hCD20/P815) and (B) control tumor cells (P815) in Example (Experimental Example 3) by flow cytometry.

FIG. 6 shows the results of measurement of the concentration of IFNγ in the culture supernatant of the T cells at the time of co-culture with (A) target tumor cells (hCD20/P815), and (B) control tumor cells (P815) in Example (Experimental Example 3).

FIG. 7 shows the arrangement of genes and the like contained in the nucleotide sequence of SEQ ID NO: 1 (anti-human CD20 CAR DNA fragment).

FIG. 8 shows the arrangement of genes and the like contained in the nucleotide sequence of SEQ ID NO: 3 (MCS DNA fragment).

FIG. 9 shows the arrangement of genes and the like contained in the nucleotide sequence of SEQ ID NO: 4 ($IL15_{LSP}$_F2A_CCL19 DNA fragment).

FIG. 10 shows the arrangement of genes and the like contained in the nucleotide sequence of SEQ ID NO: 6 ($_{s}IL15_{RA}$_F2A_CCL19 DNA fragment).

FIG. 11 shows the arrangement of genes and the like contained in the nucleotide sequence of SEQ ID NO: 8 ($_{mb}IL15_{RA}$_F2A_CCL19 DNA fragment).

FIG. 12 shows the arrangement of genes and the like contained in the nucleotide sequence of SEQ ID NO: 10 ($_{sushi}IL15$_F2A_CCL19 DNA fragment).

FIG. 13 shows the arrangement of genes and the like contained in the nucleotide sequence of SEQ ID NO: 12 (IL-18_F2A_CCL19 DNA fragment).

FIG. 14 shows the arrangement of genes and the like contained in the nucleotide sequence of SEQ ID NO: 14 (IL-21_F2A_CCL19 DNA fragment).

FIG. 15 shows the arrangement of genes and the like contained in the nucleotide sequence of SEQ ID NO: 16 ($_{sc}$IL27_F2A_CCL19 DNA fragment).

FIG. 16 shows the results of measurement of the antitumor activity (change in tumor volume) for a mouse melanoma tumor transplant model in Example (Experimental Example 4).

FIG. 17 shows the results of measurement of the antitumor activity (change in tumor volume) for a mouse colorectal cancer tumor model in Example (Experimental Example 4).

DESCRIPTION OF EMBODIMENTS

As used herein, "transfection" means introduction of any substance into a cell. A cell includes at least a cytoplasm and a nucleus thereinside.

"Culture" or "culturing" means maintaining, proliferating, and/or differentiating cells outside tissues or outside the body, e.g., in a dish, a Petri dish, a flask, or a culture tank.

"Pluripotency" means the ability to differentiate into tissues and cells having various different morphologies and functions, and the ability to differentiate into cells of any lineage of the three germ layers. "Pluripotency" is distinguished from "totipotency" which means the ability to differentiate into any tissue in the body including blastocysts, in that the pluripotency does not mean the ability to differentiate into blastocysts and therefore lacks the ability to form individuals.

"Multipotency" means the ability to differentiate into cells of a limited number of lineages. For example, mesenchymal stem cells, hematopoietic stem cells, and neural stem cells are multipotent but not pluripotent.

Examples of "stem cells" include pluripotent stem cells.

The "pluripotent stem cells" that can be used in the present invention refer to stem cells that can differentiate into tissues and cells having various different morphologies and functions of the living body and have the ability to differentiate into cells of any lineage of the three germ layers (endoderm, mesoderm, and ectoderm). Examples thereof include, but not specifically limited to, embryonic stem cells (ESCs), embryonic stem cells derived from cloned embryos obtained by nuclear transplantation, sperm stem cells, embryonic germ cells, and induced pluripotent stem cells (hereinafter also referred to as "iPSCs").

Further, "multipotent stem cells" that can be used in the present invention refer to stem cells having the ability to differentiate into cells of a limited number of lineages. Examples of "multipotent stem cells" that can be used in the present invention include somatic stem cells derived from dental pulp stem cells, oral mucosa-derived stem cells, hair follicle stem cells, culture fibroblasts, and bone marrow stem cell. Preferred pluripotent stem cells are ESCs and iPSCs.

"Induced pluripotent stem cells (iPSCs)" refer to cells obtained by introducing a specific factor (nuclear reprogramming factor) into mammalian somatic cells or undifferentiated stem cells and reprogramming the cells. Currently, there are various types of "induced pluripotent stem cells". Other than iPSCs established by introducing four factors of Oct3/4, Sox2, Klf4, and c-Myc into mouse fibroblasts by Yamanaka, et al. (Takahashi K, Yamanaka S., Cell, (2006) 126:663-676), human cell-derived iPSCs established by introducing the same four factors into human fibroblasts (Takahashi K, Yamanaka S., et al. Cell, (2007) 131:861-872.), Nanog-iPS cells established by introducing the four factors and then sorting the cells using expression of Nanog as an index (Okita, K., Ichisaka, T., and Yamanaka, S. (2007). Nature 448, 313-317.), iPS cells produced by a method excluding c-Myc (Nakagawa M, Yamanaka S., et al. Nature Biotechnology, (2008) 26, 101-106), and iPS cells established by introducing six factors by a virus-free method (Okita K et al. Nat. Methods 2011 May; 8 (5): 409-12, Okita K et al. Stem Cells. 31 (3): 458-66.) can also be used. Further, induced pluripotent stem cells, produced by Thomson, et al., established by introducing four factors of OCT3/4, SOX2, NANOG, and LIN28 (Yu J., Thomson J A. et al., Science (2007) 318:1917-1920.), induced pluripotent stem cells produced by Daley, et al. (Park I H, Daley G Q. et al., Nature (2007) 451:141-146), induced pluripotent stem cells produced by Sakurada, et al. (JP 2008-307007), and the like can also be used. Other than above, any of the induced pluripotent stem cells known in the art described in all the published papers (such as Shi Y., Ding S., et al., Cell Stem Cell, (2008) Vol 3, Issue 5, 568-574; Kim J B., Scholer H R., et al., Nature, (2008) 454, 646-650; and Huangfu D., Melton, D A., et al., Nature Biotechnology, (2008) 26, No 7, 795-797) or patents (such as JP 2008-307007, JP 2008-283972, US 2008-2336610, US 2009-047263, WO 2007-069666, WO 2008-118220, WO 2008-124133, WO 2008-151058, WO 2009-006930, WO 2009-006997, and WO 2009-007852) can also be used.

As "induced pluripotent stem cells", various iPSC lines established by NIH, Institute of Physical and Chemical Research (RIKEN), Kyoto University, etc., can be used. Examples of human iPSC lines include HiPS-RIKEN-1A line, HiPS-RIKEN-2A line, HiPS-RIKEN-12A line and Nips-B2 line by RIKEN, and 253G1 line, 201B7 line, 409B2 line, 454E2 line, 606A1 line, 610B1 line and 648A1 line by Kyoto University. Alternatively, clinical grade cell lines provided by Kyoto University, Cellular Dynamics International, or the like, and cell lines for research and clinical use produced using such cell lines may be used.

As "embryonic stem cells (ESCs)", mouse ESCs such as various mouse ESC lines established by inGenious targeting laboratory, RIKEN (Institute of Physical and Chemical Research), and the like can be used, and human ESCs such as various human ESC lines established by NIH, Institute of Physical and Chemical Research, Kyoto University, and Cellartis can be used. For example, human ESC lines such as CHB-1 to CHB-12 lines, RUES1 line, RUES2 line and HUES1 to HUES28 lines by NIH, H1 line and H9 line by WisCell Research, and KhES-1 line, KhES-2 line, KhES-3 line, KhES-4 line, KhES-5 line, SSES1 line, SSES2 line and SSES3 line by RIKEN can be used. Alternatively, clinical grade cell lines, and cell lines for research and clinical use produced using such cell lines may be used.

The term "comprise(s) or comprising" means to include the elements following the term, but be not limited to the elements. Accordingly, inclusion of the elements following the term is suggested, but exclusion of any other elements is not suggested. The term "consist(s) of or consisting of" means to include all the elements following the term, and be limited to the elements. Accordingly, the term "consist(s) of or consisting of" indicates that the listed elements are required or indispensable, and other elements do not exist substantially. The term "consist(s) essentially of or consisting essentially of" means to include any element following the term, and other elements are limited to those which do not affect the activity or action of the element specified in the present disclosure. Accordingly, the term "consist(s) essentially of or consisting essentially of" indicates that the listed elements are required or indispensable, but other elements are optionally selected and may or may not exist depending on whether or not the other elements affect the activity or action of the listed elements.

The combination of the predetermined cytokine and chemokine of the present invention can provide CAR-expressing immune cells with high antitumor activity by transferring the genes into immune cells, especially T cells responsible for cell-mediated immunity of acquired immunity, and NK cells, monocytes, macrophages, and dendritic cells, which are responsible for natural immunity, together with a CAR gene and expressing the genes. In other words, gene transfer and expression of the combination of the predetermined cytokine and chemokine of the present invention can impart further technical characteristics to T cells (CAR-T cells), NK cells (CAR-NK cells), monocytes (CAR-monocytes), macrophages (CAR-macrophages), and dendritic cells (CAR-dendritic cells) in which a CAR gene is transferred and expressed.

"Immune cells" are not specifically limited, as long as they are cells having the ability to damage target cells (pathogenic cells) such as cancer cells by some mechanism of action (so-called immunity effector cells). Examples thereof include T cells responsible for cell-mediated immunity of acquired immunity, and NK cells, monocytes, macrophages, and dendritic cells, which are responsible for natural immunity. In one preferred embodiment, immune cells can be T cells. In another preferred embodiment, immune cells can be cells responsible for natural immunity such as NK cells, macrophages, and dendritic cells. It is considered that, while T cells have a considerable risk of causing GVHD by allogeneic (allo) transplantation even in the case where the HLA type matches, allo NK cells do not cause GVHD. Accordingly, off-the-shelf use is enabled by preparing various HLA types of allo-immune cells. CAR-NK cells are described, for example, in US 2016/0096892, Mol Ther. 25 (8): 1769-1781 (2017), etc., and CAR-dendritic cells, CAR-macrophages, etc., are described, for example, in WO 2017/019848, eLIFE. 2018 e36688, etc.

Hereinafter, the present invention will be described with reference to embodiments adopting T cells as a representative example of immune cells. However, the present invention is not limited only to the embodiments in which the immune cells are T cells, and the present invention also includes embodiments in which the immune cells are NK cells, monocytes, macrophages, dendritic cells, or the like. In the following description, "(CAR-) T cells" can be appropriately read as "(CAR-) NK cells", "(CAR-) monocytes", "(CAR-) macrophages", "(CAR-) dendritic cells", or the like.

Hereinafter, the T cell of the present invention will be described in detail.

The T cell of the present invention expresses: (1) a CAR; (2) at least one selected from the group consisting of IL-15, IL-18, IL-21, and IL-27; and (3) CCL19.

The T cell of the present invention may be any T cells such as αβ T cells, γδ T cells, $CD8^+$ T cells, $CD4^+$ T cells, tumor infiltrating T cells, memory T cells, naive T cells, and NK T cells, like T cells expressing common or known CARs.

The T cell may be isolated and purified from immune cells infiltrating into body fluids such as blood and bone marrow fluid, tissues such as spleen, thymus, lymph nodes, or cancer tissues such as primary tumors, metastatic tumors, and cancerous ascites. Further, the T cell may be obtained by culturing induced pluripotent stem cells (iPS cells), embryonic stem cells (ES cells), other stem cells, progenitor cells, or the like, under appropriate conditions and thereby inducing and differentiating such cells into T cells.

The T cell may be derived from humans or may be derived from mammals other than humans (non-human mammals). Examples of non-human mammals include mice, rats, hamsters, guinea pigs, rabbits, dogs, cats, pigs, cows, horses, sheep, and monkeys.

(1) CAR

The CAR expressed by the T cell of the present invention is basically constituted by peptides at the sites of (i) a single-chain antibody that recognizes a cell surface antigen of cancer cells, (ii) a transmembrane domain, and (iii) a signaling domain that induces T cell activation, which are linked via spacers, as needed, like common or known CARS.

The single-chain antibody (i) that recognizes a cell surface antigen of cancer cells is typically a single-chain variable fragment (scFv) composed of a light-chain variable region and a heavy-chain variable region derived from antigen-binding sites of a monoclonal antibody that specifically binds to the antigen and a linker peptide that links such regions.

The "cell surface antigen of cancer cells" targeted by the CAR may be a biomolecule that is specifically expressed in cancer cells and their progenitor cells, a biomolecule that has been newly expressed by canceration of cells, or a biomolecule with an increased expression level in cancer cells as compared with normal cells. Such an antigen is generally referred to as "tumor-associated antigen" (TAA), and examples thereof can include BCMA, B7-H3, B7-H6, CD7, CD10, CD19, CD20, CD22, CD23, CD24, CD30, CD33, CD34, CD38, CD41, CD44, CD56, CD70, CD74, CD97, CD123, CD133, CD138, CD171, CD248, CAIX, CEA, c-Met, CS1 (CD319), CSPG4, CLDN6, CLD18A2, CYP1B1, DNAM-1, GD2, GD3, GM2, GFRα4, GPC3, GPR20, GPRC5D, globoH, Gp100, GPR20, GPRC5D, EGFR, EGFRvariant, EpCAM, EGP2, EGP40, FAP, FITC, HER2, HER3, HPV E6, HPV E7, hTERT, IgG κ chain, IL-11Ra, IL-13Ra2, KIT, Lewis A, Lewis Y, Legumain, LMP1, LMP2, Ly6k, LICAM, MAD-CT-1, MAD-CT-2, MAGE-A1, Melanoma-associated antigen 1, MUC1, MUC16, NA-17, NY-BR-1, NY-ESO-1, O-acetyl-GD2, h5T4, PANX3, PDGRFb, PLAC1, Polysialic acid, PSCA, PSMA, RAGE1, ROR1, sLe, SSEA-4, TARP, TAG-72, TEM7R, Tn antigen, TRAIL receptor, TRP2, TSHR, α fetoprotein, mesothelin, folic acid receptor α (FRα), folic acid receptor β (FRβ), FBP, UPK2, VEGF-R2, and WT-1, but is not limited to these examples.

The transmembrane domain (ii) is a polypeptide serving as a region for fixing the CAR to the cell membrane of T cells. Examples of the transmembrane domain can include BTLA, CD3ε, CD4, CD5, CD8, CD9, CD16, CD22, CD28, CD33, CD37, CD45, CD64, CD80, CD86, CD134, CD137, CD154, 4-1BB (CD137), CTLA-4, GITR, ICOS, LAG3, OX40, SLAMF4 (CD244, 2B4), or transmembrane domains derived from the α or β chain of a T cell receptor. Alternatively, mutant transmembrane domains having an amino acid sequence with a homology of 80% or more, 85% or more, 90% or more, 91% or more, 92% or more, 93% or more, 94% or more, 95% or more, 96% or more, 97% or more, 98% or more, or 99% or more, to the natural amino acid sequence of the aforementioned transmembrane domain can also be used. In one embodiment of the present invention, the transmembrane domain of CD8 is preferable as such a transmembrane domain.

To the transmembrane domain, a hinge region which is a peptide (oligopeptide or polypeptide), consisting of any amino acid sequence, having a length of 1 to 100 amino acids, preferably 10 to 70 amino acids may be linked. Examples of the hinge region can include hinge regions derived from CD3, CD8, KIR2DS2, or IgG4, IgD or other immunoglobulins. Alternatively, mutant hinge regions having an amino acid sequence with a homology of 80% or more, 85% or more, 90% or more, 91% or more, 92% or more, 93% or more, 94% or more, 95% or more, 96% or more, 97% or more, 98% or more, or 99% or more, to the natural amino acid sequences of the aforementioned hinge regions can also be used. In one embodiment of the present invention, the hinge region of CD8 is preferable as such a hinge region.

The signaling domain (iii) that induces T cell activation is a polypeptide serving as a region for transmitting signals within T cells when the single-chain antibody recognizes the cell surface antigen of cancer cells and binds thereto. Examples of the signaling domain can include one or more intracellular domains selected from the group consisting of MHC class I molecules, TNF receptor proteins, immunoglobulin-like proteins, cytokine receptors, integrins, activated NK cell receptors, Toll-like receptors, B7-H3, BAFFR, BTLA, BY55 (CD160), CD2, CD3ζ, CD4, CD7, CD8a, CD8β, CD11a, CD11b, CD11c, CD11d, CD18, CD19, CD19a, CD27, CD28, CD29, CD30, CD40, CD49a, CD49D, CD49f, CD69, CD84, CD96 (Tactile), CD103, 4-1BB (CD137), CDS, CEACAM1, CRTAM, CNAM1 (CD226), DAP10, Fc Receptor-associated γchain, GADS, GITR, HVEM (LIGHTR), IA4, ICAM-1, ICOS (CD278), IL2Rβ, IL2Rγ, IL7Rα, ITGA4, ITGA6, ITGAD, ITGAE, ITGAL, ITGAM, ITGAX, ITGB1, ITGB2, ITGB7, KIRDS2, Ly9 (CD229), LAT, LFA-1 (CD11a/CD18), LIGHT, LTBR, NKG2C, NKG2D, NKp30, NKp44, NKp46, NKp80 (KLRF1), OX40, PAG/Cbp, PSGL1, SELPLG (CD162), SEMA4D (CD100), SLAM (SLAMF1, CD150, IPO-3), SLAMF4 (CD244, 2B4), SLAMF6 (NTB-A, Ly108), SLAMF7, SLAMF8 (BLAME), SLP-76, TNFR2, TRANCE/RANKL, VLA1, and VLA-6. Alternatively, mutant signaling domains (intracellular domains) having an amino acid sequence with a homology of 80% or more, 85% or more, 90% or more, 91% or more, 92% or more, 93% or more, 94% or more, 95% or more, 96% or more, 97% or more, 98% or more, or 99% or more, to the natural amino acid sequence of the aforementioned signaling domain (intracellular domain) can also be used. In one embodiment of the present invention, the signaling domain preferably contains three intracellular domains, CD28, 4-1BB, and CD3ζ.

In the case where the signaling domain contains a plurality of intracellular domains, the intracellular domains may be linked to each other via linker peptides (oligopeptides or polypeptides) consisting of 2 to 10 amino acids. Examples of such linker peptides can include a peptide consisting of a glycine-serine contiguous sequence.

Each between the single-chain antibody and the transmembrane domain, and between the transmembrane domain and the signaling domain, a spacer region which is a peptide (oligopeptide or polypeptide) consisting of any amino acid sequence, having a length of 1 to 100 amino acids, preferably 10 to 50 amino acids may be included. Examples of the spacer region can include a peptide consisting of a glycine-serine contiguous sequence.

The amino acid sequence of the aforementioned CAR expressed by the T cell of the present invention may be appropriately set depending on the application of the T cell, typically, its functions as an active component of a medicament for treating cancer. As the amino acid sequence of the single-chain antibody (i) against the cell surface antigen of cancer cells, various amino acid sequences are known, and information on such amino acid sequences can also be used in the present invention. Alternatively, a new antibody against the cell surface antigen of desired cancer cells may be produced according to a conventional method, and information obtained by determining the amino acid sequence of the new antibody (preferably heavy-chain and light-chain variable regions, especially CDRs) may be used in the present invention. Further, various amino acid sequences derived from humans and mammals other than humans are known as the amino acid sequences of the transmembrane domain (ii) and the T cell activation signaling domain (iii), and such amino acid sequences are also registered in databases such as NCBI (National Center for Biotechnology Information; http://www.ncbi.nlm.nih.gov/guide/), and UniProt (The Universal Protein Resource; https://www.uniprot.org). Therefore, such information can also be used in the present invention.

(2) Cytokine

The cytokine expressed by the T cell of the present invention is at least one selected from the group consisting of IL-15, IL-18, IL-21, and IL-27. The T cell of the present invention may express any one of the aforementioned four cytokines or two or more of them.

IL-15 is a cytokine having functions related to T cell survival and activation, differentiation into memory T cells, NK cell activation, and the like. The term "IL-15" in the present invention includes not only full-length natural IL-15 protein but also various embodiments as long as the functions of IL-15 in the action and effect of the present invention are retained. That is, "IL-15" in the present invention includes not only the entire protein (polypeptide) consisting of the amino acid sequence of the natural IL-15, but also a part thereof (functional partial polypeptide) and variants of the whole or a part of the natural IL-15 in which one or a plurality of amino acid sequences are deleted, replaced or added to the natural amino acid sequence (preferably, within the range having the later-described homology), and further the whole or a part of the natural IL-15 or variants thereof linked to other proteins to form a fusion protein (e.g., those linked to the whole or a part of IL-15Rα to form a fusion protein). In the present invention, the state that the T cell "expresses IL-15" includes expressing IL-15 in various forms as described above (the whole or a part of a protein having the natural amino acid sequence or variants thereof which may or may not be in the form of fusion proteins), as long as the action and effect of the present invention are not lost.

Examples of IL-15 include the following four embodiments. All of these are known (see Non Patent Literature 2, Non Patent Literature 3, Non Patent Literature 4, and Patent Literature 4 above). However, IL-15 that can be used in the present invention is not limited to these specific examples, and various IL-15 modified according to the presence or absence and types of signal peptides and linkers in sequences, the order of elements, and other viewpoints (hereinafter also referred to also as "modified" IL-15) can also be used.

First Embodiment of IL-15: IL-15LSP/IL-15 (Hereinafter Also Referred to as "$IL15_{LSP}$")

The "IL-15LSP" is a long-chain signal peptide consisting of 29 amino acids and binds to the N-terminal side of IL-15 in the first embodiment. Expression of the IL-15 of the first embodiment enhances the antitumor activity of the CAR-T cells. The term "IL-15LSP" also includes not only the entire polypeptide consisting of the amino acid sequence of the natural IL-15LSP, but also a part thereof (functional partial polypeptide) and variants of the whole or a part of the natural IL-15LSP in which one or a plurality of amino acid sequences are deleted, replaced or added to the natural amino acid sequence (preferably, within the range having the later-described homology). As an example of the modified type of the first embodiment, "IL-15LSP" replaced with "IL-2SP" (a signal peptide of IL-2, which may be the whole or a part of the natural protein or variants thereof, like IL-15LSP) can be mentioned.

Second Embodiment of IL-15: IL-15/IL-15Rα Extracellular Domain (Hereinafter Also Referred to as "$_{s}$IL15$_{RA}$")

The "IL-15Rα extracellular domain" refers to a part of IL-15Rα (interleukin 15 receptor α chain) excluding the transmembrane domain and the intracellular domain. The IL-15Rα extracellular domain includes a sushi domain (motif common to various binding proteins). The term "IL-15Rα extracellular domain" also includes not only the entire polypeptide consisting of the amino acid sequence of the natural IL-15Rα extracellular domain, but also a part thereof (functional partial polypeptide) and variants of the whole or a part of the natural IL-15Rα in which one or a plurality of amino acid sequences are deleted, replaced or added to the natural amino acid sequence (preferably, within the range having the later-described homology). In the second embodiment, the IL-15Rα extracellular domain normally binds to the C-terminal side of IL-15 via a linker (e.g., a glycine-serine linker consisting of 26 amino acids). In the second embodiment, IL-2SP (a signal peptide of IL-2, which may be the whole or a part of the natural protein or variants thereof) normally binds to the N-terminal side of IL-15 instead of IL-15LSP. The second embodiment is of a secretory type and is an agonist that strongly binds to IL-15Rβ (interleukin 15 receptor β chain shared by the interleukin 2 receptor) and γc (a common γ chain shared as a receptor of interleukin 2, 4, 7, 9, 15, 21, or the like).

Third Embodiment of IL-15: IL-15/Full-Length IL-15Rα (Hereinafter Also Referred to as "$_{mb}$IL15$_{RA}$")

The "full-length IL-15Rα" includes all of the extracellular domain, the transmembrane domain, and the intracellular domain of IL-15Rα and normally binds to the C-terminal side of IL-15 via a linker (e.g., a glycine-serine linker consisting of 20 amino acids) in the third embodiment. The term "full-length IL-15Rα" also includes not only the entire protein (polypeptide) consisting of the amino acid sequence of the full-length natural IL-15Rα, but also variants of the full-length natural IL-15Rα in which one or a plurality of amino acid sequences are deleted, replaced or added to the natural amino acid sequence (preferably, within the range having the later-described homology). Further, IL-2SP (which may be the whole or a part of the natural protein or variants thereof) normally binds to the N-terminal side of IL-15 instead of IL-15LSP also in the third embodiment. The third embodiment is of a membrane-bound type, and expression thereof enhances the antitumor activity of the CAR-T cells.

Fourth Embodiment of IL-15: IL-15RαSushi/IL-15 (Hereinafter Also Referred to as "Sushi IL15")

In the fourth embodiment, IL-15Rα containing a signal peptide and a sushi domain normally binds to the N-terminal side of IL-15 via a linker (e.g., a linker consisting of 20 amino acids). The term "IL-15Rαsushi" also includes not only the entire polypeptide consisting of the amino acid sequence of the natural IL-15Rαsushi, but also a part thereof (functional partial polypeptide) and variants of the whole or a part of the natural IL-15Rαsushi in which one or a plurality of amino acid sequences are deleted, replaced or added to the natural amino acid sequence (preferably, within the range having the later-described homology). The fourth embodiment is of a secretory type.

In the present invention, IL-15 is preferably IL-15 (the whole or a part of a protein having the natural amino acid sequence or variants thereof) in the form of a fusion protein with IL-15Rα (the whole or a part of a protein having the natural amino acid sequence or variants thereof) in view of the persistence and proliferation of cells as described in Examples (Experimental Examples) below. For example, the aforementioned second, third, or fourth embodiments or their modified types are preferable, and the aforementioned third and fourth embodiments or their modified types are more preferable.

IL-18 is a cytokine having functions related to T cell activation, NK cell activation, dendritic cell activation, and the like. The term "IL-18" in the present invention includes not only the full-length natural IL-18 protein but also various embodiments as long as the functions of IL-18 in the action and effect of the present invention are retained. That is, "IL-18" in the present invention includes not only the full-length protein (polypeptide) consisting of the amino acid sequence of the natural IL-18, but also a part thereof (functional partial polypeptide) and variants of the whole or a part of the natural IL-18 in which one or a plurality of amino acid sequences are deleted, replaced or added to the natural amino acid sequence (preferably, within the range having the later-described homology), and further the whole or a part of natural IL-18 linked to other proteins to form a fusion protein. In the present invention, the term "express IL-18" in the context of T cell includes expressing IL-18 in various forms as described above (the whole or a part of a protein having the natural amino acid sequence or variants thereof which may or may not be in the form of fusion proteins), as long as the action and effect of the present invention are not lost.

IL-21 is a cytokine having functions related to the functions of $CD8^{+}$ T cells, differentiation of $CD8^{+}$ T cells into memory T cells, NK cell survival, and the like. The term "IL-21" in the present invention includes not only the full-length natural IL-21 protein but also various embodiments as long as the functions of IL-21 in the action and effect of the present invention are retained. That is, "IL-21" in the present invention includes not only the full-length protein (polypeptide) consisting of the amino acid sequence of the natural IL-21, but also a part thereof (functional partial polypeptide) and variants of the whole or a part of the natural IL-21 in which one or a plurality of amino acid sequences are deleted, replaced or added to the natural amino acid sequence (preferably, within the range having the later-described homology), and further the whole or a part of natural IL-21 linked to other proteins to form a fusion protein. In the present invention, the term "express IL-21" in the context of T cell includes expressing various forms of IL-21 as described above (the whole or a part of a protein having the natural amino acid sequence or variants thereof which may or may not be in the form of fusion proteins), as long as the action and effect of the present invention are not lost.

IL-27 is a cytokine having functions related to T cell survival, NK cell activation, inhibition of tumor proliferation and angiogenesis, and the like. The term "IL-27" in the present invention includes not only the full-length natural IL-27 protein but also various embodiments as long as the functions of IL-27 in the action and effect of the present invention are retained. That is, "IL-27" in the present invention includes not only the full-length protein (polypeptide) consisting of the amino acid sequence of the natural IL-27, but also a part thereof (functional partial polypeptide) and variants of the whole or a part of the natural IL-27 in which one or a plurality of amino acid sequences are deleted, replaced or added to the natural amino acid sequence (preferably, within the range having the later-described homology), and further the whole or a part of natural IL-27 linked to other proteins to form a fusion protein. In the present invention, the term "express IL-27" in the context of T cell includes expressing IL-27 in various forms as described above (the whole or a part of a protein having the natural amino acid sequence or variants thereof which may or may not be in the form of fusion proteins), as long as the action and effect of the present invention are not lost.

Examples of IL-27 include a fusion protein (single-chain protein) in which p28 and EBI3 (Epstein-Barr virus-induced gene 3), which are two sub-units constituting IL-27, are linked by a linker, e.g., a linker consisting of 20 to 30 amino acids such as $(G_4S)_3$ (see Non Patent Literature 5 above, for example) or a linker consisting of GSTSGSGKPGSGEGSTKG (J Immunol. 183, 6217-26 (2009)). The terms "p28" and "EBI3" each also include the whole or a part of a polypeptide with the natural amino acid sequence or variants thereof.

The amino acid sequences of the aforementioned cytokines expressed by the T cell of the present invention may be appropriately set depending on the application of the T cell (CAR-T cell) of the present invention, typically, its functions as an active component of a medicament for treating cancer in consideration of the effect of CAR-T cells on enhancement of antitumor activity including improvement in persistence and proliferation of the CAR-T cells. The amino acid sequences of natural IL-15, IL-18, IL-21, IL-27, and IL-15Rα derived from humans and mammals other than humans (e.g., mice) are known and also registered in databases such as NCBI and UniProt, and therefore information thereof can be used also in the present invention. For example, SEQ ID NO: 18 shows the amino acid sequence of natural human IL-15 (the full length including signal peptide and propeptide parts) registered as UniProtKB-P40933, and SEQ ID NO: 19 shows the amino acid sequence of natural human IL-15Rα (the full length including a signal peptide, the sushi domain, the extracellular domain, etc.) registered as UniProtKB-Q13261. In the later-described embodiment in which a natural mouse amino acid sequence is replaced with a natural human amino acid sequence in the amino acid sequence of a predetermined sequence ID number, the amino acid sequences of corresponding parts included in SEQ ID NOs: 18 and 19 can be referred to. Further, various variants, fusion proteins with other proteins, and their modified types of IL-15, IL-18, IL-21, IL-27, and IL-15Rα are known, and information on their amino acid sequences can be used also in the present invention.

Examples of variants of IL-15, IL-18, IL-21, and IL-27 include those having an amino acid sequence with a homology of 80% or more, 85% or more, 90% or more, 91% or more, 92% or more, 93% or more, 94% or more, 95% or more, 96% or more, 97% or more, 98% or more, or 99% or more, as a whole or a partial region (domain), to their natural amino acid sequences derived from humans or mammals other than humans, for example, in the case where the signal peptide is replaced as shown below, as the homology of the region excluding the signal peptide. As a variant having a homology within such a range to a natural amino acid sequence derived from one species, a natural amino acid sequence derived from another species may be applicable (substantially included). Further, the signal peptide in the sequence of each of IL-15, IL-18, IL-21, and IL-27 may be replaced with a known signal peptide. In one aspect of the present invention, the amino acid sequence of natural mouse IL-15, IL-18, IL-21, or IL-27 can be replaced with the amino acid sequence of a variant having such a homology, the amino acid sequence of natural human IL-15, IL-18, IL-21, or IL-27 that is substantially applicable to such a variant, or a further variant thereof in the amino acid sequences of proteins (polypeptides) expressed by the nucleotide sequences of SEQ ID NO: 4: $IL15_{LSP}$_F2A_CCL19 DNA fragment (DNA fragment #3), SEQ ID NO: 6: $_{s}IL15_{RA}$_F2A_CCL19 DNA fragment (DNA fragment #4), SEQ ID NO: 8: $_{mb}IL15_{RA}$_F2A_CCL19 DNA fragment (DNA fragment #5), SEQ ID NO: 10: $_{sushi}IL15$_F2A_CCL19 DNA fragment (DNA fragment #6), SEQ ID NO: 12: IL-18_F2A_CCL19 DNA fragment (DNA fragment #7), SEQ ID NO: 14: IL-21_F2A_CCL19 DNA fragment (DNA fragment #8), and SEQ ID NO: 16: $_{sc}IL27$_F2A_CCL19 DNA fragment (DNA fragment #9), or in the amino acid sequences of a fusion protein containing SEQ ID NO: 5: $IL15_{LSP}$, a fusion protein containing SEQ ID NO: 7: $_{s}IL15_{RA}$, a fusion protein containing SEQ ID NO: 9: $_{mb}IL15_{RA}$, a fusion protein containing SEQ ID NO: 11: $_{sushi}IL15$, a fusion protein containing SEQ ID NO: 13: IL-18, a fusion protein containing SEQ ID NO: 15: IL-21, and a fusion protein containing SEQ ID NO: 17: $_{sc}IL27$.

Examples of variants of the IL-15Rα extracellular domain, the full-length IL-15Rα, and the IL-15Rαsushi include those having an amino acid sequence with a homology of 80% or more, 85% or more, 90% or more, 91% or more, 92% or more, 93% or more, 94% or more, 95% or more, 96% or more, 97% or more, 98% or more, or 99% or more, to their natural amino acid sequences derived from humans or mammals other than humans. In one aspect of the present invention, the amino acid sequence of the natural mouse IL-15Rα extracellular domain, full-length IL-15Rα, or IL-15Rαsushi can be replaced with the amino acid sequence of a variant having such a homology, the amino acid sequence of the natural human IL-15Rα extracellular domain, the full-length IL-15Rα or the IL-15Rαsushi that is substantially applicable to such a variant, or a further variant thereof in the amino acid sequences of proteins (polypeptides) expressed by the nucleotide sequences of SEQ ID NO: 4: $IL15_{LSP}$_F2A_CCL19 DNA fragment (DNA fragment #3), SEQ ID NO: 6: $IL15_{RA}$_F2A_CCL19 DNA fragment (DNA fragment #4), SEQ ID NO: 8: $_{mb}IL15_{RA}$_F2A_CCL19 DNA fragment (DNA fragment #5), SEQ ID NO: 10: $_{sushi}IL15$_F2A_CCL19 DNA fragment (DNA fragment #6), or in the amino acid sequences of a fusion protein containing SEQ ID NO: 5: $IL15_{LSP}$, a fusion protein containing SEQ ID NO: 7: $_{s}IL15_{RA}$, a fusion protein containing SEQ ID NO: 9: $_{mb}IL15_{RA}$, and a fusion protein containing SEQ ID NO: 11: $_{sushi}IL15$.

IL-15, IL-18, IL-21, and IL-27 are preferably derived from humans or mammals other than humans (e.g., mice) of the same type as those from which the T cell (or IL-15, IL-18, IL-21, and IL-27 receptors of the T cell) used for producing the T cell of the present invention is derived. Parts other than IL-15, IL-18, IL-21, and IL-27 (e.g., IL-15Rα)

contained in the fusion proteins of IL-15, IL-18, IL-21, and IL-27, respectively, are also preferably derived from humans or mammals other than humans of the same type as those from which the T cell used for producing the T cell of the present invention is derived. In one aspect of the present invention, the amino acid sequence of natural mouse IL-15, IL-18, IL-21, or IL-27 or the amino acid sequence of the IL-15Rα extracellular domain, the full-length IL-15Rα, or the IL-15Rαsushi can be replaced with the natural human amino acid sequence thereof in the amino acid sequences of proteins (polypeptides) expressed by the nucleotide sequences of SEQ ID NO: 4: $IL15_{LSP}$_F2A_CCL19 DNA fragment (DNA fragment #3), SEQ ID NO: 6: $_{s}IL15_{RA}$_F2A_CCL19 DNA fragment (DNA fragment #4), SEQ ID NO: 8: $_{mb}IL15_{RA}$_F2A_CCL19 DNA fragment (DNA fragment #5), SEQ ID NO: 10: $_{sushi}IL15$_F2A_CCL19 DNA fragment (DNA fragment #6), SEQ ID NO: 12: IL-18_F2A_CCL19 DNA fragment (DNA fragment #7), SEQ ID NO: 14: IL-21_F2A_CCL19 DNA fragment (DNA fragment #8), SEQ ID NO: 16: $_{sc}IL27$_F2A_CCL19 DNA fragment (DNA fragment #9), or in the amino acid sequences of a fusion protein containing SEQ ID NO: 5: $IL15_{LSP}$, a fusion protein containing SEQ ID NO: 7: $_{s}IL15_{RA}$, a fusion protein containing SEQ ID NO: 9: $_{mb}IL15_{RA}$, a fusion protein containing SEQ ID NO: 11: $_{sushi}IL15$, a fusion protein containing SEQ ID NO: 13: IL-18, a fusion protein containing SEQ ID NO: 15: IL-21, and a fusion protein containing SEQ ID NO: 17: $_{sc}IL27$.

(3) Chemokine

The chemokine expressed by the T cell of the present invention is CCL19. CCL19 is mainly produced from dendritic cells and macrophages of lymph nodes and has a function of inducing migration of T cells, B cells, and mature dendritic cells via their receptor, CCR7. That is, "CCL19" in the present invention includes not only the full-length protein (polypeptide) consisting of the amino acid sequence of the natural CCL19, but also a part thereof (functional partial polypeptide) and variants of the whole or a part of the natural CCL19 in which one or a plurality of amino acid sequences are deleted, replaced or added to the natural amino acid sequence (preferably, within the range having the later-described homology).

The amino acid sequence of the aforementioned chemokine expressed by the T cell of the present invention may be appropriately set depending on the application of the T cell (CAR-T cell) of the present invention, typically, its functions as an active component of a medicament for treating cancer in consideration of the effect of the CAR-T cell on enhancement of antitumor activity including improvement in persistence and proliferation of the CAR-T cell. The amino acid sequences of natural CCL19 derived from humans and mammals other than humans (e.g., mice) are known and also registered in databases such as NCBI and UniProt, and therefore information thereof can be used also in the present invention. Further, information on the amino acid sequences of known variants of CCL19 can also be used in the present invention.

Examples of the variants of CCL19 include those having an amino acid sequence with a homology of 80% or more, 85% or more, 90% or more, 91% or more, 92% or more, 93% or more, 94% or more, 95% or more, 96% or more, 97% or more, 98% or more, or 99% or more, as a whole or a partial region, to the amino acid sequences of the natural CCL19 derived from humans or mammals other than humans. In one aspect of the present invention, the amino acid sequence of natural mouse CCL19 can be replaced with the amino acid sequence of a variant having such a homology, the amino acid sequence of natural human CCL19 that is substantially applicable to such a variant, or a further variant thereof in the amino acid sequences of proteins (polypeptides) expressed by the nucleotide sequences of SEQ ID NO: 4: $IL15_{LSP}$_F2A_CCL19 DNA fragment (DNA fragment #3), SEQ ID NO: 6: $_{s}IL15_{RA}$_F2A_CCL19 DNA fragment (DNA fragment #4), SEQ ID NO: 8: $_{mb}IL15_{RA}$_F2A_CCL19 DNA fragment (DNA fragment #5), SEQ ID NO: 10: $_{sushi}IL15$_F2A_CCL19 DNA fragment (DNA fragment #6), SEQ ID NO: 12: IL-18_F2A_CCL19 DNA fragment (DNA fragment #7), SEQ ID NO: 14: IL-21_F2A_CCL19 DNA fragment (DNA fragment #8), and SEQ ID NO: 16: $_{sc}IL27$_F2A_CCL19 DNA fragment (DNA fragment #9).

CCL19 is preferably derived from humans or mammals other than humans (e.g., mice) of the same type as the T cell used for producing the T cell of the present invention (CCL19 receptor of the T cell) or variants thereof.

Hereinafter, the medicament of the present invention will be described in detail.

The medicament of the present invention contains the T cell of the present invention as described above and may further contain other components, as required. Those skilled in the art would be able to appropriately prepare the medicament of the present invention using the T cell of the present invention in consideration of the application (treatment target) and dosage form.

The medicament of the present invention is mainly a medicament (anticancer agent) to treat cancer corresponding to the cell surface antigen of cancer cells (cancer-specific antigen) targeted by the CAR expressed by the T cell of the present invention. Accordingly, the type of cancer targeted by the medicament of the present invention is not specifically limited, as long as cancer cells expressing the antigen targeted by the CAR are contained in the cancer tissue, and a certain level of therapeutic effect is observed by the T cell of the present invention. Examples of the cancer that can be targeted by the medicament of the present invention can include cancers such as adenocarcinoma, squamous cell carcinoma, adenosquamous carcinoma, undifferentiated cancer, large cell cancer, small cell cancer, skin cancer (e.g., melanoma and Merkel cell cancer), breast cancer, prostate cancer, bladder cancer, vaginal cancer, neck cancer, head and neck cancer, uterine cancer, cervical cancer, liver cancer, kidney cancer, pancreatic cancer, spleen cancer, lung cancer, non-small cell lung cancer, tracheal cancer, bronchial cancer, colon cancer, rectal cancer, small intestine cancer, colorectal cancer, stomach cancer, esophageal cancer, gallbladder cancer, testicular cancer, ovarian cancer, fallopian tube cancer, and nasopharyngeal cancer; cancers of bone tissue, cartilage tissue, adipose tissue, muscle tissue, vascular tissue, and hematopoietic tissue; sarcomas such as chondrosarcoma, Ewing's sarcoma, rhabdomyosarcoma, malignant hemangioendothelioma, malignant tumor, osteosarcoma, and soft tissue sarcoma; blastomas such as hepatoblastoma, medulloblastoma, nephroblastoma, neuroblastoma, pancreatoblastoma, pleuropulmonary blastoma, and retinoblastoma; embryonic cell tumors; lymphoma; leukemia, acute myeloid leukemia, and multiple myeloma. Preferably, examples thereof include carcinomas sensitive to NK cells (such as melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, and leukemia). More preferably, examples thereof include melanoma, colorectal cancer, kidney cancer, multiple myeloma, lymphoma, and leukemia.

Examples of components that can be contained in the medicament of the present invention other than the T cell include pharmaceutically acceptable additives, more specifically, saline, buffered saline, cell culture media, dextrose, water for injection, glycerol, ethanol, stabilizers, solubilizers, surfactants, buffers, preservatives, isotonic agents, fillers, and lubricants.

The medicament of the present invention can be used by being administered to a subject in need of cancer treatment (such as cancer patients and cancer-bearing animals) by the same method as for known CAR-expressing T cells. Examples of the administration method include intratumor, intravenous, intraarterial, intramuscular, subcutaneous, and intraperitoneal injections.

The amount of the T cell of the present invention to be contained in the medicament of the present invention can be appropriately adjusted, for example, depending on the application, dosage form, intended therapeutic effect, and the like, in consideration of the type, location, and severity of cancer, the age, body weight, and condition of the subject to be treated, and the like. For example, the medicament of the present invention can be formulated so that the T cell of the present invention is administered in an amount of normally $1\times10^4$ to $1\times10^{10}$, preferably $1\times10^5$ to $1\times10^9$, more preferably $5\times10^6$ to $5\times10^8$, in a single dose.

The administration interval of the medicament of the present invention is not specifically limited and can be appropriately adjusted in consideration of the amount of the T cell of the present invention to be administered at one time, and the like. The medicament of the present invention can be independently administered, for example, 4 times, 3 times, twice, or once a day, every other day, every 3 days, every 4 days, every 5 days, every 6 days, once a week, every 8 days, every 9 days, every 10 days, twice a week, once a month, or twice a month.

The medicament of the present invention (anticancer agent) can be used in combination with known anticancer agents. Examples of the anticancer agents can include alkylating drugs such as cyclophosphamide, bendamustine, iosfamide, and dacarbazine; antimetabolites such as pentostatin, fludarabine, cladribine, methotrexate, 5-fluorouracil, 6-mercaptopurine, and enocitabin; molecular targeted drugs such as rituximab, cetuximab, and trastuzumab; kinase inhibitors such as imatinib, gefitinib, erlotinib, afatinib, dasatinib, sunitinib, and trametinib; proteasome inhibitors such as bortezomib; calcineurin inhibitors such as cyclosporine and tacrolimus; antitumor antibiotics such as idarubicin, doxorubicin and mitomycin C; plant alkaloids such as irinotecan and etoposide; platinum preparations such as cisplatin, oxaliplatin, and carboplatin; hormone therapeutic drugs such as tamoxifen and bicalutamide; and immunoregulatory drugs such as interferon, nivolumab, and pembrolizumab.

Use of the medicament of the present invention in combination with additional anticancer agent may be in any form of (a) using the additional anticancer agent and then the medicament of the present invention, (b) using the medicament of the present invention and the additional anticancer agent at the same time, or (c) using the medicament of the present invention and then the additional anticancer agent. When the medicament of the present invention is used in combination with the additional anticancer agent, it is expected that the therapeutic effect on cancer is more improved, and the side effects due to the anticancer agents can be reduced by reducing the number of administrations or the doses of the medicament of the present invention and/or the other anticancer agent.

Hereinafter, the expression vector of the present invention will be described in detail.

The expression vector of the present invention contains: (1) a nucleic acid encoding a CAR; (2) a nucleic acid encoding at least one selected from the group consisting of IL-15, IL-18, IL-21, and IL-27; and (3) a nucleic acid encoding CCL19.

In the present invention, the term "contain a nucleic acid encoding IL-15" in the context of expression vector includes comprising a nucleic acid encoding not only the full-length natural IL-15 protein but also IL-15 in various forms as described above. The same applies also to the term "contain a nucleic acid encoding IL-18", "contain a nucleic acid encoding IL-21", "contain a nucleic acid encoding IL-27", or "contain a nucleic acid encoding CCL19" in the context of expression vector.

The "nucleic acid" may be any molecules obtained by polymerization of nucleotides and molecules having functions equivalent to the nucleotides. Examples thereof can include RNA, which is a polymer of ribonucleotides, DNA, which is a polymer of deoxyribonucleotides, a polymer mixing ribonucleotides and deoxyribonucleotides, and a nucleotide polymer containing nucleotide analogs. Further, the nucleic acid may be a nucleotide polymer containing nucleic acid derivatives. Further, the nucleic acid may be a single-stranded nucleic acid or a double-stranded nucleic acid. Further, the double-stranded nucleic acid also includes a double-stranded nucleic acid in which one strand is hybridized with the other strand under stringent conditions.

The nucleotide analogs may be any molecules with modification of a ribonucleotide, a deoxyribonucleotide, RNA, or DNA, for improving the nuclease resistance, stabilizing, increasing the affinity with complementary strand nucleic acids, increasing the cell permeability, or visualizing cells, as compared with RNA or DNA. The nucleotide analogs may be naturally occurring molecules or non-natural molecules. Examples thereof include sugar-modified nucleotide analogs and phosphodiester bond-modified nucleotide analogs.

The sugar-modified nucleotide analogs may be any analog obtained by adding any chemical structural material to or replacing with any chemical structural material part or the whole of the chemical structure of the sugar of the nucleotide. Specific examples thereof can include nucleotide analogs replaced with 2'-O-methyl ribose, nucleotide analogs replaced with 2'-O-propyl ribose, nucleotide analogs replaced with 2'-methoxyethoxy ribose, nucleotide analogs replaced with 2'-O-methoxyethyl ribose, nucleotide analogs replaced with 2'-O-[2-(guanidinium) ethyl] ribose, nucleotide analogs replaced with 2'-fluororibose, crosslinked artificial nucleic acids having two cyclic structures by introducing crosslinked structures into the sugar part (Bridged Nucleic Acids) (BNAs), more specifically, locked artificial nucleic acids in which the oxygen atom at the 2' position and the carbon atom at the 4' position are crosslinked via methylene (Locked Nucleic Acids) (LNAs), and ethylene crosslinked artificial nucleic acids (Ethylene bridged nucleic acids) (ENAs) [Nucleic Acid Research, 32, e175 (2004)], and further include peptide nucleic acids (PNAs) [Acc. Chem. Res., 32, 624 (1999)], oxypeptide nucleic acids (OPNAs) [J. Am. Chem. Soc., 123, 4653 (2001)], and peptide ribonucleic acids (PRNAs) [J. Am. Chem. Soc., 122, 6900 (2000)].

The phosphodiester bond-modified nucleotide analogs may be any analog obtained by adding any chemical substance to or replacing with any chemical substance part or the whole of the chemical structure of the phosphodiester bond of the nucleotide. Specific examples thereof can include nucleotide analogs replaced with phosphorothioate bonds, and nucleotide analogs replaced with N3'-P5' phosphoramidite bonds [Cell technology, 16, 1463-1473 (1997)] [RNAi method and antisense method, Kodansha Ltd. (2005)].

The nucleic acid derivatives may be any molecules obtained by adding another chemical substance to the nucleic acids, for improving the nuclease resistance, stabilizing, increasing the affinity with complementary strand nucleic acids, increasing the cell permeability, or visualizing cells, as compared with the nucleic acids. Specific examples thereof can include 5'-polyamine-added derivatives, cholesterol-added derivatives, steroid-added derivatives, bile acid-added derivatives, vitamin-added derivatives, Cy5-added derivatives, Cy3-added derivatives, 6-FAM-added derivatives, and biotin-added derivatives.

The expression vector of the present invention needs only to be capable of producing the T cell of the present invention by contacting a T cell or its precursor, being introduced into the cell, and expressing a predetermined protein (polypeptide) encoded therein in the T cell. The embodiment thereof is not specifically limited. Those skilled in the art would be able to design and produce an expression vector capable of expressing a desired protein (polypeptide) in the T cell.

The expression vector of the present invention may be linear or cyclic and may be a non-viral vector such as a plasmid, a viral vector, or a transposon vector.

Examples of the viral vector can include a retroviral vector, a lentiviral vector, an adenoviral vector, and an adeno-associated viral vector. Preferable examples of the retroviral vector can include a pMSGV vector (Tamada k et al., ClinCancer Res 18:6436-6445 (2002)) and a pMSCV vector (available from Takara Bio Inc). In the case of using the retroviral vector, the genes contained in the vector are incorporated into the genome of a host cell (the T cell in the present invention), and therefore the genes can be stably expressed for a long period of time.

In one embodiment of the present invention, one expression vector contains all elements of (1) a nucleic acid encoding a CAR, (2) a nucleic acid encoding at least one selected from the group consisting of IL-15, IL-18, IL-21, and IL-27, and (3) a nucleic acid encoding CCL19. In another embodiment of the present invention, a first expression vector contains one or two of the aforementioned elements (1) to (3), and a second expression vector contains the remaining element. In another embodiment of the present invention, a first expression vector contains the aforementioned element (1), a second expression vector contains the aforementioned element (2), and a third expression vector contains the aforementioned element (3). Accordingly, the expression vector of the present invention may mean a combination (set) of a plurality of expression vectors, that is, a combination of the aforementioned first and second expression vectors or a combination of the aforementioned first, second, and third expression vectors, depending on the embodiment. In the case where one expression vector contains a plurality of elements, the order in which those elements are arranged from the upstream side to the downstream side is not particularly limited.

The nucleotide sequences of the predetermined three elements (CAR, cytokine, and chemokine) contained in the expression vector of the present invention may be designed so as to encode the amino acid sequences of proteins (polypeptides), respectively, corresponding to the proteins (polypeptides) selected as the elements. The nucleic acids (oligonucleotides) contained in the expression vector may be produced by chemically synthesizing oligo DNA or may be produced (cloned) as cDNA.

The expression vector of the present invention may contain (in the case of the aforementioned combinations of a plurality of expression vectors, the expression vectors each independently may contain) the sequences of promoters, terminators, enhancers, start codons, stop codons, polyadenylation signals, nuclear localization signals (NLS), multi-cloning sites (MCS), and the like, that are involved in the expression of each gene, as required, in addition to the sequences (genes) encoding the aforementioned predetermined elements.

In one embodiment of the present invention, in the case where one expression vector contains two or more of the aforementioned three elements, a gene encoding a self-cleaving peptide (2A peptide) or IRES (Internal Ribozyme Entry Site) may be inserted between the elements.

The 2A peptide is a self-cleaving peptide derived from a virus and has a characteristic that a predetermined position (position of one residue from the C-terminus) in the amino acid sequence is cleaved in the endoplasmic reticulum (Szymczak et al., Expert Opin. Biol. Ther. 5 (5): 627-638 (2005)). Therefore, the genes integrated before and after the 2A peptide will be expressed independently of each other in the cell. Examples of the 2A peptide include those derived from picornavirus, rotavirus, insect virus, aphthovirus, or trypanosoma virus.

The expression vector of the present invention may further contain nucleic acids (nucleotide sequences) encoding "functional genes" such as a reporter gene (typically, a gene encoding a fluorescent protein), a drug selection gene, and a suicide gene.

In the case of using a "drug resistance gene" as a functional gene, cells into which the expression vector of the present invention containing the drug resistance gene is introduced can be selected by adding a predetermined drug to the medium in the method for producing a CAR-T cell of the present invention. Examples of the drug resistance gene include a kanamycin resistance gene, an ampicillin resistance gene, and a puromycin resistance gene. One of these genes may be used, or two or more of them may be used.

In the case of using a "gene encoding a fluorescent protein" as a functional gene, T cells with the expression vector of the present invention introduced can be observed using a fluorescence microscope, or cells with the expression vector of the present invention introduced can be sorted using a flow cytometer (cell sorter), in the method for producing a CAR-T cell of the present invention. A typical example of the reporter gene is a gene encoding a fluorescent protein. Examples of the "gene encoding a fluorescent protein" include blue fluorescent proteins such as Sirius, BFP, and EBFP; cyan fluorescent proteins such as mTurquoise, TagCFP, AmCyan, mTFP1, MidoriishiCyan, and CFP; green fluorescent proteins such as TurboGFP, AcGFP, TagGFP, Azami-Green (e.g., hmAG1), ZsGreen, EmGFP, EGFP, GFP2, and HyPer; yellow fluorescent proteins such as TagYFP, EYFP, Venus, YFP, PhiYFP, PhiYFP-m, TurboYFP, ZsYellow, and mBanana; orange fluorescent proteins such as KusabiraOrange (e.g., hmKO2) and mOrange; red fluorescent proteins such as TurboRFP, DsRed-Express, DsRed2, TagRFP, DsRed-Monomer, AsRed2, and mStrawberry; and near-infrared fluorescent proteins such as TurboFP602, mRFP1, JRed, KillerRed, mCherry, HcRed, KeimaRed (e.g., hdKeimaRed), mRasberry, and mPlum. Any one of these genes may be used, or two or more of them may be used. In the case of using two or more genes encoding fluorescent proteins, the fluorescent proteins preferably have different emission wavelengths so as not to interfere with the visibility of each other.

In the case of using a "suicide gene" as a functional gene, the number of the T cells of the present invention in vivo can be controlled by administering a drug that activates the function of the suicide gene, depending on the course of cancer treatment, for example, at the stage when the tumor has disappeared. Examples of the suicide gene include a gene encoding diphtheria toxin A, herpes simplex thymidine kinase (HSV-TK), carboxypeptidase G2 (CPG2), carboxyl esterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella-zoster virus thymidine kinase (VZV-TK), xanthine-guanine phosphoribosyl transferase (XGPRT), or inducible caspase 9. Any one of these genes may be used, or two or more of them may be used. Drugs that activate the function of each suicide gene are known, and examples thereof include ganciclovir for herpes simplex thymidine kinase (HSV-TK), and AP1903 that is a dimer-inducing compound for inducible caspase 9.

Hereinafter, the method for producing a CAR-T cell of the present invention will be described in detail. The method for producing a CAR-T cell of the present invention contains a step of introducing the expression vector of the present invention into a T cell as described above (which will be hereinafter referred to as "expression vector-introducing step").

The method for introducing the expression vector into a T cell can be made suitable for the embodiment of the expression vector. For example, the expression vector can be introduced into the T cell by known methods such as a virus infection method, a calcium phosphoric acid method, a lipofection method, a microinjection method, and an electroporation method. The expression vector of the present invention can be prepared in a form suitable for use in each method by known means and by using commercially available kits as appropriate (according to the instructions thereof). In the expression vector-introducing step, T cells may be cultured by bringing such a preparation into contact with T cells, generally, in a medium to which a preparation containing the expression vector.

In a preferred embodiment of the present invention, the expression vector of the present invention is introduced into T cells by a virus infection method. For example, a method in which the vector of the present invention and the packaging vector (plasmid) of each virus are transfected into a host cell, using a commercially available kit corresponding to each viral vector such as a retroviral vector, a lentiviral vector, an adenoviral vector, and an adeno-associated viral vector, to produce a recombinant virus, and thereafter T cells are infected with the recombinant virus obtained can be mentioned. Examples of the commercially available kit for viral vectors include Retrovirus packaging Kit Eco (available from Takara Bio Inc). Examples of the host cell include GP2-293 cell (available from Takara Bio Inc.), Plat-GP cell (available from Cosmo Bio Co., Ltd.), PG13 cell (ATCC CRL-10686), and PA317 cell (ATCC CRL-9078).

The method for producing a CAR-T cell of the present invention may further contain other steps before and after the expression vector-introducing step. Examples of the other steps include a step of culturing T cells, and a step including a process to cause a functional gene contained in the expression vector to function.

The T cells into which the expression vector of the present invention is introduced can be normally pre-cultured in vitro by a known method. For example, T cells may be isolated and purified according to a conventional method from body fluids such as blood and bone marrow fluid; tissues such as spleen, thymus, and lymph nodes; or cancer tissues such as primary tumors, metastatic tumors, and cancerous ascites, which are collected from humans or nonhuman animals, and then cultured in an appropriate medium, and (a preparation containing) the expression vector of the present invention may be added to the medium. Alternatively, T cells (or precursors thereof) may be prepared in advance from iPS cells, ES cells, and other pluripotent stem cells through an appropriate differentiation-inducing step, and (a preparation containing) the expression vector of the present invention may be added to the medium.

Further, in the case where the expression vector of the present invention contains a drug resistance gene as a functional gene, a step of culturing T cells while adding a drug corresponding to the drug resistance gene used to the medium can be performed after the expression vector-introducing step, in order to sort T cells with the expression vector introduced. Those skilled in the art would be able to appropriately adjust the conditions for using the drug corresponding to the drug resistance gene such as the concentration in the medium and the culture period.

In the case where the expression vector of the present invention contains a gene encoding a fluorescent protein (reporter gene) as a functional gene, a step of observing T cells with the expression vector introduced using a fluorescence microscope, a step of sorting T cells with the expression vector introduced using a cell sorter, and the like can be performed after the expression vector-introducing step. Those skilled in the art would be able to appropriately adjust the conditions for observation using a fluorescence microscope and selection using a cell sorter, such as irradiation with light having an excitation wavelength and detection of light having an emission wavelength corresponding to the fluorescent protein.

EXAMPLES

The CAR in the following examples is a CAR targeting human CD20, specifically, an anti-human CD20 CAR consisting of anti-human CD20 scFv, mouse CD8 transmembrane domain, and mouse CD28 4-1BB_CD3ζ intracellular signal motif. Further, the cytokine in the following examples is any of mouse IL-15 ("IL15$_{LSP}$", "$_{s}$IL15$_{RA}$", "$_{mb}$IL15$_{RA}$", "or" "$_{sushi}$IL15"); mouse IL-18; mouse IL-21; or a single-chain protein "$_{sc}$IL27" containing mouse IL-27 (p28 and EBI3). The chemokine in the following examples is mouse CCL19. Mouse-derived T cells expressing the CAR, the cytokine, and the chemokine were produced as follows and tested.

TABLE 1

| Example/ Comparative Example | CAR | Cytokine | Chemokine |
|---|---|---|---|
| Example 1-1 | Anti-human CD20scFv | IL15$_{LSP}$ (Mouse) | CCL19 (Mouse) |
| Example 1-2 | Anti-human CD20scFv | $_{s}$IL15$_{RA}$ (Mouse) | CCL19 (Mouse) |

TABLE 1-continued

| Example/ Comparative Example | CAR | Cytokine | Chemokine |
|---|---|---|---|
| Example 1-3 | Anti-human CD20scFv | $_{mb}$IL15$_{RA}$ (Mouse) | CCL19 (Mouse) |
| Example 1-4 | Anti-human CD20scFv | $_{sushi}$IL15 (Mouse) | CCL19 (Mouse) |
| Example 2 | Anti-human CD20scFv | IL-18 (Mouse | CCL19 (Mouse) |
| Example 3 | Anti-human CD20scFv | IL-21 (Mouse) | CCL19 (Mouse) |
| Example 4 | Anti-human CD20scFv | $_{sc}$IL27 (Mouse) | CCL19 (Mouse) |
| Comparative Example 1 | — | — | — |
| Comparative Example 2 | Anti-human CD20scFv | — | — |

[Example 1-1] IL15$_{LSP}$×CCL19 CAR-T Cells

In a vector-producing step, three types of DNA fragments (DNA fragments 1 to 3) were first artificially synthesized in step 1, and then one expression vector containing all genes encoding the predetermined CAR, cytokine, and chemokine were produced using the three types of DNA fragments in step 2. Subsequently, in a CAR-T cell-producing step, a retroviral vector was first prepared using the expression vector in step 1, and then the predetermined genes were transduced into mouse T cells using the retroviral vector preparation in step 2.

[A: Vector-Producing Step] Production of IL15$_{LSP}$_CCL19 Anti-Human CD20 CAR Expression Vector Step 1: Synthesis of DNA Fragments DNA Fragment #1: DNA Fragment Containing Anti-Human CD20 CAR A DNA fragment (DNA fragment #1) containing a nucleotide sequence encoding anti-human CD20 CAR consisting of anti-human CD20 scFv, mouse CD8 transmembrane domain, and mouse CD28_4-1BB_CD3ζ intracellular signal motif was artificially synthesized. SEQ ID NO: 1 (FIG. 7) shows the nucleotide sequence of the entire DNA fragment #1. In SEQ ID NO: 1, the bases at positions 3 to 785 form a sequence encoding the anti-human CD20 scFv, the bases at positions 795 to 1040 form a sequence encoding the mouse CD8 transmembrane domain, the bases at positions 1041 to 1637 form a sequence encoding the mouse CD28_4-1BB_CD3ζ intracellular signal motif (among them, the bases at positions 1041 to 1163 encode the intracellular domain of mouse CD28, the bases at positions 1164 to 1298 encode the intracellular domain of mouse 4-1BB, and the bases at positions 1299 to 1637 encode the polypeptide in the intracellular domain of mouse CD3ζ). SEQ ID NO: 2 shows the amino acid sequence of the fusion protein expressed by the nucleotide sequence at positions 3 to 1637 of DNA fragment #1.

DNA Fragment #2: DNA Fragment Containing Stop Codons and Multicloning Sites

A DNA fragment (DNA fragment #2) containing the nucleotide sequence of stop codons and the nucleotide sequence of multicloning sites (MCS) was artificially synthesized. SEQ ID NO: 3 (FIG. 8) shows the nucleotide sequence of the entire DNA fragment #2.

DNA Fragment #3: DNA Fragment for IL15$_{LSP}$ and CCL19

A DNA fragment (DNA fragment #3) containing a nucleotide sequence encoding 2A peptide (F2A) that is a self-cleaving peptide, mouse IL-2 signal peptide (IL-2SP), mouse IL-15 construct "IL15$_{LSP}$" (fusion peptide consisting of IL-15LSP and IL-15), F2A, and mouse CCL19 was artificially synthesized. SEQ ID NO: 4 (FIG. 9) shows the nucleotide sequence of the entire DNA fragment #3. In SEQ ID NO: 4, the bases at positions 7 to 81 form a sequence encoding the first F2A, the bases at positions 82 to 168 form a sequence encoding mouse IL-15$_{LSP}$, the bases at positions 169 to 567 form a sequence encoding mouse IL-15 (excluding stop codons), the bases at positions 568 to 642 form a sequence encoding the second F2A, and the bases at positions 646 to 969 form a sequence encoding mouse CCL19. SEQ ID NO: 5 shows the amino acid sequence of the entire fusion protein that is expressed by the nucleotide sequence at positions 7 to 969 of DNA fragment #3, self-cleaves at two F2A sites, and contains IL15$_{LSP}$.

Step 2: Production of Retrovirus Expression Vector

DNA fragment #1 and DNA fragment #2 were linked to produce a construct (anti-human CD20 CAR_MCS). The construct obtained was incorporated into a pMSGV retrovirus expression vector (Tamada k et al., Clin Cancer Res 18:6436-6445 (2002)) by restriction enzyme (Nco I and Sal I) treatment, to produce an anti-human CD20 CAR_MCS-containing pMSGV retrovirus expression vector.

Then, the nucleotide sequence at positions 1337 to 1637 of DNA fragment #1 and DNA fragment #3 were linked to produce a construct. The construct obtained was incorporated into an anti-human CD20 CAR_MCS-containing pMSGV retroviral vector by restriction enzyme (Sbf I and Sal I) treatment, to produce an anti-human CD20 CAR_F2A_IL15$_{LSP}$_F2A_CCL19-containing pMSGV retrovirus expression vector (IL15$_{LSP}$_CCL19_anti-human CD20 CAR expression vector).

[B: CAR-T Cell-Producing Step] Production of IL15$_{LSP}$_CCL19 Anti-Human CD20 CAR-T Cells Step 1: Preparation of Retrovirus Using Lipofectamine 3000 (available from Thermo Fisher SCIENTIFIC K.K.), the IL15$_{LSP}$_CCL19_anti-human CD20 CAR expression vector obtained by the vector-producing step was transfected into GP2-293 packaging cell line (Takara Bio Inc.) together with pCL-Eco plasmid (Novus Biologicals, LLC). DMEM with 10% deactivated FBS and antibiotics added was used as a culture solution for the GP2-293 packaging cell line. 48 hours after the transfection, the supernatant of the culture solution of the GP2-293 packaging cell line was collected, to form a preparation of the IL15$_{LSP}$_CCL19_anti-human CD20 CAR expression vector.

Step 2: Transduction of Mouse T Cells $3\times10^6$ mouse T cells derived from mouse spleen and lymph nodes and purified were activated for 48 hours in the presence of an immobilized anti-mouse CD3 monoclonal antibody (3 μg/mL), an anti-mouse CD28 monoclonal antibody (1 μg/mL), and IL-2. Subsequently, the IL15$_{LSP}$_CCL19_anti-human CD20 CAR expression vector-containing preparation (GP2-293 cell culture supernatant) obtained in step 1 and mouse T cells activated as described above were mixed within the wells of a plate in which 25 μg/mL of retronectin is immobilized (registered trademark: Takara Bio Inc.), followed by centrifugation at 1500 rpm for 2 hours, and the mixture was cultured for 6 hours in the presence of IL-2. In order to remove retrovirus from the culture solution, mouse T cells were collected, transferred to a new complete RPMI medium containing IL-2, and further cultured for 42 hours, to obtain mouse T cells (IL15$_{LSP}$_CCL19_anti-human CD20 CAR-T cells, hereinafter referred to as "IL15$_{LSP}$×CCL19 CAR-T cells") with an IL15$_{LSP}$_CCL19_anti-human CD20 CAR expression vector introduced, that is, expressing an anti-human CD20 CAR, IL15$_{LSP}$, and CCL19.

The "complete RPMI medium" used for culturing the T cells was an RPMI-1640 medium to which deactivated 10% FBS, antibiotics, 50-mM 2-mercapto ethanol, and 25-mM HEPES buffer were added. A complete RPMI medium to which components separately described were further added, as required, was used below as a culture solution for the T cells.

[Example 1-2] $_{s}$IL15$_{RA}$ (Secretory IL-15/IL-15RA Fusion Protein)×CCL19 CAR-T Cells

[A: Vector-Producing Step] Production of $_{s}$IL15$_{RA}$_CCL19_Anti-Human CD20 CAR Expression Vector Using the same DNA fragment #1 and DNA fragment #2 as in step 1 of Example 1-1 and DNA fragment #4 as described below, instead of DNA fragment #3, a construct was produced in the same manner as in step 2 of Example 1-1, to obtain an anti-human CD20 CAR_F2A_$_{s}$IL15$_{RA}$_F2A_CCL19-containing pMSGV retrovirus expression vector ($_{s}$IL15$_{RA}$_CCL19_anti-human CD20 CAR expression vector).

DNA Fragment #4: DNA Fragment for $_{s}$IL15$_{RA}$ and CCL19

A DNA fragment (DNA fragment #4) containing a nucleotide sequence encoding F2A, mouse IL-2SP, a mouse IL-15 construct "$_{s}$IL15$_{RA}$" (fusion peptide consisting of IL-15, a linker, and the IL-15Rα extracellular domain), F2A, and mouse CCL19 was synthesized. SEQ ID NO: 6 (FIG. 10) shows the nucleotide sequence of the entire DNA fragment #4. In SEQ ID NO: 6, the bases at positions 7 to 81 form a sequence encoding the first F2A, the bases at positions 82 to 141 form a sequence encoding mouse IL-2SP, the bases at positions 142 to 1137 form a sequence encoding $_{s}$IL15$_{RA}$ (among them, the bases at positions 142 to 540 encode mouse IL-15 (excluding signal sequences and stop codons), the bases at positions 541 to 618 serve as a linker, and the bases at positions 619 to 1137 encode the mouse IL-15Rα extracellular domain), the bases at positions 1138 to 1212 form a sequence encoding the second F2A, and the bases at positions 1216 to 1539 form a sequence encoding mouse CCL19. SEQ ID NO: 7 shows the amino acid sequence of the entire fusion protein that is expressed by the nucleotide sequence at positions 7 to 1539 of DNA fragment #4, self-cleaves at two F2A sites, and contains $_{s}$IL15$_{RA}$.

[B: CAR-T Cell-Producing Step] Production of $_{s}$IL15$_{RA}$_CCL19_Anti-Human CD20 CAR-T Cells A retrovirus-containing preparation was obtained in step 1 in the same manner as in the CAR-T cell-producing step of Example 1-1 except that the $_{s}$IL15$_{RA}$_CCL19_anti-human CD20 CAR expression vector obtained by the aforementioned vector-producing step was used as a retrovirus expression vector, instead of the IL15$_{LSP}$_CCL19_anti-human CD20 CAR expression vector, to obtain mouse T cells expressing the genes of anti-human CD20 CAR, $_{s}$IL15$_{RA}$, and CCL19 contained in the retrovirus ($_{s}$IL15$_{RA}$_CCL19_anti-human CD20 CAR-T cells, hereinafter referred to as $_{s}$IL15$_{RA}$×CCL19 CAR-T cells) in step 2.

[Example 1-3] $_{mb}$IL15$_{RA}$ (Membrane-Bound IL-15/IL-15RA Fusion Protein)×CCL19 CAR-T Cells

[A: Vector-Producing Step] Production of $_{mb}$IL15$_{RA}$_CCL19_Anti-Human CD20 CAR Expression Vector Using the same DNA fragment #1 and DNA fragment #2 as in step 1 of Example 1-1 and DNA fragment #5 as described below, instead of DNA fragment #3, a construct was produced in the same manner as in step 2 of Example 1-1, to obtain an anti-human CD20 CAR_F2A_$_{mb}$IL15$_{RA}$_F2A_CCL19-containing pMSGV retrovirus expression vector ($_{mb}$IL15$_{RA}$_CCL19_anti-human CD20 CAR expression vector).

DNA Fragment #5: DNA Fragment for $_{mb}$IL15$_{RA}$ and CCL19

A DNA fragment containing a nucleotide sequence encoding F2A, mouse IL-2SP, a mouse IL-15 construct "$_{mb}$IL15$_{RA}$" (fusion peptide consisting of IL-15, a linker, and full-length IL-15Rα), F2A, and mouse CCL19 was synthesized. SEQ ID NO: 8 (FIG. 11) shows the nucleotide sequence of the entire DNA fragment #5. In SEQ ID NO: 8, the bases at positions 7 to 81 form a sequence encoding the first F2A, the bases at positions 82 to 141 form a sequence encoding mouse IL-2SP, the bases at positions 142 to 1311 form a sequence encoding $_{mb}$IL15$_{RA}$ (among them, the bases at positions 142 to 540 encode mouse IL-15 (excluding signal sequences and stop codons), the bases at positions 541 to 618 serve as a linker, and the bases at positions 619 to 1311 encode mouse IL-15Rα (full-length)), the bases at positions 1312 to 1386 form a sequence encoding the second F2A, and the bases at positions 1390 to 1713 form a sequence encoding mouse CCL19. SEQ ID NO: 9 shows the amino acid sequence of the entire fusion protein that is expressed by the nucleotide sequence at positions 7 to 1713 of DNA fragment #5, self-cleaves at two F2A sites, and contains $_{mb}$IL15$_{RA}$.

[B: CAR-T Cell-Producing Step] Production of $_{mb}$IL15$_{RA}$_CCL19_Anti-Human CD20 CAR-T Cells A retrovirus-containing preparation was obtained in step 1 in the same manner as in the CAR-T cell-producing step of Example 1-1 except that the $_{mb}$IL15$_{RA}$_CCL19_anti-human CD20 CAR expression vector obtained by the aforementioned vector-producing step was used as a retrovirus expression vector, instead of the IL15$_{LSP}$_CCL19_anti-human CD20 CAR expression vector, to produce mouse T cells expressing the genes of anti-human CD20 CAR, $_{mb}$IL15$_{RA}$, and CCL19 contained in the retrovirus ($_{mb}$IL15$_{RA}$_CCL19_anti-human CD20 CAR-T cells, hereinafter referred to as "$_{mb}$IL15×CCL19 CAR-T cells") in step 2.

[Example 1-4] $_{sushi}$IL15 (Secretory IL-15RA/IL-15 Fusion Protein)×CCL19 CAR-T Cells

[A: Vector-Producing Step] Production of $_{sushi}$IL15_CCL19_Anti-Human CD20 CAR Expression Vector Using the same DNA fragment 1 and DNA fragment 2 as in step 1 of Example 1-1 and DNA fragment #6 as described below, instead of DNA fragment #3, a construct was produced in the same manner as in step 2 of Example 1-1, to obtain an anti-human CD20 CAR_F2A_$_{sushi}$IL15_F2A_CCL19-containing pMSGV retrovirus expression vector ($_{sushi}$IL15_CCL19_anti-human CD20 CAR expression vector).

DNA Fragment #6: DNA Fragment for $_{sushi}$IL15 and CCL19

A DNA fragment containing a nucleotide sequence encoding F2A, a mouse IL-15 construct "$_{sushi}$IL15" (fusion peptide consisting of IL-15Rα sushi domain, a linker, and IL-15), F2A, and mouse CCL19 was synthesized. SEQ ID NO: 10 (FIG. 12) shows the nucleotide sequence of the entire DNA fragment #6. In SEQ ID NO: 10, the bases at positions 7 to 81 form a sequence encoding the first F2A, the bases at positions 82 to 777 form a sequence encoding $_{sushi}$IL15 (among them, the bases at positions 82 to 375 encode the SP and the sushi domain of mouse IL-15Rα, the bases at positions 376 to 435 serve as a linker, and the bases at positions 436 to 777 encode mouse IL-15 (excluding signal sequences and propeptides)), the bases at positions 778 to 852 form a sequence encoding the second F2A, and the bases at positions 856 to 1179 form a sequence encoding mouse CCL19. SEQ ID NO: 11 shows the amino acid sequence of the entire fusion protein that is expressed by the nucleotide sequence at positions 7 to 1179 of DNA fragment #6, self-cleaves at two F2A sites, and contains $_{sushi}$IL15.

[B: CAR-T Cell-Producing Step] Production of $_{sushi}$IL15_CCL19_Anti-Human CD20 CAR-T Cells A retrovirus-containing preparation was obtained in step 1 in the same manner as in the CAR-T cell-producing step of Example 1-1 except that the $_{sushi}$IL15_CCL19_anti-human CD20 CAR expression vector obtained by the aforementioned vector-producing step was used as a retrovirus expression vector, instead of the IL15$_{LSP}$_CCL19_anti-human CD20 CAR expression vector, to obtain mouse T cells expressing the genes of anti-human CD20 CAR, $_{sushi}$IL15, and CCL19 contained in the retrovirus ($_{sushi}$IL15_CCL19_anti-human CD20 CAR-T cells, hereinafter referred to as "$_{sushi}$IL15×CCL19 CAR-T cells") in step 2.

[Example 2] IL-18×CCL19 CAR-T Cells

[A: Vector-Producing Step] Production of IL18_CCL19_Anti-Human CD20 CAR Expression Vector Using the same DNA fragment 1 and DNA fragment 2 as in step 1 of Example 1-1 and DNA fragment #7 as described below, instead of DNA fragment #3, a construct was produced in the same manner as in step 2 of Example 1-1, to obtain an anti-human CD20 CAR_F2A_IL-18_F2A_CCL19-containing pMSGV retrovirus expression vector (IL18_CCL19_anti-human CD20 CAR expression vector).

DNA Fragment #7: DNA Fragment for IL-18 and CCL19

A DNA fragment containing a nucleotide sequence encoding the first F2A, mouse IL-18, the second F2A, and mouse CCL19 was artificially synthesized. SEQ ID NO: 12 (FIG. 13) shows the nucleotide sequence of the entire DNA fragment #7. In SEQ ID NO: 12, the bases at positions 7 to 81 form a sequence encoding the first F2A, the bases at positions 82 to 657 form a sequence encoding mouse IL-18, the bases at positions 658 to 732 form a sequence encoding the second F2A, and the bases at positions 736 to 1059 form a sequence encoding mouse CCL19. SEQ ID NO: 13 shows the amino acid sequence of the entire fusion protein that is expressed by the nucleotide sequence at positions 7 to 1059 of DNA fragment #7 and self-cleaves at two F2A sites.

[B: CAR-T Cell-Producing Step] Production of IL18_CCL19_Anti-Human CD20 CAR-T Cells A retrovirus-containing preparation was obtained in step 1 in the same manner as in the CAR-T cell-producing step of Example 1-1 except that the IL18_CCL19_anti-human CD20 CAR expression vector obtained by the aforementioned vector-producing step was used as a retrovirus expression vector, instead of the IL15$_{LSP}$_CCL19_anti-human CD20 CAR expression vector, to obtain mouse T cells expressing the genes of anti-human CD20 CAR, IL-18, and CCL19 contained in the retrovirus (IL18_CCL19_anti-human CD20 CAR-T cells, hereinafter referred to as "IL18×CCL19 CAR-T cells") in step 2.

[Example 3] IL-21×CCL19 CAR-T Cells

[A: Vector-Producing Step] Production of IL21_CCL19_Anti-Human CD20 CAR Expression Vector Using the same DNA fragment 1 and DNA fragment 2 as in step 1 of Example 1-1 and DNA fragment #8 as described below, instead of DNA fragment #3, a construct was produced in the same manner as in step 2 of Example 1-1, to obtain an anti-human CD20 CAR_F2A_IL-21_F2A_CCL19-containing pMSGV retrovirus expression vector (IL21_CCL19_anti-human CD20 CAR expression vector).

DNA Fragment #8: DNA Fragment for IL-21 and CCL19

A DNA fragment containing a nucleotide sequence encoding the first F2A, mouse IL-21, the second F2A, and mouse CCL19 was artificially synthesized. SEQ ID NO: 14 (FIG. 14) shows the nucleotide sequence of the entire DNA fragment #8. In SEQ ID NO: 14, the bases at positions 7 to 81 form a sequence encoding the first F2A, the bases at positions 82 to 567 form a sequence encoding mouse IL-21, the bases at positions 568 to 642 form a sequence encoding the second F2A, and the bases at positions 646 to 969 form a sequence encoding mouse CCL19. SEQ ID NO: 15 shows the amino acid sequence of the entire fusion protein that is expressed by the nucleotide sequence at positions 7 to 969 of DNA fragment #8 and self-cleaves at two F2A sites.

[B: CAR-T Cell-Producing Step] Production of IL21_CCL19_Anti-Human CD20 CAR-T Cells A retrovirus-containing preparation was obtained in step 1 in the same manner as in the CAR-T cell-producing step of Example 1-1 except that the IL21_CCL19_anti-human CD20 CAR expression vector obtained by the aforementioned vector-producing step was used as a retrovirus expression vector, instead of the IL15$_{LSP}$_CCL19_anti-human CD20 CAR expression vector, to obtain mouse T cells expressing the genes of anti-human CD20 CAR, IL-21, and CCL19 contained in the retrovirus (IL21_CCL19_anti-human CD20 CAR-T cells, hereinafter referred to as "IL21×CCL19 CAR-T cells") in step 2.

[Example 4] $_{sc}$IL27×CCL19 CAR-T Cells

[A: Vector-Producing Step] Production of $_{sc}$IL27_CCL19_Anti-Human CD20 CAR Expression Vector Using the same DNA fragment 1 and DNA fragment 2 as in step 1 of Example 1-1 and DNA fragment #9 as described below, instead of DNA fragment #3, a construct was produced in the same manner as in step 2 of Example 1-1, to obtain an anti-human CD20 CAR_F2A_scIL-27_F2A_CCL19-containing pMSGV retrovirus expression vector ($_{sc}$IL27_CCL19_anti-human CD20 CAR expression vector).

DNA fragment #9: DNA fragment for $_{sc}$IL27 and CCL19

A DNA fragment containing a nucleotide sequence encoding the first F2A, a mouse IL-27 construct "scIL27" (fusion peptide consisting of p28, a linker, and EBI3), the second F2A, and CCL19 was artificially synthesized. SEQ ID NO: 16 (FIG. 15) shows the nucleotide sequence of the entire DNA fragment #9. In SEQ ID NO: 16, the bases at positions 7 to 81 form a sequence encoding the first F2A, the bases at positions 82 to 1437 form a sequence encoding $_{sc}$IL27 (among them, the bases at positions 82 to 765 encode mouse EBI3, the bases at positions 766 to 819 serve as a linker, and the bases at positions 820 to 1437 encode mouse p28), the bases at positions 1438 to 1512 form a sequence encoding the second F2A, and the bases at positions 1516 to 1839 form a sequence encoding mouse CCL19. SEQ ID NO: 17 shows the amino acid sequence of the entire fusion protein that is expressed by the nucleotide sequence at positions 7 to 1839 of DNA fragment #9, self-cleaves at two F2A sites, and contains $_{sc}$IL27.

[B: CAR-T Cell-Producing Step] $_{sc}$IL27_CCL19_Anti-Human CD20 CAR-T Cell-Producing Step A retrovirus-containing preparation was obtained in step 1 in the same manner as in the CAR-T cell-producing step of Example 1-1 except that the $_{sc}$IL27_CCL19_anti-human CD20 CAR expression vector obtained by the aforementioned vector-producing step was used as a retrovirus expression vector, instead of the IL15$_{LSP}$_CCL19_anti-human CD20 CAR expression vector, to obtain mouse T cells expressing the genes of anti-human CD20 CAR, $_{sc}$IL27, and CCL19 contained in the retrovirus ($_{sc}$IL27_CCL19_anti-human CD20 CAR-T cells, hereinafter referred to as "$_{sc}$IL27×CCL19 CAR-T cells") in step 2.

[Comparative Example 1] Transduction (−) T Cells

Mouse T cells that were only activated (hereinafter referred to as "transduction (−) T cells") were produced by the same procedure except that the production of the retroviral vector and the transfection into T cells using the retroviral vector were not performed, and an equivalent amount of a DMEM medium used for GP2-293 cell culture was added, instead of the IL15$_{LSP}$_CCL19_anti-human CD20 CAR expression vector preparation, in step 2 of step B of Example 1-1.

[Comparative Example 2] Conv. CAR-T Cells

[A: Vector-Producing Step] Production of Anti-Human CD20 CAR Expression Vector

An anti-human CD20 CAR_MCS-containing pMSGV retrovirus expression vector was produced using DNA fragment 1, DNA fragment 2, and the pMSGV retroviral vector by the same procedure as in the middle of step 2 of step A of Example 1-1. This was used as a control retrovirus expression vector (anti-human CD20 CAR expression vector) that does not co-express cytokines and chemokines.

[B: CAR-T Cell-Producing Step] Production of Anti-Human CD20 CAR-T Cells

A retrovirus-containing preparation was obtained in step 1 in the same manner as in the CAR-T cell-producing step of Example 1-1 except that an anti-human CD20 CAR expression vector was used as a retrovirus expression vector, instead of the IL15$_{LSP}$_CCL19_anti-human CD20 CAR expression vector, to obtain mouse T cells expressing only the anti-human CD20 CAR contained in the retrovirus (not expressing cytokines and chemokines) (anti-human CD20 CAR-T cells, hereinafter referred to as "conv. CAR-T cells") in step 2.

[Experimental Example 1] Confirmation of Expression Level of CAR, Cytokine, and Chemokine Introduced

[A: Measurement of CAR Expression by Flow Cytometry]

Using the T cells produced in Examples and Comparative Examples above, the expression level of the anti-human CD20 CAR on the cell surface was analyzed by flow cytometry, as described below.

A flow cytometer "BD FACSCanto™ II" (BD Biosciences) was used for flow cytometry, and a FlowJo software (BD Biosciences) was used for data analysis.

The T cells were treated using a biotin-labeled protein L (which specifically binds to the κ light chain of anti-human CD20 scFv) and Brilliant Violet™ 421 (BV421)-bound streptavidin, to detect CAR expression. At the same time, the CD8-positive rate in each T cell population was measured using an allophycocyanin (APC)-bound anti-mouse CD8 monoclonal antibody (BioLegend). Since CD8-positive T cells are generally considered to have direct cytotoxic activity, the presence (positive rate) of CD8-positive T cells can support the potency.

FIG. 1 shows the results. It was confirmed that 60% or more of the cell population of the CAR-T cells in all Examples (and Comparative Example 2) expressed (i.e., were positive for) the anti-human CD20 CAR.

[B: Measurement of Amounts of Cytokine and Chemokine Secreted]

The culture supernatants of the T cells were collected 42 hours after the transduction, the concentrations of IL-15, IL-18, IL-21, IL-27, and CCL19 were measured using a commercially available ELISA kit (available from MBL only for IL-18, and R&D systems for others).

FIG. 2 shows the results. For IL-15 (FIG. 2A), IL-15 was detected at a concentration of 250 μg/mL from the culture supernatant of the CAR-T cells of Example 1-1 (15LSP×19 CAR-T). Meanwhile, the concentrations of IL-15 in the culture supernatants of the CAR-T cells of Example 1-2 (s15RA×19 CAR-T), Example 1-3 (mb15RA×19 CAR-T), and Example 1-4 (sushi15×19 CAR-T) were similar to those of non-transduced activated T cells (transduction (−): Comparative Example 1) and anti-human CD20 CAR-expressing T cells (conv. CAR-T: Comparative Example 2) as a control, and no secretion of IL-15 was observed by the ELISA kit used in Experimental Example 1. However, since Example 1-2, Example 1-3, and Example 1-4 exhibited a remarkable cell proliferation effect in Experimental Example 2, which will be described below, it is understood that IL-15 was expressed and secreted in these examples as well as in Example 1-1.

For IL-18 (FIG. 2B), IL-18 was detected at a concentration of 150 μg/mL or more from the culture supernatant of the CAR-T cells of Example 2 (18×19 CAR-T). Meanwhile, the amount secreted from the anti-human CD20 CAR-expressing T cells (conv. CAR-T: Comparative Example 2) as a control into the culture supernatant was as small as from the non-transduced activated T cells (transduction (−): Comparative Example 1).

For IL-21 (FIG. 2C), IL-18 was detected at a concentration of 400 μg/mL or more from the culture supernatant of the CAR-T cells of Example 3 (21×19 CAR-T). Meanwhile, the amount secreted from the anti-human CD20 CAR-expressing T cells (conv. CAR-T: Comparative Example 2) as a control was below the detection limit (Not Detected) as well as from the non-transduced activated T cells (transduction (−): Comparative Example 1).

For IL-27 (FIG. 2D), p28 that is a sub-unit of IL-27 was detected at a concentration of 250 μg/mL or more from the culture supernatant of the CAR-T cells of Example 4 (sc27×19 CAR-T). Meanwhile, the amount secreted from the anti-human CD20 CAR-T cells (conv. CAR-T: Comparative Example 2) as a control was similar to that from the non-transduced activated T cells (transduction (−): Comparative Example 1) (at a concentration of about 50 μg/mL in the culture supernatant).

For CCL19 (FIG. 2E), while the concentrations in the culture supernatants of the anti-human CD20 CAR-T cells (conv. CAR-T: Comparative Example 2) as a control and the non-transduced activated T cells (transduction (−): Comparative Example 1) were below the detection limit, the concentrations in the culture supernatant of the CAR-T cells of Examples were 150 to 500 pg/mL.

[Experimental Example 2] Evaluation of In Vitro Proliferative Capacity of CAR-T Cells Using the T cells produced in Examples and Comparative Examples above, whether or not each cytokine produced from T cells (IL-15, IL-18, IL-21, and IL-27) exerted biological functions and exhibited immunoinducing effects was determined by measuring the number and proliferative capacity of the CAR-T cells, as follows.

The T cells were stained with CytoTell™ UltraGreen (AAT Bioquest) and then co-cultured in the same well as that of P815 mastocytoma (hCD20/P815) treated with mitomycin C and genetically transformed to express human CD20, followed by stimulation. After culturing for 3 days, 5 days, or 7 days from the start of stimulation, the cells were collected and analyzed by flow cytometry. The cells were stained with an APC-bound anti-Thy1.2 monoclonal antibody (eBioscience), and the number of Thy1.2-positive cells in the T cell (lymphocyte) population was counted as surviving T cells.

FIG. 3 shows the results. The transduction (−) T cells (Comparative Example 1) did not undergo activation stimulation even when co-cultured with hCD20/P815 cells, and the number of living cells was 1/10 or less on day 3 of culture. Meanwhile, it was confirmed on day 3 of culture that proliferation in the number of living cells equivalent to or greater than the conv. CAR-T cells (Comparative Example 2) as a control was maintained in the $IL15_{LSP}$×CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), the IL-21×CCL19 CAR-T cells (Example 3), and the $_{sc}$IL27×CCL19 CAR-T cells (Example 4), which were co-cultured with hCD20/P815 cells. Further, when the culture was continued until day 7, the $_{s}IL15_{RA}$×CCL19 CAR-T cells (Example 1-2), the $_{mb}IL15_{RA}$×CCL19 CAR-T cells (Example 1-3), and the $_{sushi}$IL15×CCL19 CAR-T cells (Example 1-4) especially exhibited remarkable cell proliferation. The $IL15_{LSP}$×CCL19 CAR-T cells (Example 1-1), the IL-18×CCL19 CAR-T cells (Example 2), the IL-21×CCL19 CAR-T cells (Example 3), and the $_{sc}$IL27×CCL19 CAR-T cells (Example 4) maintained the number of cells equivalent to the conv. CAR-T cells (Comparative Example 2) as a control from day 3 to day 7 of culture.

In addition, histogram analysis of the staining intensity with a CytoTell reagent in the Thy1.2-positive cell population was performed. FIG. 4 shows the results for each cell population 5 days after the start of stimulation. In the $IL15_{LSP}$×CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), and the IL-21×CCL19 CAR-T cells (Example 3), the proportion of the cell population of the second generation (after one division) especially decreased, and the proportion of the cell population after the fifth generation (after four or more divisions) increased, as compared with the conv. CAR-T cells (Comparative Example 2) as a control.

From the results shown in FIG. 3 and FIG. 4, it was revealed that the combinations of IL-15/IL-15Rα fusion protein and CCL-19 produced in the $_{s}IL15_{RA}$×CCL19 CAR-T cells (Example 1-2), the $_{mb}IL15_{RA}$×CCL19 CAR-T cells (Example 1-3), and the $_{sushi}$IL15×CCL19 CAR-T cells (Example 1-4) were especially preferable for promoting survival and proliferation of CAR-T cells and exerting biological functions.

[Experimental Example 3] Evaluation of Tumor Cytotoxic Activity of CAR-T Cells

Using the T cells produced in Examples and Comparative Examples above, the target antigen-specific tumor cytotoxic activity was examined.

[A: Measurement of Tumor Cytotoxic Activity by Flow Cytometry]

P815 mastocytomas (hCD20/P815) genetically transformed to express human CD20 were used as target tumor cells, and P815 mastocytomas (P815) that were not genetically transformed as above were used as control tumor cells.

After the target tumor cells or control tumor cells were collected and seeded on a culture plate, the CAR-T cells of Examples (the $IL15_{LSP}$×CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), the IL-21×CCL19 CAR-T cells (Example 3), and the $_{sc}$IL27×CCL19 CAR-T cells (Example 4)), or the CAR-T cells of Comparative Example 2 (conv. CAR-T cells) were added thereto as effector T cells, and the cells were co-cultured for 72 hours. The effector T cells were added so that the number of CAR-positive cells was 1/3 of the target tumor cells (E:T ratio=1:3), and the total number of T cells seeded was set to be the same in each group by adding, according to the number of T cells seeded with the lowest CAR expression rate, non-transduced T cells to the other T cell groups. After co-culturing for 72 hours, all cells were collected, analyzed by flow cytometry, and measured for the number of living cells. The cells were stained with an APC-bound anti-Thy1.2 monoclonal antibody (eBioscience) and a Zombie Green Fixable Viability Kit (BioLegend), and the proportions of T cells and tumor cells in the living cell population were calculated from the Thy1.2-positive rate. The number of living cells was measured using NucleoCounter NC-200 (chemometec).

FIG. 5 shows the results. As shown in FIG. 5A, the number of hCD20/P815 tumor cells after co-culturing for 72 hours was calculated from the Thy1.2-negative rate in the living cells. As a result, the number of hCD20/P815 tumor cells co-cultured with each of the $IL15_{LSP}$×CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), the IL-21×CCL19 CAR-T cells (Example 3), or the scIL27×CCL19 CAR-T cells (Example 4) significantly decreased as compared with the transduction (−) T cells (Comparative Example 1) and also further decreased as compared with the conv. CAR-T cells (Comparative Example 2), and the tumor cells survived was 1% or less. Meanwhile, no decrease in tumor cells, P815 cells not expressing human CD20, was observed in any group, as shown in FIG. 5B, and no cytotoxicity non-specific to tumor cells not expressing human CD20 was confirmed.

[B: IFNγ Production Measurement by ELISA Assay]

As an index of activation of the target antigen-specific cytotoxic ability, interferon γ (IFNγ) produced from CAR-T cells was measured using a commercially available ELISA assay kit (R&D). The CAR-T cells of Examples (the $IL15_{LSP}$× CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), the IL-21×CCL19 CAR-T cells (Example 3), and the $_{sc}$IL27×CCL19 CAR-T cells (Example 4)), or the CAR-T cells of Comparative Example 2 (conv. CAR-T cells) were co-cultured with the P815 cells (control tumor cells) or hCD20-P815 cells (target tumor cells) to measure the amount of IFNγ in the culture supernatant 4 days after the co-culture.

FIG. 6 shows the results. As shown in FIG. 6A, the level of IFNγ was higher than in the conv. CAR-T cells (Comparative Example 2), and about 15 ng/ml or more of IFNγ was detected in the culture supernatant of any of the $IL15_{LSP}$×CCL19 CAR-T cells (Example 1-1), the $_{s}IL15_{RA}$×CCL19 CAR-T cells (Example 1-2), the $_{mb}IL15_{RA}$×CCL19 CAR-T cells (Example 1-3), the $_{sushi}$IL15×CCL19 CAR-T cells (Example 1-4), the IL-18×CCL19 CAR-T cells (Example 2), the IL-21×CCL19 CAR-T cells (Example 3), or the scIL27×CCL19 CAR-T cells (Example 4), which were co-cultured with the hCD20-P815 cells. The amount of IFNγ produced in the groups co-cultured with the transduction (−) T cells (Comparative Example 1) was below the detection limit. Meanwhile, the concentration of IFNγ in the culture supernatant of the CAR-expressing cells co-cultured with the P815 cells was 10 μg/mL or less, as shown in FIG. 6B.

From the above results of Experimental Example 3 (FIG. 5 and FIG. 6), it was confirmed that all the T cells of Examples and Comparative Example 2 exhibited a human CD20-expressing cell, that is, target antigen-specific cytotoxic activity.

[Experimental Example 4] Therapeutic Effect on Mouse Tumor Models

The therapeutic effect of the T cells produced in Example 1-3, Example 1-4, and Comparative Example 2 on a mouse melanoma tumor transplant model or a mouse colorectal cancer tumor model was examined using the following cancer-bearing mice.

(Therapeutic Effect on Mouse Melanoma Tumor Transplant Model)

$5\times10^5$ of mouse melanoma B16F10 genetically transformed to express human CD20 (B16F10-hCD20) was subcutaneously inoculated into C57BL/6N mice. An anticancer agent, cyclophosphamide (CPA, 50 mg/kg), was intraperitoneally administered on day 7 after the inoculation, and $1\times10^6$ of the CAR-T cells of Example 1-3 ($_{mb}IL15_{RA}$×CCL19 CAR-T), the CAR-T cells of Example 1-4 ($_{sushi}$IL15×CCL19 CAR-T), or the cells of Comparative Example 2 (Conv. CAR-T) were intravenously administered on day 10. As control groups, a CAR-T untreated group with only CPA administration and a group inoculated with B16F10-hCD20 mouse melanoma and thereafter untreated were set. The tumor volume in mice was measured twice a week.

FIG. 16 shows the results of the tumor volume of the mouse melanoma tumor transplant model. The horizontal axis indicates the number of days after the inoculation with the day on which B16F10-hCD20 was subcutaneously inoculated into the mice taken as day 0, and the vertical axis indicates the tumor volume (tumor major diameter×(tumor minor diameter)$^2$/2 (mm$^3$)). The standard deviation was calculated in each experimental group. "No treatment" means an untreated group, "CPA" means a group with only CPA administration, "CPA+Conv." means a group with CPA administration and subsequent administration of Comparative Example 2 (Conv. CAR-T), "CPA+$_{mb}IL15_{RA}$×19" means a group with CPA administration and subsequent administration of the CAR-T cells of Example 1-3 ($_{mb}IL15_{RA}$×CCL19 CAR-T), and "CPA+$_{sushi}IL15_{RA}$×19" means a group with CPA administration and subsequent administration of the CAR-T cells of Example 1-4 ($_{sushi}$IL15×CCL19 CAR-T).

As shown in FIG. 16, the effect of reducing the tumor volume was confirmed in the groups with administration of the CAR-T cells of Example 1-3 ($_{mb}IL15_{RA}$×CCL19 CAR-T) and the CAR-T cells of Example 1-4 ($_{sushi}IL15_{RA}$×CCL19 CAR-T), as compared with the groups with administration of Comparative Example 2 (Conv. CAR-T), the untreated groups (no treatment), and the groups with only CPA administration. Accordingly, it was revealed that the CAR-T cells of Example 1-3 ($_{mb}IL15_{RA}$×CCL19 CAR-T) and the CAR-T cells of Example 1-4 ($_{sushi}$IL15×CCL19 CAR-T) had excellent antitumor activity on the mouse melanoma tumor model.

(Therapeutic Effect on Mouse Colorectal Cancer Tumor Transplant Model)

$5\times10^5$ of mouse colorectal cancer MC38 (MC38-hCD20) genetically transformed to express human CD20 was subcutaneously inoculated into C57BL/6N mice. An anticancer agent, cyclophosphamide (CPA, 50 mg/kg), was intraperitoneally administered on day 7 after the inoculation, and $1\times10^6$ of the CAR-T cells of Example 1-3 ($_{mb}IL15_{RA}$×CCL19 CAR-T), the CAR-T cells of Example 1-4 ($_{sushi}$IL15×CCL19 CAR-T), or the cells of Comparative Example 2 (Conv. CAR-T) were intravenously administered on day 10. As control groups, a CAR-T untreated group with only CPA administration and a group inoculated with MC38-hCD20 mouse colorectal cancer and thereafter untreated were set. The tumor volume in mice was measured twice a week.

FIG. 17 shows the results of the tumor volume of the mouse colorectal cancer tumor transplant model. The horizontal axis indicates the number of days after the inoculation with the day on which MC38-hCD20 was subcutaneously inoculated into the mice taken as day 0, and the vertical axis indicates the tumor volume (tumor major diameter×(tumor minor diameter)$^2$/2 (mm$^3$)). The standard deviation was calculated in each experimental group. "No treatment" means an untreated group, "CPA" means a group with only CPA administration, "CPA+Conv." means a group with CPA administration and subsequent administration of Comparative Example 2 (Conv. CAR-T), "CPA+$_{mb}IL15_{RA}$×19" means a group with CPA administration and subsequent administration of the CAR-T cells of Example 1-3 ($_{mb}IL15_{RA}$×CCL19 CAR-T), and "CPA+$_{sushi}IL15_{RA}$×19" means a group with CPA administration and subsequent administration of the CAR-T cells of Example 1-4 ($_{sushi}$IL15×CCL19 CAR-T).

As shown in FIG. 17, the effect of reducing the tumor volume was confirmed in the groups with administration of the CAR-T cells of Example 1-3 ($_{mb}IL15_{RA}$×CCL19 CAR-T) and the CAR-T cells of Example 1-4 ($_{sushi}IL15_{RA}$×CCL19 CAR-T), as compared with the groups with administration of Comparative Example 2 (Conv. CAR-T), the untreated groups (no treatment), and the groups with only CPA administration. Accordingly, it was revealed that the CAR-T cells of Example 1-3 ($_{mb}IL15_{RA}$×CCL19 CAR-T) and the CAR-T cells of Example 1-4 ($_{sushi}$IL15×CCL19 CAR-T) had excellent antitumor activity also on the mouse colorectal cancer model.

In Examples and Experimental Examples above, mouse-derived T cells, a cytokine (fusion protein with IL-15 linked to IL-15Rα or the like) and a chemokine (CCL19) each containing the natural mouse amino acid sequence, were used, and in vivo tests in mice were conducted. However, those skilled in the art would be able to understand that, also in embodiments related to mammals other than mice, preferably humans, that is, in the case of using human-derived T cells, a cytokine (fusion protein with IL-15 linked to IL-15Rα or the like), and a chemokine (CCL19) each containing the natural human amino acid sequence, or in vivo tests in humans were conducted, the present invention could be carried out in the same manner, and the action and effect of the present invention would be exerted.

For example, the fusion protein containing $IL15_{LSP}$ which was carried out (produced and used) using the natural mouse amino acid sequence shown in SEQ ID NO: 5 can be carried out using the amino acid sequences at positions 1 to 29 (signal peptide portion) and 49 to 162 (IL-15 portion) in the natural human amino acid sequence for IL-15 shown in SEQ ID NO: 18 or using nucleic acids having the nucleotide sequence encoding such amino acid sequences.

The fusion protein containing ${}_{s}IL15_{RA}$ which was carried out using the natural mouse amino acid sequence shown in SEQ ID NO: 7 can be carried out using the amino acid sequence at positions 49 to 162 (IL-15 portion) in the natural human amino acid sequence for IL-15 shown in SEQ ID NO: 18 and the amino acid sequence at positions 31 to 205 (IL-15Rα extracellular domain) in the natural human amino acid sequence for IL-15Rα shown in SEQ ID NO: 19 or using nucleic acids having the nucleotide sequence encoding such amino acid sequences.

The fusion protein containing ${}_{mb}IL15_{RA}$ which was carried out using the natural mouse amino acid sequence shown in SEQ ID NO: 9 can be carried out using the amino acid sequence at positions 49 to 162 (IL-15 portion) in the natural human amino acid sequence for IL-15 shown in SEQ ID NO: 18 and the amino acid sequence at positions 1 to 267 (full-length IL-15Rα) in the natural human amino acid sequence for IL-15Rα shown in SEQ ID NO: 19 or using nucleic acids having the nucleotide sequence encoding such amino acid sequences.

The fusion protein containing ${}_{sushi}IL15$ which was carried out using the natural mouse amino acid sequence shown in SEQ ID NO: 11 can be carried out using the amino acid sequence at positions 49 to 162 (IL-15 portion) in the natural human amino acid sequence for IL-15 shown in SEQ ID NO: 18 and the amino acid sequence at positions 31 to 95 (sushi domain) in the natural human amino acid sequence for IL-15Rα shown in SEQ ID NO: 19 or using nucleic acids having the nucleotide sequence encoding such amino acid sequences.

INDUSTRIAL APPLICABILITY

The CAR-T cells according to the present invention that are excellent in persistence and proliferation are suitably used for producing a medicament for treating cancer or the like. Further, the expression vector according to the present invention is suitably used for producing the CAR-T cells.

Sequence Listing Free Text

SEQ ID NO: 1: The nucleotide sequence of DNA fragment containing an anti-human CD20 CAR (DNA fragment #1)

SEQ ID NO: 2: The amino acid sequence of a fusion protein expressed by the nucleotide sequence at positions 3 to 1637 of DNA fragment #1

SEQ ID NO: 3: The nucleotide sequence of a MCS DNA fragment encoding stop codons and restriction enzyme sites (DNA fragment #2)

SEQ ID NO: 4: The nucleotide sequence of $IL15_{LSP}$_F2A_CCL19 DNA fragment (DNA fragment #3)

SEQ ID NO: 5: The amino acid sequence of the entire fusion protein that is expressed by the nucleotide sequence at positions 7 to 969 of DNA fragment #3, self-cleaves at two F2A sites, and contains $IL15_{LSP}$ SEQ ID NO: 6: The amino acid sequence of ${}_{s}IL15_{RA}$_F2A_CCL19 DNA fragment (DNA fragment #4)

SEQ ID NO: 7: The amino acid sequence of the entire fusion protein that is expressed by the nucleotide sequence at positions 7 to 1539 of DNA fragment #4, self-cleaves at two F2A sites, and contains ${}_{s}IL15_{RA}$ SEQ ID NO: 8: The nucleotide sequence of ${}_{mb}IL15_{RA}$_F2A_CCL19 DNA fragment (DNA fragment #5)

SEQ ID NO: 9: The amino acid sequence of the entire fusion protein that is expressed by the nucleotide sequence at positions 7 to 1713 of DNA fragment #5, self-cleaves at two F2A sites, and contains ${}_{mb}IL15_{RA}$ SEQ ID NO: 10: The nucleotide sequence of ${}_{sushi}IL15$_F2A_CCL19 DNA fragment (DNA fragment #6)

SEQ ID NO: 11: The amino acid sequence of the entire fusion protein that is expressed by the nucleotide sequence at positions 7 to 1179 of DNA fragment #6, self-cleaves at two F2A sites, and contains ${}_{sushi}IL15$ SEQ ID NO: 12: The nucleotide sequence of IL-18_F2A_CCL19 DNA fragment (DNA fragment #7)

SEQ ID NO: 13: The amino acid sequence of the entire fusion protein that is expressed by the nucleotide sequence at positions 7 to 1059 of DNA fragment #7 and self-cleaves at two F2A sites SEQ ID NO: 14: The nucleotide sequence of IL-21_F2A_CCL19 DNA fragment (DNA fragment #8)

SEQ ID NO: 15: The amino acid sequence of the entire fusion protein that is expressed by the nucleotide sequence at positions 7 to 969 of DNA fragment #8 and self-cleaves at two F2A sites SEQ ID NO: 16: ${}_{sc}IL27$_F2A_CCL19 DNA fragment (DNA fragment #9)

SEQ ID NO: 17: The amino acid sequence of the entire fusion protein that is expressed by the nucleotide sequence at positions 7 to 1839 of DNA fragment #9, self-cleaves at two F2A sites, and contains ${}_{sc}IL27$ SEQ ID NO: 18: The amino acid sequence of natural human IL-15 (full length including signal peptide and propeptide parts) registered as UniProtKB-P40933

SEQ ID NO: 19: The amino acid sequence of natural human IL-15Rα (full length including signal peptide, sushi domain, extracellular domain, etc.) registered as UniProtKB-Q13261

The invention claimed is:

1. A T cell expressing:

(1) a chimeric antigen receptor (CAR);

(2) an exogeneous interleukin selected from the group consisting of interleukin-15 (IL-15), interleukin-18 (IL-18), interleukin-21 (IL-21), and interleukin-27 (IL-27); and (3) CC chemokine ligand 19 (CCL19), wherein said exogeneous interleukin is the only exogeneous interleukin expressed by the T cell.

2. The T cell according to claim 1, wherein the exogeneous interleukin is IL-15.

3. The T cell according to claim 2, wherein the IL-15 is linked to IL-15Rα to form a fusion protein.

4. The T cell according to claim 2, wherein the IL-15 forms a fusion protein, wherein the fusion protein is a fusion protein comprising IL-15LSP linked to IL-15 ($IL15_{LSP}$), a fusion protein comprising IL-15Rα extracellular domain linked to IL-15 ($_{s}IL15_{RA}$), a fusion protein comprising IL-15Rα containing a extracellular domain, a transmembrane domain and a intracellular domain of IL-15Rα linked to the C-terminus of IL-15 ($_{mb}IL15_{RA}$), or a fusion protein comprising IL-15Rα containing a signal peptide and a sushi domain of IL-15Rα linked to the N-terminus of IL-15 ($_{sushi}IL15$).

5. The T cell according to claim 3, wherein the fusion protein is a fusion protein comprising IL-15Rα containing a extracellular domain, a transmembrane domain and a intracellular domain of IL-15Rα linked to the C-terminus of IL-15 ($_{mb}IL15_{RA}$), or a fusion protein comprising IL-15Rα containing a signal peptide and a sushi domain of IL-15Rα linked to the N-terminus of IL-15 ($_{sushi}IL15$).

6. A medicament comprising the T cell according to claim 1.

7. The medicament according to claim 6, for use in the treatment of cancer.

8. The medicament according to claim 7, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

9. An expression vector comprising:

(1) a nucleic acid encoding a CAR;

(2) a nucleic acid encoding an exogeneous interleukin selected from the group consisting of IL-15, IL-18, IL-21, and IL-27; and (3) a nucleic acid encoding CCL19, wherein said exogeneous interleukin is the only exogeneous interleukin encoded by a nucleic acid of the expression vector.

10. The expression vector according to claim 9, wherein the exogeneous interleukin encoded is IL-15.

11. The expression vector according to claim 10, wherein the IL-15 is linked to IL-15Rα to form a fusion protein.

12. The expression vector according to claim 10, wherein the IL-15 forms a fusion protein, wherein the fusion protein is a fusion protein comprising IL-15LSP linked to IL-15 ($IL15_{LSP}$), a fusion protein comprising IL-15Rα extracellular domain linked to IL-15 ($_{s}IL15_{RA}$), a fusion protein comprising IL-15Rα containing a extracellular domain, a transmembrane domain and a intracellular domain of IL-15Rα linked to the C-terminus of IL-15 ($_{mb}IL15_{RA}$), or a fusion protein comprising IL-15Rα containing a signal peptide and a sushi domain of IL-15Rα linked to the N-terminus of IL-15 ($_{sushi}IL15$).

13. The expression vector according to claim 11, wherein the fusion protein is a fusion protein comprising IL-15Rα containing a extracellular domain, a transmembrane domain and a intracellular domain of IL-15Rα linked to the C-terminus of IL-15 ($_{mb}IL15_{RA}$), or a fusion protein comprising IL-15Rα containing a signal peptide and a sushi domain of IL-15Rα linked to the N-terminus of IL-15 ($_{sushi}IL15$).

14. A method for producing a CAR-T cell, comprising a step of introducing the expression vector according to claim 9 into a T cell.

15. A method for treating cancer, comprising a step of administering the T cell according to claim 1 to a subject in need of cancer treatment.

16. The treatment method according to claim 15, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

17. The T cell according to claim 1, for use as an active component for cancer treatment.

18. The T cell for use according to claim 15, wherein the cancer is melanoma, Merkel cell cancer, colorectal cancer, kidney cancer, breast cancer, ovarian cancer, fallopian tube cancer, cervical cancer, liver cancer, lung cancer, non-small cell lung cancer, head and neck cancer, small intestine cancer, prostate cancer, bladder cancer, rectal cancer, pancreatic cancer, Ewing's sarcoma, rhabdomyosarcoma, nasopharyngeal cancer, esophageal cancer, biliary tract cancer, neuroblastoma, osteosarcoma, acute myeloid leukemia, multiple myeloma, lymphoma, or leukemia.

* * * * *